US009447110B2

(12) United States Patent
Orwat et al.

(10) Patent No.: US 9,447,110 B2
(45) Date of Patent: Sep. 20, 2016

(54) SUBSTITUTED TETRAHYDROISOQUINOLINE COMPOUNDS AS FACTOR XIA INHIBITORS

(71) Applicant: BRISTOL-MYERS SQUIBB COMPANY, Princeton, NJ (US)

(72) Inventors: Michael J. Orwat, New Hope, PA (US); Donald J. P. Pinto, Churchville, PA (US); Leon M. Smith, II, Somerset, NJ (US); Shefali Srivastava, Karnataka (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/886,415

(22) Filed: Oct. 19, 2015

(65) Prior Publication Data

US 2016/0075715 A1 Mar. 17, 2016

Related U.S. Application Data

(63) Continuation of application No. 14/617,979, filed on Feb. 10, 2015, now Pat. No. 9,192,607, which is a continuation of application No. 14/117,513, filed as application No. PCT/US2012/059969 on Oct. 12, 2012, now Pat. No. 9,000,172.

(60) Provisional application No. 61/547,292, filed on Oct. 14, 2011.

(51) Int. Cl.

| | |
|---|---|
| ***C07D 491/113*** | (2006.01) |
| ***C07D 401/14*** | (2006.01) |
| ***C07D 413/14*** | (2006.01) |
| ***C07D 217/26*** | (2006.01) |
| ***C07D 401/04*** | (2006.01) |
| ***C07D 401/10*** | (2006.01) |
| ***C07D 471/10*** | (2006.01) |
| ***C07D 487/04*** | (2006.01) |
| ***C07D 487/08*** | (2006.01) |
| ***C07D 487/10*** | (2006.01) |
| ***C07D 491/10*** | (2006.01) |
| ***A61K 31/4725*** | (2006.01) |
| ***A61K 31/496*** | (2006.01) |
| ***A61K 31/5377*** | (2006.01) |
| ***A61K 31/541*** | (2006.01) |
| ***A61K 31/55*** | (2006.01) |
| ***A61K 31/551*** | (2006.01) |

(52) U.S. Cl.

CPC ....... *C07D 491/113* (2013.01); *A61K 31/4725* (2013.01); *A61K 31/496* (2013.01); *A61K 31/5377* (2013.01); *A61K 31/541* (2013.01); *A61K 31/55* (2013.01); *A61K 31/551* (2013.01); *C07D 217/26* (2013.01); *C07D 401/04* (2013.01); *C07D 401/10* (2013.01); *C07D 401/14* (2013.01); *C07D 413/14* (2013.01); *C07D 471/10* (2013.01); *C07D 487/04* (2013.01); *C07D 487/08* (2013.01); *C07D 487/10* (2013.01); *C07D 491/10* (2013.01)

(58) Field of Classification Search

None

See application file for complete search history.

(56) References Cited

U.S. PATENT DOCUMENTS

| | | | | |
|---|---|---|---|---|
| 5,624,936 A | | 4/1997 | deSolms | |
| 5,869,682 A | | 2/1999 | deSolms | |
| 9,000,172 B2 * | | 4/2015 | Orwat | C07D 401/14 546/146 |
| 9,192,607 B2 | | 11/2015 | Orwat et al. | |

FOREIGN PATENT DOCUMENTS

| | | |
|---|---|---|
| DE | 40 34 829 A1 | 5/1992 |
| EP | 0 525 420 B1 | 5/1999 |
| EP | 1 016 663 A1 | 7/2000 |
| EP | 1 125 925 A1 | 8/2001 |
| FR | 1525186 | 5/1968 |
| FR | 7155 M | 2/1970 |
| WO | WO 93/20099 A2 | 10/1993 |
| WO | WO 96/34010 A2 | 10/1996 |

(Continued)

OTHER PUBLICATIONS

Boger, D.L. et al., "Thermal Atropisomerism of Aglucovancomycin Derivatives: Preparation of (*M,M,M*)- and (*P,M,M*)-Aglucovancomycins", J. Am. Chem. Soc., vol. 120, No. 35, pp. 8920-8926 (1998).

Caballero, J. et al., "Quantitative Structure-Activity Relationship Modeling of Growth Hormone Secretagogues Agonist Activity of Some Tetrahydroisoquinoline 1-Carboxamides", Chem. Biol. Drug. Des., vol. 69, pp. 48-55 (2007).

Chan, J.C.Y. et al., "The Characterization of Mice with a Targeted Combined Deficiency of Protein C and Factor XI", American Journal of Pathology, vol. 158, No. 2, pp. 469-479 (2001).

(Continued)

*Primary Examiner* — Heidi Reese

(74) *Attorney, Agent, or Firm* — Hong Liu

(57) ABSTRACT

The present invention provides compounds of Formula (I):

(I)

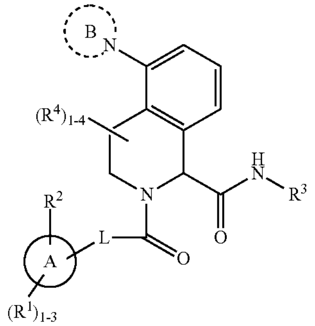

or stereoisomers, pharmaceutically acceptable salts thereof, wherein all of the variables are as defined herein. These compounds are inhibitors of factor XIa and/or plasma kallikrein which may be used as medicaments.

1 Claim, 11 Drawing Sheets

(56) References Cited

FOREIGN PATENT DOCUMENTS

| | | | |
|---|---|---|---|
| WO | WO 97/36891 | A1 | 10/1997 |
| WO | WO 99/15530 | A1 | 4/1999 |
| WO | WO 99/47545 | A2 | 9/1999 |
| WO | WO 99/61444 | A2 | 12/1999 |
| WO | WO 00/18733 | A1 | 4/2000 |
| WO | WO 00/40571 | A1 | 7/2000 |
| WO | WO 00/61608 | A2 | 10/2000 |
| WO | WO 01/85695 | A1 | 11/2001 |
| WO | WO 02/18369 | A2 | 3/2002 |
| WO | WO 03/011222 | A2 | 2/2003 |
| WO | WO 03/041641 | A2 | 5/2003 |
| WO | WO 2004/080971 | A1 | 9/2004 |
| WO | WO 2004/094372 | A2 | 11/2004 |
| WO | WO 2005/014533 | A2 | 2/2005 |
| WO | WO 2005/099709 | A2 | 10/2005 |
| WO | WO 2005/123050 | A2 | 12/2005 |
| WO | WO 2005/123680 | A1 | 12/2005 |
| WO | WO 2006/017295 | A2 | 2/2006 |
| WO | WO 2006/076575 | A2 | 7/2006 |
| WO | WO 2006/089005 | A2 | 8/2006 |
| WO | WO 2007/054453 | A2 | 5/2007 |
| WO | WO 2007/070816 | A2 | 6/2007 |
| WO | WO 2007/070818 | A1 | 6/2007 |
| WO | WO 2007/070826 | A1 | 6/2007 |
| WO | WO 2007/076431 | A1 | 7/2007 |
| WO | WO 2008/076805 | A2 | 6/2008 |
| WO | WO 2008/079836 | A2 | 7/2008 |
| WO | WO 2008/157162 | A1 | 12/2008 |
| WO | WO 2009/114677 | A1 | 9/2009 |
| WO | WO 2010/151317 | A1 | 12/2010 |
| WO | WO 2011/002520 | A2 | 1/2011 |
| WO | WO 2011/017296 | A1 | 2/2011 |
| WO | WO 2011/100401 | A1 | 8/2011 |
| WO | WO 2011/100402 | A1 | 8/2011 |
| WO | WO 2013/009527 | A2 | 1/2013 |
| WO | WO 2013/022814 | A1 | 2/2013 |
| WO | WO 2013/022818 | A1 | 2/2013 |
| WO | WO 2013/055984 | A1 | 4/2013 |
| WO | WO 2013/056034 | A1 | 4/2013 |
| WO | WO 2013/056060 | A1 | 4/2013 |
| WO | WO 2013/093484 | A1 | 6/2013 |
| WO | WO 2013/111107 | A1 | 8/2013 |
| WO | WO 2013/111108 | A1 | 8/2013 |
| WO | WO 2013/118805 | A1 | 8/2013 |
| WO | WO 2013/167669 | A1 | 11/2013 |
| WO | WO 2013/174937 | A1 | 11/2013 |
| WO | WO 2014/014050 | A1 | 1/2014 |
| WO | WO 2014/022766 | A1 | 2/2014 |
| WO | WO 2014/022767 | A1 | 2/2014 |
| WO | WO 2014/059202 | A1 | 4/2014 |
| WO | WO 2014/059203 | A1 | 4/2014 |
| WO | WO 2014/059214 | A1 | 4/2014 |
| WO | WO 2014/108679 | A1 | 7/2014 |
| WO | WO 2014/108685 | A1 | 7/2014 |
| WO | WO 2014/120346 | A1 | 8/2014 |
| WO | WO 2014/160668 | A1 | 10/2014 |
| WO | WO 2015/116882 | A1 | 8/2015 |
| WO | WO 2015/116885 | A1 | 8/2015 |
| WO | WO 2015/116886 | A1 | 8/2015 |

OTHER PUBLICATIONS

Chen, X. et al., Chapter 32: "The use of bioisosteric groups in lead optimization", Annual Reports in Medicinal Chemistry, vol. 38, pp. 333-346, Elsevier Inc., publ. (2003).

Cho, J.E. et al., "Characterization of Binding Mode for Human Coagulation Factor XI (FXI) Inhibitors", Bull. Korean Chem. Soc., vol. 34, No. 4, pp. 1212-1220 (2013).

Crosby, J.R. et al., "Antithrombotic Effect of Antisense Factor XI Oligonucleotide Treatment in Primates", Arterioscler. Thromb. Vasc. Biol., vol. 33, pp. 1670-1678 (2013), and vol. 33, pp. e127 and e130 (errata) (2013).

Evans, D.A. et al., "Total Syntheses of Vancomycin and Eremomycin Aglycons", Angew. Chem. Int. Ed., vol. 37, No. 19, pp. 2700-2704 (1998).

Gailani, D. et al., "A murine model of factor XI deficiency", Blood Coagulation and Fibrinolysis, vol. 8, pp. 134-144 (1997).

Gailani, D., "Gene Targeting in Hemostasis, Factor XI", Frontiers in Bioscience, vol. 6, pp. 201-207 (2001).

Gruber, A. et al., "Factor XI-dependence of surface- and tissue factor-initiated thrombus propagation in primates", Blood, vol. 102, No. 3, pp. 953-955 (2003).

Hoffman, M., "A cell-based model of coagulation and the role of factor Vlla", Blood Reviews, vol. 17, pp. S1-S5 (2003).

Jiang, G. et al., "Highly Efficient Oxidation of Amines to Imines by Singlet Oxygen and Its Application in Ugi-Type Reactions", Organic Letters, vol. 11, No. 20, pp. 4568-4571 (2009).

Li, J.J. et al., "Tetrahydroisoquinoline 1-carboxamides as growth hormone secretagogues", Bioorganic & Medicinal Chemistry Letters, vol. 15, pp. 1799-1802 (2005).

Matafonov, A. et al., "Evidence for factor IX-independent roles for factor XIa in blood coagulation", Journal of Thrombosis and Haemostasis, vol. 11, pp. 2118-2127 (2013).

MayoClinic.com, "Pulmonary Embolism: Prevention", http://www.mayoclinic.com/health/pulmonary-embolism/DS00429/DSECTION=prevention, accessed May 20, 2013.

Meijers, J.C.M. et al., "High Levels of Coagulation Factor XI as a Risk Factor for Venous Thrombosis", The New England Journal of Medicine, vol. 342, pp. 696-701 (2000).

Minnema, M.C. et al., "Activation of Clotting Factors XI and IX in Patients with Acute Myocardial Infarction", Arterioscler. Thromb. Vasc. Biol., vol. 20, pp. 2489-2493 (2000).

Murakami, T. et al., "Evaluation of Factor XIa-$\alpha_1$-Antitrypsin in Plasma, a Contact Phase-Activated Coagulation Factor-Inhibitor Complex, in Patients with Coronary Artery Disease", Arteriosclerosis, Thrombosis, and Vascular Biology, vol. 15, No. 8, pp. 1107-1113 (1995).

Ngouansavanh, T. et al., "IBX-Mediated Oxidative Ugi-Type Multicomponent Reactions: Application to the N and C1 Functionalization of Tetrahydroisoquinoline", Angew. Chem. Int. Ed., vol. 46, pp. 5775-5778 (2007).

Rosen, E.D. et al., "FXI is Essential for Thrombus Formation Following $FeCl_3$-Induced Injury of the Carotid Artery in the Mouse", Thromb. Haemost., vol. 87, pp. 774-776 (2002).

Schumacher, W.A. et al., "Inhibition of Factor XIa as a New Approach to Anticoagulation", Arteriorscler. Thromb. Vasc. Biol., vol. 30, pp. 388-392 (2010).

Schuster, I. et al., "Convenient Synthesis of 1,2,3,4-Tetrahydroisoquinoline-1-Carboxylic Acid Derivatives via Isocyanide-Based Three-Component Reactions", Synthetic Communications, vol. 40, pp. 2488-2498 (2010).

Schuster, I. et al., "Synthesis of 1,2,3,4-Tetrahydroisoquinoline-1-Carboxylic Acid Derivatives Via Ugi Reactions", Letters in Organic Chemistry, vol. 4, No. 2, pp. 102-108 (2007).

Schuster, I. et al., "Synthesis of 1,2,3,4-Tetrahydroisoquinoline-1-carboxylic Acid Derivatives via Ugi Reactions", Magyar Kémiai Folyóirat (Hungarian Journal of Chemistry), vol. 116, No. 3, pp. 126-130 (2010).

Walsh, P.N., "Platelets and Factor XI Bypass the Contact System of Blood Coagulation", Thrombosis and Haemostasis, vol. 82, No. 2, pp. 234-242 (1999).

Wang, X. et al., "Effects of factor IX or factor XI deficiency on ferric chloride-induced carotid artery occlusion in mice", Journal of Thrombosis and Haemostasis, vol. 3, pp. 695-702 (2005).

Wu, Y.-J. et al., "Discovery of (*S,E*)-3-(2-fluorophenyl)-*N*-(1-(3-(pyridin-3-yloxy)phenyl)ethyl)-acrylamide as a potent and efficacious KCNQ2 (Kv7.2) opener for the treatment of neuropathic pain", Bioorganic & Medicinal Chemistry Letters, vol. 23, pp. 6188-6191 (2013).

* cited by examiner

SUBSTITUTED TETRAHYDROISOQUINOLINE COMPOUNDS AS FACTOR XIA INHIBITORS

CROSS-REFERENCE TO RELATED APPLICATIONS

This application is a Continuation of U.S. application Ser. No. 14/617,979, filed Feb. 10, 2015 which is a continuation of U.S. application Ser. No. 14/117,513 filed Nov. 13, 2013, which is the 371 National Stage of International Application No. PCT/2012/059969, filed on Oct. 12, 2012, which claims the priority benefit of U.S. Provisional Application No. 61/547,292, filed Oct. 14, 2011; the contents of which are herein incorporated by reference in their entirety.

FIELD OF THE INVENTION

The present invention provides novel substituted tetrahydroisoquinoline (THQ) compounds, and their analogues thereof, which are inhibitors of factor XIa or plasma kallikrein, compositions containing them, and methods of using them, for example, for the treatment or prophylaxis of thromboembolic disorders.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.,* 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews,* 17:51-55 (2003)). Therefore, factor XIa plays a key role in propagating this amplification loop and is thus an attractive target for anti-thrombotic therapy.

SUMMARY OF THE INVENTION

The present invention provides novel substituted tetrahydroisoquinoline compounds, and their analogues thereof, including stereoisomers, tautomers, pharmaceutically acceptable salts, or solvates thereof, which are useful as selective inhibitors of serine protease enzymes, especially factor XIa and/or plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two, other agent(s).

These and other features of the invention will be set forth in expanded form as the disclosure continues.

BRIEF DESCRIPTION OF THE DRAWINGS

The invention is illustrated by reference to the accompanying drawings described below.

DETAILED DESCRIPTION OF THE INVENTION

I. Compounds of the Invention

Figure 1:
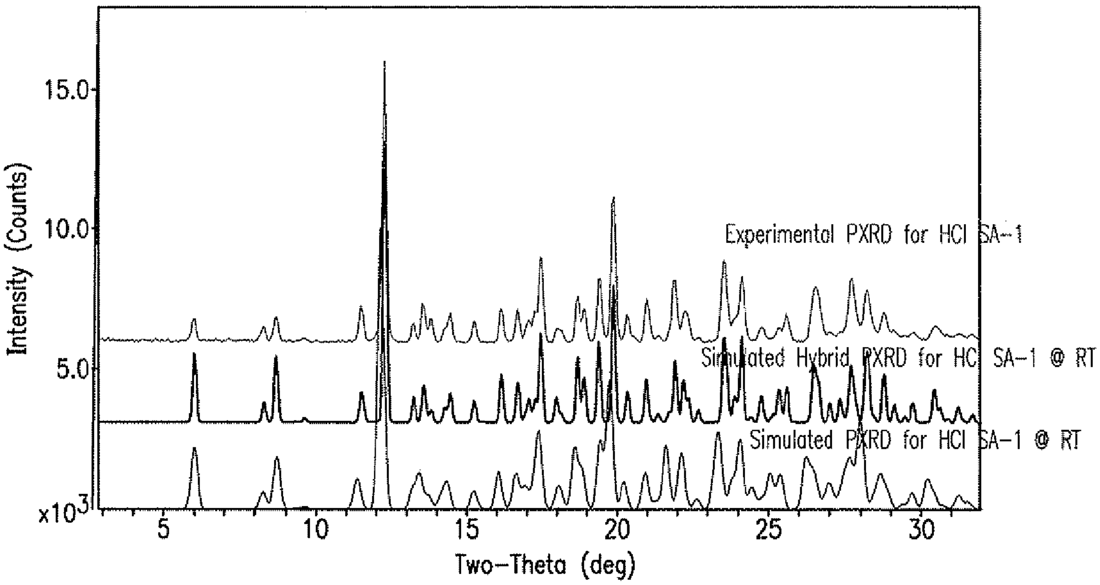
FIG. 1 shows the observed and calculated (room temperature) powder X-ray diffraction patterns (CuKα λ=1.5418 Å) of Form HCl:SA-1 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.

In a first aspect, the present invention provides compounds of Formula (I):

(I)

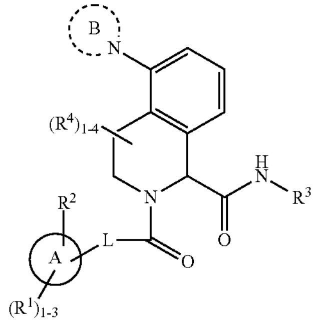

or stereoisomers, tautomers, pharmaceutically acceptable salts, or solvates thereof, wherein:

ring A is $C_{3-6}$ carbocycle;

ring B is 4- to 7-membered heterocycle containing carbon atoms and 0-3 additional heteroatoms selected from the group consisting of N, $NR^6$, O, and $S(O)_p$; optionally, ring B forms a fused ring or spiro ring with a 4- to 7-membered heterocycle containing carbon atoms and 1-3 heteroatoms selected from the group consisting of $NR^6$, O, and $S(O)_p$; ring B, including the fused ring or spiro ring is substituted with 1-3 $R^5$;

L is selected from the group consisting of: $-CHR^{10}CHR^{10}-$, $-CR^{10}=CR^{10}-$, $-C\equiv C-$, $-CHR^{10}NH-$, $-NHCHR^{10}-$, $-SCH_2-$, $-CH_2S-$, $-SO_2CH_2-$, $-CH_2SO_2-$, $-NHCH_2-$, and $-CH_2NH-$;

$R^1$, at each occurrence, is selected from the group consisting of: H, halo, $C_{1-6}$ alkyl, $C_{1-4}$ alkoxy, $C_{1-4}$ alkylthio, OH, SH, $CHF_2$, $CF_3$, $OCF_3$, CN, $NH_2$, $COC_{1-4}$ alkyl, $CO_2(C_{1-4}$ alkyl), $-CH_2CO_2H$, $-CH_2CO_2(C_{1-4}$ alkyl), $-CH_2NH_2$, $-CONH_2$, $-CONH(C_{1-4}$ alkyl), $-NHCO(C_{1-4}$ alkyl), $-NHCO_2(C_{1-4}$ alkyl), $-NHSO_2(C_{1-4}$ alkyl), and $-SO_2NH_2$, and $-C(=NH)NH_2$;

$R^2$ is selected from the group consisting of: H, halo, CN, OH, $C_{1-6}$ alkyl, $C_{1-4}$ alkoxy, $C_{1-6}$haloalkyl, $C_{1-6}$haloalkoxy, $CO(C_{1-4}$ alkyl), $CONH_2$, $CO_2H$, $CH_2NH_2$, and a 5- to 7-membered heterocycle comprising carbon atoms and 1-4 heteroatoms selected from N, $NR^c$, O, and $S(O)_p$, wherein said heterocycle is substituted with 0-2 $R^{2a}$;

$R^{2a}$, at each occurrence, is selected from the group consisting of: H, halo, $C_{1-4}$ alkyl, $-CH_2OH$, $C_{1-4}$ alkoxy, OH, $CF_3$, $OCF_3$, CN, $NH_2$, $CO_2H$, $CO_2(C_{1-4}$ alkyl), $CO(C_{1-4}$ alkyl), $-CONH_2$, $-CH_2OH$, $-CH_2OC_{1-4}$ alkyl, $-CH_2NH_2-$, $CONH(C_{1-4}$ alkyl), $-CON(C_{1-4}$ alkyl$)_2$, $-SO_2(C_{1-4}$ alkyl), $-SO_2NH_2$, $-SO_2NH(C_{1-4}$ alkyl), and $-SO_2N(C_{1-4}$ alkyl$)_2$;

$R^3$ is selected from the group consisting of: $C_{1-6}$ alkyl substituted with 1-3 $R^{3a}$, $-(CH_2)_n-C_{3-10}$ carbocycle substituted with 0-3 $R^{3a}$ or $-(CH_2)_n$-5-10 membered heterocycle containing carbon atoms and 1-4 heteroatoms selected from the group consisting of N, $NR^7$, O, and $S(O)_p$; wherein said heterocycle is substituted with 0-3 $R^{3a}$;

$R^{3a}$, at each occurrence, is selected from the group consisting of: =O, halo, $C_{1-4}$ alkyl, OH, $C_{1-4}$ alkoxy, CN, $NH_2$, $CO_2H$, $CO_2(C_{1-4}$ alkyl), $CONH_2$, $CONH(C_{1-6}$ alkyl), $CON(C_{1-4}$ alkyl$)_2$, $-CONH-C_{1-4}$ alkylene-$CO_2(C_{1-4}$ alkyl), $-CONHCO_2C_{1-4}$ alkyl, $-CONH-C_{1-4}$ alkylene-$NHCO(C_{1-4}$ alkyl), $-CONH-C_{1-4}$ alkylene-$CONH_2$, $-NHCOC_{1-4}$ alkyl, $-NHCO_2(C_{1-4}$ alkyl), $-C_{1-4}$ alkylene-$NHCO_2C_{1-4}$ alkyl, $R^f$, $CONHR^f$, and $-CO_2R^f$;

$R^4$, at each occurrence, is selected from the group consisting of: H, halo and $C_{1-4}$ alkyl;

$R^5$, at each occurrence, is selected from the group consisting of: H, =O, halo, $C_{1-4}$ alkyl, OH, CN, $NH_2$, $-N(C_{1-4}$ alkyl$)_2$, $NO_2$, $C_{1-4}$ alkoxy, $-OCO(C_{1-4}$ alkyl), $-O-C_{1-4}$ alkylene-$O(C_{1-4}$ alkyl), $-O-C_{1-4}$ alkylene-$N(C_{1-4}$ alkyl$)_2$, $-CO_2H$, $-CO_2(C_{1-4}$ alkyl), $-CONH_2$, $-(CH_2)_2CONH_2$, $-CONR^9(C_{1-4}$ alkyl), $-CONR^9-C_{1-4}$ alkylene-$O(C_{1-4}$ alkyl), $-CON(C_{1-4}$ alkyl$)_2$, $-CONR^9-C_{1-4}$ alkylene-$N(C_{1-4}$ alkyl$)_2$, $-CON(C_{1-4}$ alkyl)-$C_{1-4}$ alkylene-$O(C_{1-4}$ alkyl), $-CONR^9-C_{1-4}$ alkylene-$CO_2(C_{1-4}$ alkyl), $-NR^9COC_{1-4}$ alkyl, $-NR^9CO_2C_{1-4}$ alkyl, $-NR^9CONH(C_{1-4}$ alkyl), $-NR^9CONR^9-C_{1-4}$ alkylene-$CO_2C_{1-4}$ alkyl, $-NR^9-C_{1-4}$ alkylene-$N(C_{1-4}$ alkyl$)_2$, $R^8$, $-OR^8$, $-O-C_{1-4}$ alkylene-$R^8$, $-COR^8$, $-CO_2R^8$, $-CONR^9R^8$, $-NR^9COR^8$, $-NR^9CO_2R^8$, and $-NR^9CONR^9R^8$;

$R^6$ is selected from the group consisting of: H, $C_{1-4}$ alkyl, $-CO_2(C_{1-4}$ alkyl), $-CO(C_{1-4}$ alkyl), $-CONH_2$, $-CO-C_{1-4}$ alkylene-$N(C_{1-4}$ alkyl$)_2$, $-(CH_2)_2N(C_{1-4}$ alkyl$)_2$, $-CONR^9(C_{1-4}$ alkyl), $-CONR^9-C_{1-4}$ alkylene-$O(C_{1-4}$ alkyl), $-CONR^9-C_{1-4}$ alkylene-$N(C_{1-4}$ alkyl$)_2$, $-CONR^9-C_{1-4}$ alkylene-$CO_2(C_{1-4}$ alkyl), $-CON(C_{1-4}$ alkyl$)_2$, $R^8$, $-COR^8$, $-CO_2R^8$, and $-CONR^9R^8$;

$R^7$, at each occurrence, is selected from the group consisting of: H, $C_{1-4}$ alkyl, $COC_{1-4}$ alkyl, $CO_2(C_{1-4}$ alkyl), $CO_2Bn$, $-CONH-C_{1-4}$ alkylene-$CO_2C_{1-4}$ alkyl, phenyl, benzyl, and $-CO_2-C_{1-4}$ alkylene-aryl;

$R^8$, at each occurrence, is selected from the group consisting of: $-(CH_2)_n-C_{3-10}$ carbocycle substituted with 0-3 $R^e$ and $-(CH_2)_n$-5-10 membered heterocycle containing carbon atoms and 1-4 heteroatoms selected from the group consisting of N, $NR_d$, O, and $S(O)_p$; wherein said carbocycle and heterocycle are optionally substituted with =O;

$R^9$, at each occurrence, is selected from the group consisting of: H and $C_{1-4}$ alkyl;

$R^{10}$, at each occurrence, is selected from the group consisting of: H, halo, OH, and $C_{1-4}$ alkyl;

$R^c$ is, independently at each occurrence, selected from the group consisting of: H, $C_{1-4}$ alkyl, $COC_{1-4}$ alkyl, $CO_2C_{1-4}$ alkyl, and $CO_2Bn$;

$R^d$ is, independently at each occurrence, selected from the group consisting of: H, $C_{1-4}$ alkyl, $CO(C_{1-4}$ alkyl), $COCF_3$, $CO_2(C_{1-4}$ alkyl), —CONH—$C_{1-4}$ alkylene-$CO_2C_{1-4}$ alkyl, $CO_2Bn$, $R^f$, and $CONHR^f$;

$R^e$ is, independently at each occurrence, selected from the group consisting of: =O, halo, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —CONHPh, —$CON(C_{1-4}$ alkyl$)_2$, —CONH—$C_{1-4}$ alkylene-O($C_{1-4}$ alkyl), —CONH—$C_{1-4}$ alkylene-N($C_{1-4}$ alkyl$)_2$, —CONH—$C_{1-4}$ alkylene-$CO_2(C_{1-4}$ alkyl), —$NHCO_2(C_{1-4}$ alkyl), $R^f$, $COR^f$, $CO_2R^f$ and $CONHR^f$;

$R^f$ is, independently at each occurrence, selected from the group consisting of: —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of N, $NR^c$, O, and $S(O)_p$; wherein each ring moiety is substituted with 0-2 $R^g$;

$R^g$ is, independently at each occurrence, selected from the group consisting of: =O, halo, $C_{1-4}$ alkyl, OH, $C_{1-4}$ alkoxy, and $NHCO(C_{1-4}$ alkyl);

n, at each occurrence, is selected from 0, 1, 2, 3, and 4; and p, at each occurrence, is selected from 0, 1, and 2.

In a second aspect, the present invention provides compounds of Formula (I) or stereoisomers, tautomers, pharmaceutically acceptable salts thereof, within the scope of the first aspect, wherein:

ring A is $C_{3-6}$ carbocycle;

ring B is 4- to 7-membered heterocycle containing carbon atoms and 0-3 additional heteroatoms selected from the group consisting of N, $NR^6$, O, and $S(O)_p$; optionally, ring B forms a fused ring or spiro ring with a 4- to 7-membered heterocycle containing carbon atoms and 1-3 heteroatoms selected from the group consisting of $NR^6$, O, and $S(O)_p$; ring B, including the fused ring or spiro ring is substituted with 1-3 $R^5$;

L is selected from the group consisting of: a bond, —$CHR^{10}CHR^{10}$—, —$CR^{10}$=$CR^{10}$—, and —C≡C—;

$R^1$, at each occurrence, is selected from the group consisting of: H, halo, $C_{1-2}$ alkyl, —O($C_{1-4}$ alkyl), CN, —$CH_2NH_2$, and —C(=NH)$NH_2$;

$R^2$ is independently selected from the group consisting of: H, halo, CN, OH $C_{1-6}$ alkyl, $C_{1-4}$ alkoxy, $C_{1-6}$haloalkyl, $C_{1-6}$haloalkoxy, $CO(C_{1-4}$ alkyl), $CONH_2$, $CO_2H$ and a 5- to 7-membered heterocycle comprising carbon atoms and 1-4 heteroatoms selected from N, NH, N($C_{1-4}$ alkyl), O, and $S(O)_p$, wherein said heterocycle is substituted with 1-2 $R^{2a}$;

$R^{2a}$, at each occurrence, is selected from the group consisting of: H, halo, $C_{1-4}$ alkyl, $CO_2H$, —$CO_2(C_{1-4}$ alkyl), —$CONH_2$, —$CH_2OH$, —$CH_2OC_{1-4}$ alkyl, and —$CH_2NH_2$;

$R^3$ is selected from the group consisting of: $C_{1-6}$ alkyl substituted with 1-3 $R^{3a}$, $C_{3-10}$ carbocycle substituted with 1-3 $R^{3a}$, and 5-10 membered heterocycle containing carbon atoms and 1-4 heteroatoms selected from the group consisting of N, $NR^7$, O, and $S(O)_p$; wherein said heterocycle is substituted with 1-3 $R^{3a}$;

$R^{3a}$, at each occurrence, is selected from the group consisting of: H, halo, $C_{1-4}$ alkyl, —OH, $C_{1-4}$ alkoxy, —CN, —$NH_2$, —$NH(C_{1-4}$ alkyl), —$N(C_{1-4}$ alkyl$)_2$, —$CO_2H$, —$CH_2CO_2H$, —$CO_2(C_{1-4}$ alkyl), —$CO_2$—$C_{1-4}$ alkylene-O ($C_{1-4}$ alkyl), —$CO_2$—$C_{1-4}$ alkylene-N($C_{1-4}$ alkyl$)_2$, —$CONH_2$, —$CONH(C_{1-6}$ alkyl), —$CON(C_{1-4}$ alkyl$)_2$, —CONH—$C_{1-4}$ alkylene-$CO_2(C_{1-4}$ alkyl), —$CONHCO_2C_{1-4}$ alkyl, —CONH—$C_{1-4}$ alkylene-NHCO ($C_{1-4}$ alkyl), —CONH—$C_{1-4}$ alkylene-$CONH_2$, —$NHCOC_{1-4}$ alkyl, —$NHCO_2(C_{1-4}$ alkyl), $R^8$, —$CONHR^8$, and —$CO_2R^8$;

$R^4$, at each occurrence, is selected from the group consisting of: H, halo, and $C_{1-4}$ alkyl;

$R^5$, at each occurrence, is selected from the group consisting of: H, =O, halo, $C_{1-4}$ alkyl, OH, CN, $NH_2$, —$N(C_{1-4}$ alkyl$)_2$, $NO_2$, $C_{1-4}$ alkoxy, —$OCO(C_{1-4}$ alkyl), —O—$C_{1-4}$ alkylene-O($C_{1-4}$ alkyl), —O—$C_{1-4}$ alkylene-N($C_{1-4}$ alkyl$)_2$, —$CO_2H$, —$CO_2(C_{1-4}$ alkyl), —$CONH_2$, —$(CH_2)_2CONH_2$, —$CONR^9(C_{1-4}$ alkyl), —$CONR^9$—$C_{1-4}$ alkylene-O($C_{1-4}$ alkyl), —$CON(C_{1-4}$ alkyl$)_2$, —$CONR^9$—$C_{1-4}$ alkylene-N ($C_{1-4}$ alkyl$)_2$, —$CON(C_{1-4}$ alkyl)-$C_{1-4}$ alkylene-O($C_{1-4}$ alkyl), —$CONR^9$—$C_{1-4}$ alkylene-$CO_2(C_{1-4}$ alkyl), —$NR^9COC_{1-4}$ alkyl, —$NR^9CO_2C_{1-4}$ alkyl, —$NR^9CONH$ ($C_{1-4}$ alkyl), —$NR^9CONR^9$—$C_{1-4}$ alkylene-$CO_2C_{1-4}$ alkyl, —$NR^9$—$C_{1-4}$ alkylene-N($C_{1-4}$ alkyl$)_2$, $R^8$, —$OR^8$, —O—$C_{1-4}$ alkylene-$R^8$, —$COR^8$, —$CO_2R^8$, —$CONR^9R^8$, —$NR^9COR^8$, —$NR^9CO_2R^8$, and —$NR^9CONR^9R^8$;

$R^6$ is selected from the group consisting of: H, $C_{1-4}$ alkyl, —$CO_2(C_{1-4}$ alkyl), —$CO(C_{1-4}$ alkyl), —$CONH_2$, —CO—$C_{1-4}$ alkylene-N($C_{1-4}$ alkyl$)_2$, —$(CH_2)_2N(C_{1-4}$ alkyl$)_2$, —$CONR^9(C_{1-4}$ alkyl), —$CONR^9$—$C_{1-4}$ alkylene-O($C_{1-4}$ alkyl), —$CONR^9$—$C_{1-4}$ alkylene-N($C_{1-4}$ alkyl$)_2$, —$CONR^9$—$C_{1-4}$ alkylene-$CO_2(C_{1-4}$ alkyl), —$CON(C_{1-4}$ alkyl$)_2$, $R^8$, —$COR^8$, —$CO_2R^8$, and —$CONR^9R^8$;

$R^7$, at each occurrence, is selected from the group consisting of: H, $C_{1-4}$ alkyl, —$CO_2(C_{1-4}$ alkyl), and —$CO_2$—$C_{1-4}$ alkylene-aryl;

$R^8$, at each occurrence, is selected from the group consisting of: —$(CH_2)_n$—$C_{3-10}$ carbocycle and —$(CH_2)_n$-5-10 membered heterocycle containing carbon atoms and 1-4 heteroatoms selected from the group consisting of N, NH, N($C_{1-4}$ alkyl), O, and $S(O)_p$; wherein said carbocycle and heterocycle are substituted with =O;

$R^9$, at each occurrence, is selected from the group consisting of: H and $C_{1-4}$alkyl;

$R^{10}$, at each occurrence, is selected from the group consisting of: H and F;

n, at each occurrence, is selected from 0, 1, 2, 3, and 4; and p, at each occurrence, is selected from 0, 1, and 2.

In a third aspect, the present invention includes compounds of Formula (II):

(II)

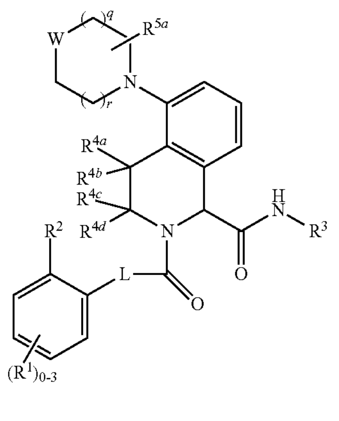

or stereoisomers, tautomers, pharmaceutically acceptable salts, or solvates thereof, within the scope of the second aspect, wherein:

W is selected from the group consisting of $CR^{5b}R^{5c}$, O, $S(O)_p$, and $NR^6$;

$R^{4a}$, $R^{4b}$, $R^{4c}$, and $R^{4d}$ are independently selected from the group consisting of: H, F, and $C_{1-4}$ alkyl;

$R^{5a}$ is selected from the group consisting of: H and =O;

$R^{5b}$ and $R^{5c}$ are independently selected from the group consisting of: H, halo, $C_{1-4}$ alkyl, OH, CN, $NH_2$, —N($C_{1-4}$ alkyl)$_2$, $C_{1-4}$ alkoxy, —OCO—$C_{1-4}$ alkyl, —O—$C_{1-4}$alkylene-N($C_{1-4}$ alkyl)$_2$, —O—$C_{1-4}$alkylene-O($C_{1-4}$ alkyl), —$CO_2$H, —$CO_2$($C_{1-4}$ alkyl), —$CONH_2$, —$CONR^9$($C_{1-4}$ alkyl), —CON($C_{1-4}$ alkyl)$_2$, $R^8$, —$OR^8$, —$COR^8$, and —$CO_2R^8$;

optionally, $R^{5b}$ and $R^{5c}$ together with the carbon atom to which they are attached form a 4-7 membered heterocyclic ring containing carbon atoms and 1-4 heteroatoms selected from the group consisting of N, $NR^6$, O, and $S(O)_p$; wherein said heterocycle is unsubstituted or substituted with =O.

q, at each occurrence, is selected from 0, 1, and 2; and r, at each occurrence, is selected from 0, 1, and 2.

In a fourth aspect, the present invention includes compounds of Formula (III):

(III)

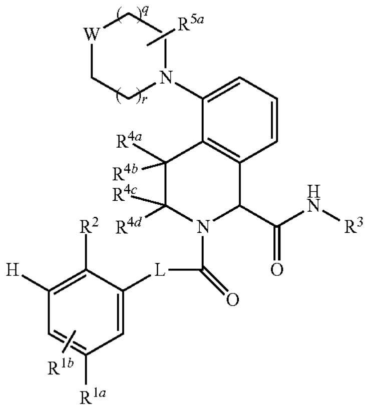

or stereoisomers, tautomers, pharmaceutically acceptable salts, or solvates thereof, within the scope of the third aspect, wherein:

$R^{1a}$ is selected from the group consisting of: H, halo, $C_{1-2}$ alkyl, and methoxy;

$R^{1b}$ is selected from the group consisting of: H and halo;

$R^2$ is independently selected from the group consisting of: H, F, CN, OH, $C_{1-4}$ alkoxy, —$CHF_2$, —$CF_3$, —$CH_2NH_2$, —$OCHF_2$, —CO($C_{1-4}$ alkyl), —$CONH_2$, —COOH, triazole substituted with $R^{2a}$, and tetrazole substituted with $R^{2a}$;

$R^3$ is selected from the group consisting of: phenyl substituted with 1-2 $R^{3a}$, $C_{3-6}$ cycloalkyl substituted with 1-2 $R^{3a}$, heterocycle substituted with 1-2 $R^{3a}$; wherein said heterocycle is selected from the group consisting of: piperidinyl, pyridyl, indolyl, and indazolyl.

In a fifth aspect, the present invention includes compounds of Formula (IV):

(IV)

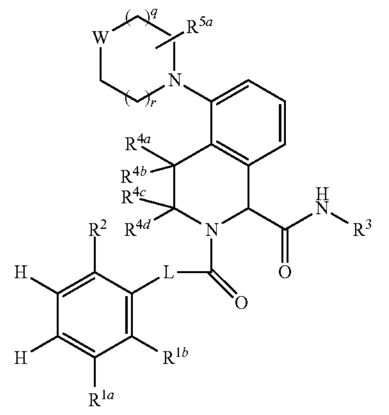

or stereoisomers, tautomers, pharmaceutically acceptable salts, or solvates thereof, within the scope of the fourth aspect, wherein:

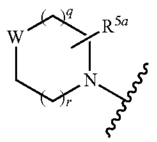

is selected from the group consisting of:

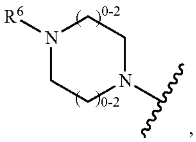
,
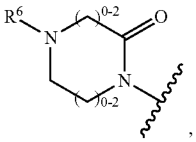
,
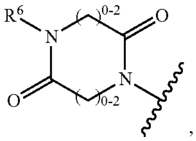
,
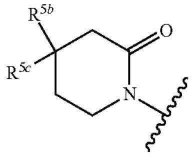
,
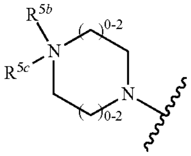
,
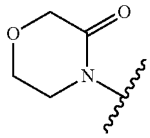
,
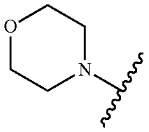
,
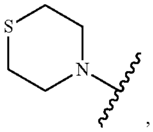
, and
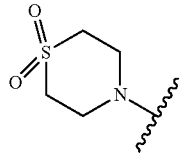

$R^3$ is selected from the group consisting of: phenyl substituted with 1-2 $R^{3a}$, pyridyl substituted with 1-2 $R^{3a}$, $C_{3-6}$ cycloalkyl substituted with 1-2 $R^{3a}$,

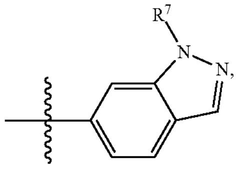

and

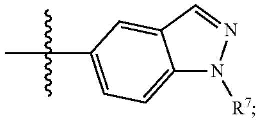

$R^7$ is selected from the group consisting of: H and $C_{1-4}$ alkyl.

In a sixth aspect, the present invention includes compounds of Formula (V):

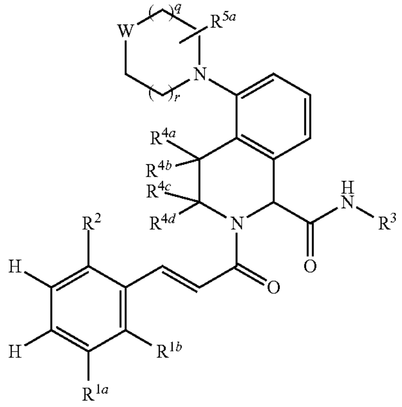

(V)

or stereoisomers, tautomers, pharmaceutically acceptable salts, or solvates thereof, within the scope of the fifth aspect, wherein:

$R^3$ is selected from the group consisting of: phenyl substituted with 1-2 $R^{3a}$ and pyridyl substituted with 1-2 $R^{3a}$;

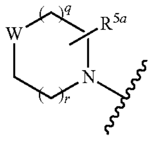

is selected from the group consisting of:

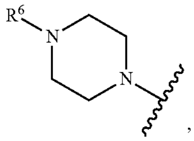

,

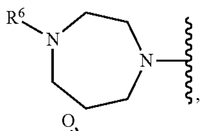

,

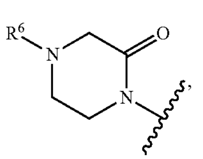

,

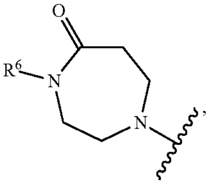

,

-continued

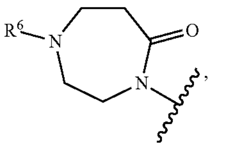

,

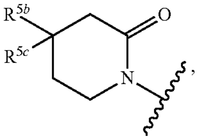

,

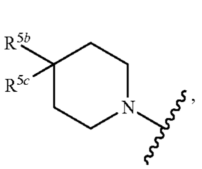

,

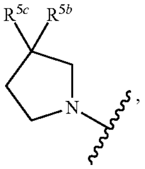

,

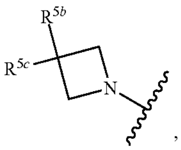

,

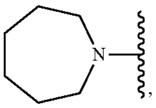

,

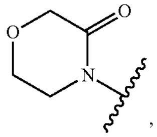

,

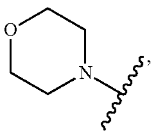

,

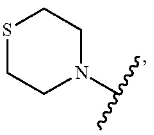

, and

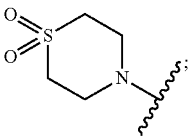

;

$R^{3a}$, at each occurrence, is selected from the group consisting of: H, halo, $C_{1-4}$ alkyl, OH, $C_{1-4}$ alkoxy, CN, $NH_2$, $—CO_2H$, $—CH_2CO_2H$, $—CO_2(C_{1-4}$ alkyl), $—CO_2(CH_2)_{1-2}O(C_{1-4}$ alkyl), $—CO_2(CH_2)_{1-2}CON(C_{1-4}$ alkyl$)_2$, $—CONH_2$, $CONH(C_{1-4}$ alkyl), $—CON(C_{1-4}$ alkyl$)_2$, $—NHCO_2(C_{1-4}$ alkyl), $R^8$, $—CONHR^8$, and $—CO_2R^8$ $R^{5b}$ and $R^{5c}$ are independently selected from the group consisting of: H, $C_{1-4}$ alkyl, OH, CN, $NH_2$, $—N(C_{1-4}$ alkyl$)_2$, $C_{1-4}$ alkoxy, $—OCO—C_{1-4}$ alkyl, $—CO_2H$, $—CO_2(C_{1-4}$ alkyl), $—CONH_2$, $—CONR^9(C_{1-4}$ alkyl), $—CON(C_{1-4}$ alkyl$)_2$, $R^8$, $—OR^8$, $—COR^8$, and $—CO_2R^8$;

optionally, $R^{5b}$ and $R^{5c}$ together with the carbon atom to which they are both attached form a 5-6 membered heterocyclic ring containing carbon atoms and 1-4 heteroatoms selected from the group consisting of N, $NR^6$, O, and $S(O)_p$; wherein said heterocycle is unsubstituted or substituted with =O; and $R^6$ is selected from the group consisting of: H, $C_{1-4}$ alkyl, $—CO_2(C_{1-4}$ alkyl), $—CO(C_{1-4}$ alkyl), $—CO—C_{1-4}$ alkylene-$N(C_{1-4}$ alkyl$)_2$, $—CONH_2$, $—(CH_2)_2N(C_{1-4}$ alkyl$)_2$, $—CONH(C_{1-4}$ alkyl), $—CONH—C_{1-4}$ alkylene-$O(C_{1-4}$ alkyl), $—CONH—C_{1-4}$ alkylene-$N(C_{1-4}$ alkyl$)_2$, $—CONH—C_{1-4}$ alkylene-$CO_2(C_{1-4}$ alkyl), $—CONH(C_{1-4}$ alkyl), $—CON(C_{1-4}$ alkyl$)_2$, $R^8$, $—COR^8$, and $—CO_2R^8$.

In a seventh aspect, the present invention includes compounds of Formula (VI):

(VI)

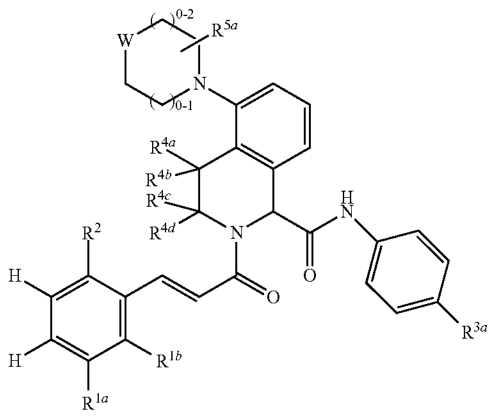

or stereoisomers, tautomers, pharmaceutically acceptable salts thereof, within the scope of the sixth aspect, wherein:

$R^{1b}$ is independently selected from the group consisting of: H and F;

$R^{3a}$ is selected from the group consisting of: H, halo, CN, $CO_2H$, —$CO_2(C_{1-4}$ alkyl), —$CO_2(CH_2)_{1-2}O(C_{1-4}$ alkyl), —$CO_2(CH_2)_{1-2}CON(C_{1-4}$ alkyl$)_2$, —$CONH_2$, —CONH ($C_{1-4}$ alkyl), —$NHCO_2(C_{1-4}$ alkyl), —$CO_2(C_{3-6}$ cycloalkyl), —$CO_2(CH_2)_{1-2}$Ph, and —$CO_2(CH_2)_{1-2}$triazole.

In an eighth aspect, the present invention includes compounds of Formula (VI), or stereoisomers, tautomers, pharmaceutically acceptable salts, or solvates thereof, within the scope of the seventh aspect, wherein:

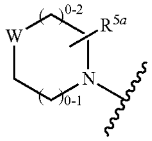

is selected from the group consisting of:

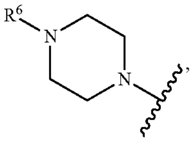, 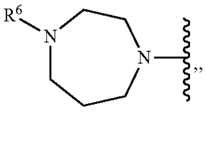,

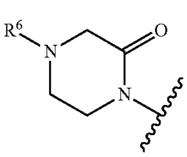, 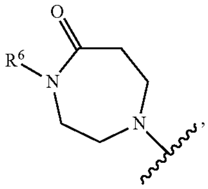,

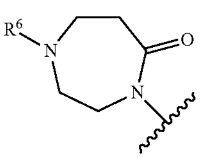 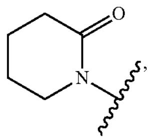, 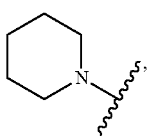,

-continued

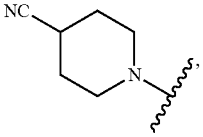, 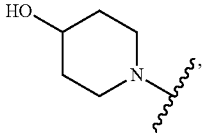,

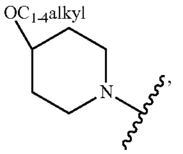, 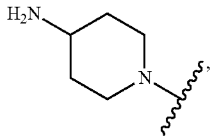,

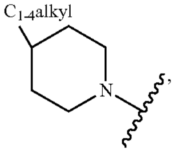, 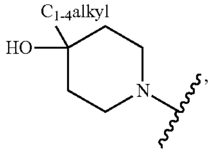,

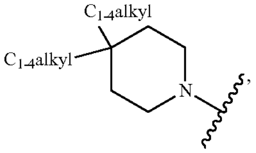, 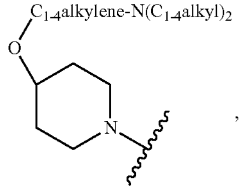,

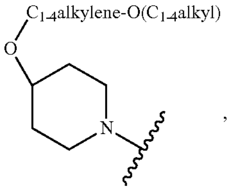, 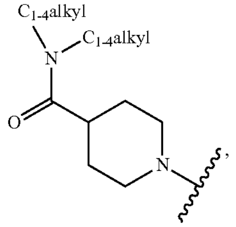,

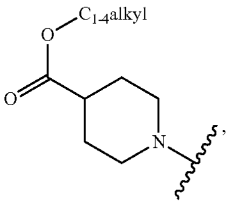,

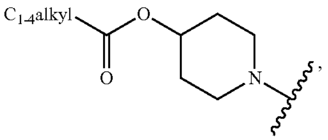,

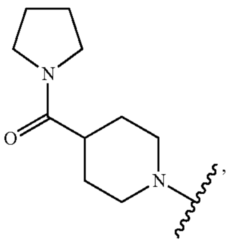, 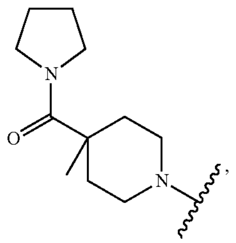,

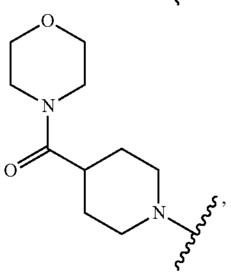, 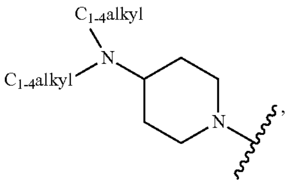,

-continued

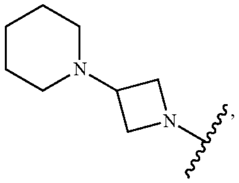
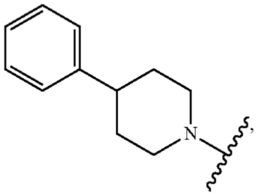
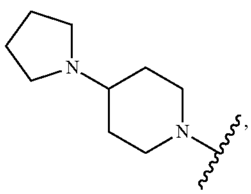
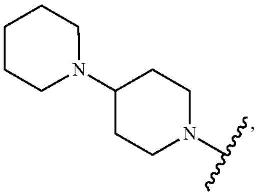
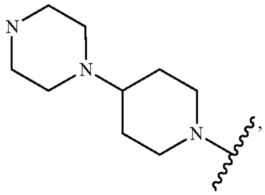
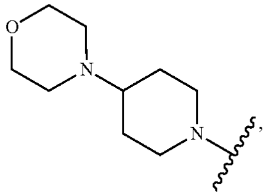
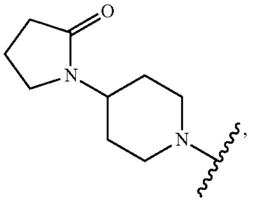
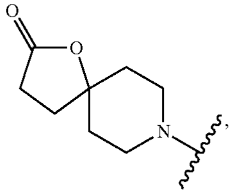
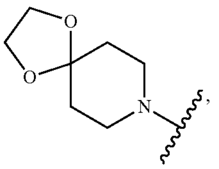
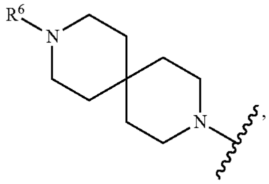
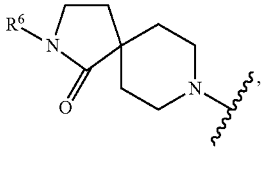
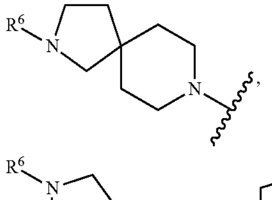
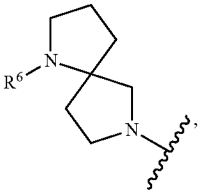
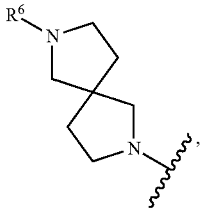
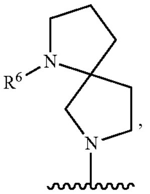
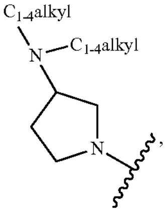

-continued

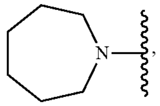
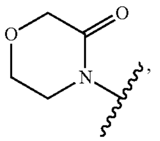
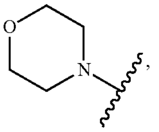
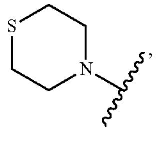
and
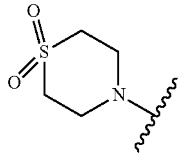

$R^{3a}$ is independently selected from the group consisting of: H, F, Cl, CN, $CO_2H$, —$CO_2Me$, —$CO_2Et$, —$CO_2$(i-Pr), —$CO_2$(t-Bu), —$CO_2$(n-Bu), —$CO_2$(i-Bu), —$CO_2(CH_2)_2$OMe, —$CO_2CH_2CON(Me)_2$, —$NHCO_2Me$, —$CO_2CH_2$(phenyl), —$CO_2(C_{3-6}$ cycloalkyl), and —$CO_2(CH_2)_2$-triazole; and $R^6$ is selected from the group consisting of: H, $C_{1-4}$ alkyl, —$CO_2(C_{1-4}$ alkyl), —$CO(C_{1-4}$ alkyl), —$COCH_2N(C_{1-4}$ alkyl$)_2$, —$(CH_2)_{1-2}N(C_{1-4}$ alkyl$)_2$, —$CONH(C_{1-4}$ alkyl), —CONH—$C_{1-4}$ alkylene-O($C_{1-4}$ alkyl), —CONH—$C_{1-4}$ alkylene-N($C_{1-4}$ alkyl$)_2$, —CONH—$C_{1-4}$ alkylene-$CO_2$($C_{1-4}$ alkyl), —$CH_2Ph$, and —$CO_2$—$C_{1-4}$ alkylene-Ph.

In a ninth aspect, the present invention includes compounds of Formula (VII):

(VII)

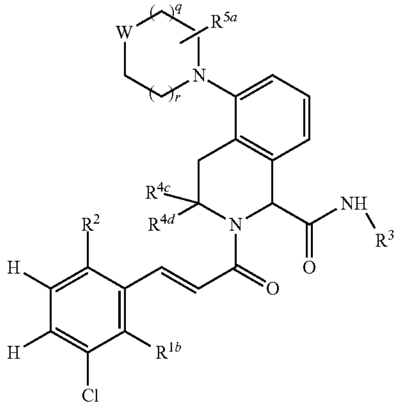

or stereoisomers, tautomers, pharmaceutically acceptable salts, or solvates thereof, within the scope of the second aspect, wherein:

$R^{1b}$ is selected from the group consisting of: H and F;

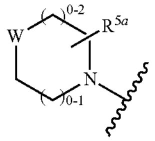

is selected from the group consisting of:

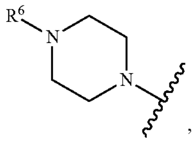,
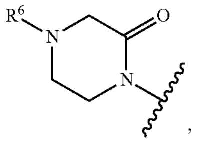,
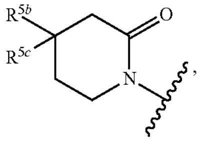,
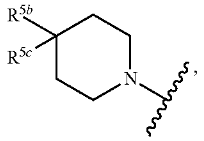,
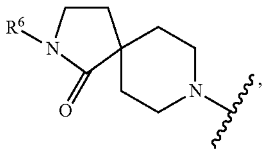,
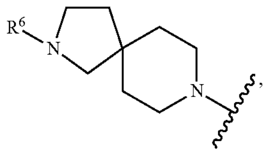,
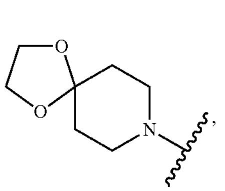,
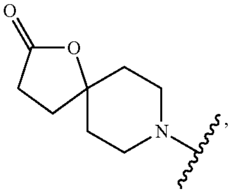,
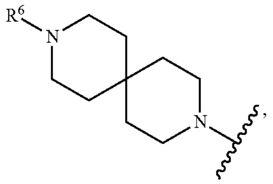,
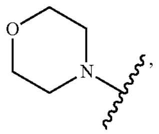,
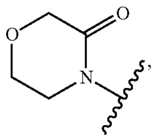,
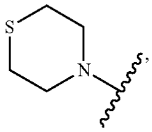,
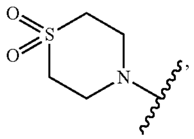,
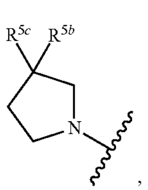,
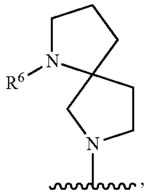,
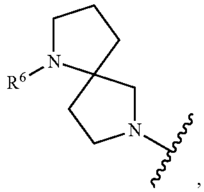,
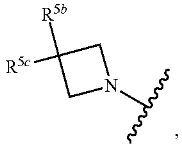,
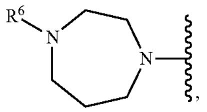,
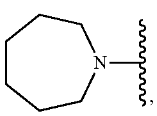, and
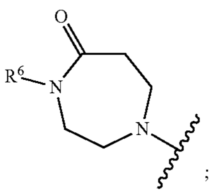;

$R^2$ is selected from the group consisting of: H, F, CN, COMe, OH, OMe, $OCHF_2$, $CHF_2$, $CF_3$, and tetrazole;

$R^3$ is selected from the group consisting of: phenyl substituted with 1-2 $R^{3a}$, cyclohexyl,

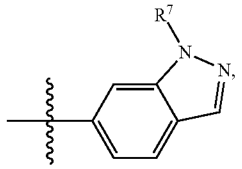, and
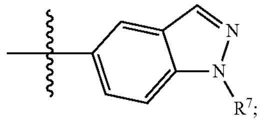;

$R^{3a}$ is independently selected from the group consisting of: H, F, Cl, CN, $CO_2H$, —$CH_2CO_2H$, $CO_2Me$, —$CO_2Et$, —$CO_2$(i-Pr), —$CO_2$(t-Bu), —$CO_2$(n-Bu), —$CO_2$(i-Bu), —$CO_2(CH_2)_2OMe$, —$CO_2CH_2CON(Me)_2$, —$NHCO_2Me$, —$CO_2(CH_2)_2$-triazole, and —$CO_2$(cyclopentyl);

$R^{4c}$ and $R_{4d}$ are independently selected from the group consisting of: H and Me;

$R^{5b}$ and $R^{5c}$ are, independently selected from the group consisting of: H, F, Me, Et, i-propyl, CN, OH, —OMe, —$CO_2Me$, —$CO_2Et$, —$CON(Me)_2$, $NH_2$, —$N(Me)_2$, —$O(CH_2)N(Me)_2$, —$O(CH_2)OMe$,

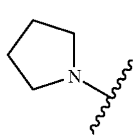,
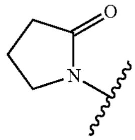,
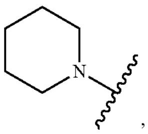,
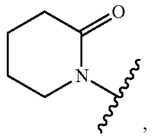,
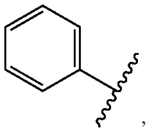,
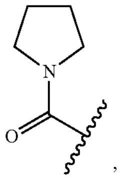,
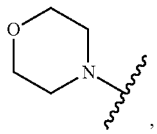,
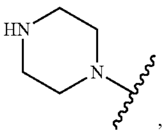, and
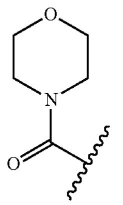;

$R^6$ is selected from the group consisting of: H, Me, —$CO_2Me$, —$CO_2$(t-butyl), —COMe, —CONHMe, —$CONH(CH_2)_2CO_2Et$, $CONH(CH_2)_2N(Me)_2$, —$CO_2CH_2Ph$, —$(CH_2)_2N(Me)_2$, and —$CH_2Ph$; and $R^7$ is selected from the group consisting of: H and Me;

q, at each occurrence, is selected from 0, 1, and 2; and r, at each occurrence, is selected from 0, 1, and 2.

In a tenth aspect, the present invention includes compounds of Formula (VIII):

(VIII)

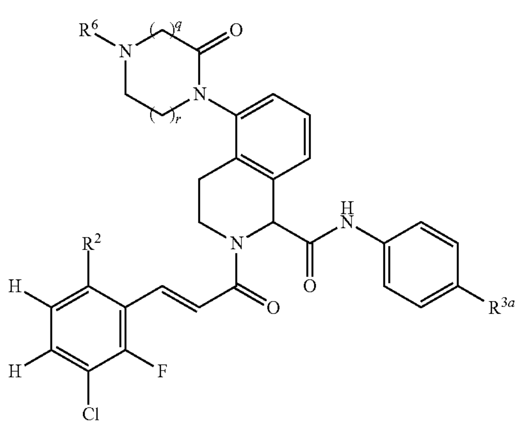

or stereoisomers, tautomers, pharmaceutically acceptable salt thereof, within the scope of the ninth aspect wherein:

$R^2$ is selected from the group consisting of: H, F, CN, COMe, OH, OMe, $OCHF_2$, $CHF_2$, $CF_3$, and tetrazole;

$R^{3a}$ is selected from the group consisting of: H, F, Cl, CN, $CO_2H$, $-CH_2CO_2H$, $CO_2Me$, $-CO_2Et$, $-CO_2$(i-Pr), $-CO_2$(t-Bu), $-CO_2$(n-Bu), $-CO_2$(i-Bu), and $-NHCO_2Me$;

$R^6$ is selected from the group consisting of: H, Me, $-CO_2Me$, $-CO_2$(t-butyl), —COMe, and —CONHMe;

q is 1 or 2; and r is 1 or 2.

In an eleventh aspect, the present invention includes compounds of Formula (VIII):

(VIII)

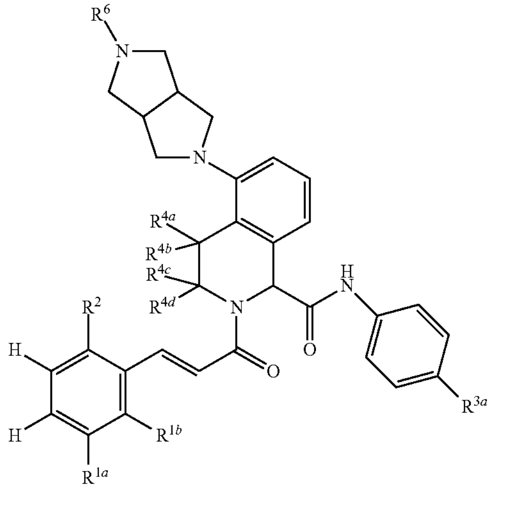

or stereoisomers, tautomers, pharmaceutically acceptable salts thereof, wherein:

$R^{1a}$ is selected from the group consisting of: H, Cl, $C_{1-2}$ alkyl, and methoxy;

$R^{1b}$ is selected from the group consisting of: H and F;

$R^6$ is selected from the group consisting of: H, $C_{1-4}$ alkyl, $-CO(C_{1-4}$ alkyl), $CO_2H$, $-CO_2(C_{1-4}$ alkyl), $-CO(CH_2)_{0-2}NH(C_{1-4}$ alkyl), and $-CO(CH_2)_{0-2}N(C_{1-4}$ alkyl$)_2$;

$R^{3a}$ is selected from the group consisting of: H, F, Cl, CN, $CO_2H$, $-CO_2Et$, and $-CO_2$(t-Bu).

In a twelfth aspect, the present invention includes compounds of Formula (I) or stereoisomers, tautomers, pharmaceutically acceptable salts thereof, within the scope of the first aspect, wherein:

ring B is heteroaryl or bridged heterocycle, each containing carbon atoms and 0-2 additional heteroatoms selected from the group consisting of N, NH, O, and S(O)p, and each substituted with 1-3 $R^5$;

$R^2$ is selected from the group consisting of: H, F, CN, $-CO(C_{1-4}$ alkyl), OH, $-O(C_{1-4}$ alkyl), $-OCHF_2$, $-CHF_2$, $-CF_3$, triazole, and tetrazole, wherein said triazole and tetrazole are substituted with 0-2 $R^{2a}$; and $R^5$, at each occurrence, is selected from the group consisting of: H, =O, halo, $C_{1-4}$ alkyl, OH, CN, $NH_2$, $-N(C_{1-4}$ alkyl$)_2$, $C_{1-4}$ alkoxy, $-CO_2H$, $-CO_2(C_{1-4}$ alkyl), $-CONH_2$, $-CONR^9(C_{1-4}$ alkyl), $-CON(C_{1-4}$ alkyl$)_2$, $R^8$, and $-COR^8$.

In another embodiment, ring A is phenyl.

In another embodiment, ring A is cyclohexyl.

In another aspect, ring A is

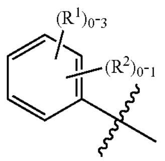

wherein $R^1$ is, independently at each occurrence, selected from the group consisting of: halogen, $C_{1-4}$ alkyl, OH, $C_{1-4}$ alkoxy, $CO(C_{1-4}$ alkyl), CN, $CH_2F$, $CHF_2$, $OCHF_2$, and $-CH_2NHCO_2(C_{1-4}$ alkyl), a 5- to 7-membered heterocycle comprising carbon atoms and 1-4 heteroatoms selected from N, $NR^c$, O, and $S(O)_p$, wherein said heterocycle is substituted with 0-2 $R^{2a}$.

In another aspect, ring A is

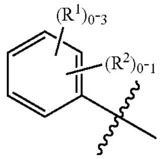

independently selected from the group consisting of:

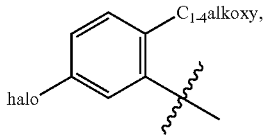

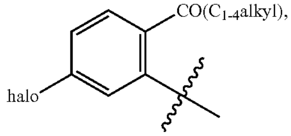

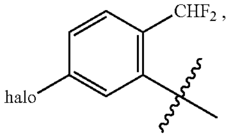

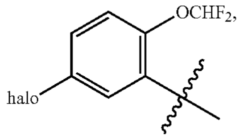

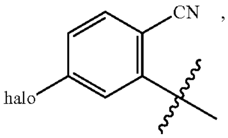

-continued

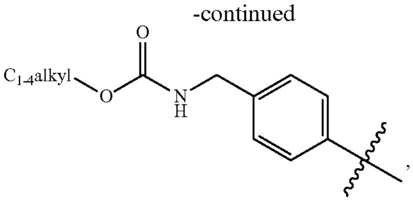

,

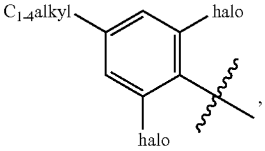

,

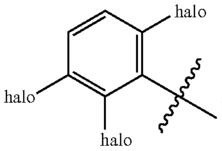

,

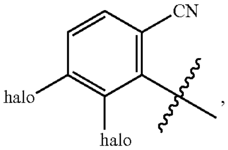

,

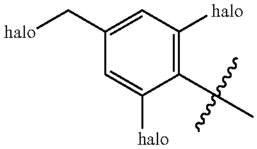

,

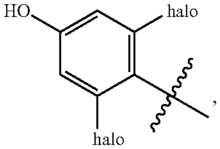

,

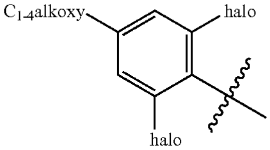

, and

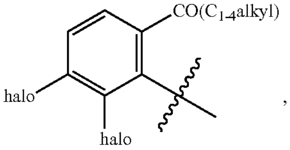

,

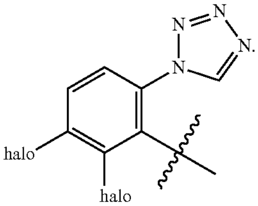

In another embodiment, L is independently selected from the group consisting of: a bond, —$CH_2CH_2$—, —CH═CH—, —C(Me)═CH—, —C≡C—, and —$CH_2NH$—.

In another embodiment, L is independently selected from the group consisting of: a bond, —$CH_2CH_2$—, —CH═CH—, and —C(Me)═CH.

In another embodiment, L is independently selected from the group consisting of: a bond, —$CH_2CH_2$— and —CH═CH—.

In another embodiment, L is —CH═CH—.

In another embodiment, ring B is

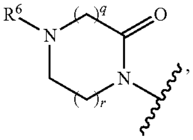

, wherein $R^6$ is methyl or ethyl; q and r are independently selected from 0, 1, and 2.

In another embodiment, ring B is

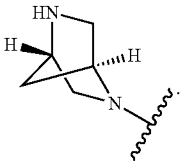

In another embodiment, ring B is substituted pyrazole.

In another embodiment, ring B is

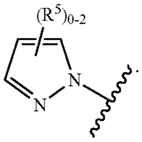

In another embodiment, $R^3$ is $C_{1-4}$ alkyl substituted with $R^{3a}$.

In another embodiment, $R^3$ is phenyl substituted with $R^{3a}$.

In another embodiment, $R^3$ is cyclohexyl substituted with $R^{3a}$.

In another embodiment, $R^3$ is a heterocycle substituted with Ria and selected from:

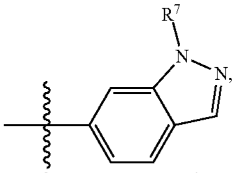

and

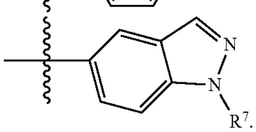

In another embodiment, $R^3$ is

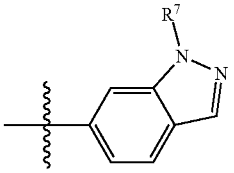

substituted with $R^{3a}$.

In another embodiment, ring B is

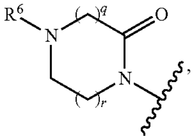

, wherein $R^6$ is methyl or ethyl, q and r are independently an integer selected from 1 and 2; $R^2$ is selected from the group consisting of: H, F, CN, COMe, OH, OMe, $OCHF_2$, $CHF_2$, $CF_3$, and tetrazole; $R^3$ is phenyl substituted with $R^{3a}$, wherein $R^{3a}$ is selected from the group consisting of: H, F, Cl, CN, $CO_2H$, $—CH_2CO_2H$, $CO_2Me$, $—CO_2Et$, $—CO_2$(i-Pr), $—CO_2$(t-Bu), $—CO_2$(n-Bu), $—CO_2$(i-Bu),- and $NHCO_2Me$;

In another aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the exemplified examples or a stereoisomer, a tautomer, a pharmaceutically acceptable salt, or a solvate thereof.

In another embodiment, the compounds of the present invention have Factor XIa Ki values ≤10 μM.

In another embodiment, the compounds of the present invention have Factor XIa Ki values ≤1 μM.

In another embodiment, the compounds of the present invention have Factor XIa Ki values ≤0.5 μM.

In another embodiment, the compounds of the present invention have Factor XIa Ki values ≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof.

Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a second factor XIa inhibitor, an anti-coagulant agent, an anti-platelet agent, a thrombin inhibiting agent, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C═C double bonds, C═N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, Pure and Applied Chemistry, 68, 2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "Co alkyl" or "Co alkylene" is used, it is intended to denote a direct bond.

Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butyryl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in *Hawley's Condensed Chemical Dictionary* (13th Ed.), Lewis, R. J., ed., J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl,5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, Bundgaard, H., ed., Elsevier (1985), and *Methods in Enzymology,* 112:309-396, Widder, K. et al., eds., Academic Press (1985);

b) Bundgaard, H., Chapter 5, "Design and Application of Prodrugs," *A Textbook of Drug Design and Development, pp.* 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, *Medicinal Chemistry: Principles and Practice*, King, F. D., ed. The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); *The Practice of Medicinal Chemistry*, Wermuth, C. G., ed., Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.
Me Methyl
Et Ethyl
Pr Propyl
i-Pr Isopropyl
Bu Butyl
i-Bu Isobutyl
t-Bu tert-butyl
Ph Phenyl
Bn Benzyl
Boc or BOC tert-butyloxycarbonyl
AcOH or HOAc acetic acid
AlCl$_3$ aluminum chloride
AIBN Azobisisobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz Carbobenzyloxy
DCM or CH$_2$Cl$_2$ Dichloromethane
CH$_3$CN or ACN Acetonitrile
CDCl$_3$ deutero-chloroform
CHCl$_3$ Chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1,2 dichloroethane
DEA Diethylamine
Dess-Martin 1,1,1-tris(acetyloxy)-1,1-dihydro-1,2-beniziodoxol-3-(1H)-one
DIC or DIPCDI Diisopropylcarbodiimide
DIEA, DIPEA diisopropylethylamine (Hunig's base)
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et$_3$N or TEA Triethylamine
EtOAc ethyl acetate
Et$_2$O diethyl ether
EtOH Ethanol
GMF glass microfiber filter
Grubbs (II) (1,3-bis(2,4,6-trimethylphenyl)-2-imidazolidinylidene)dichloro(phenylmethylene) (triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
H$_2$SO$_4$ sulfuric acid
K$_2$CO$_3$ potassium carbonate
KOAc potassium acetate
K$_3$PO$_4$ potassium phosphate
LAH lithium aluminum hydride
LG leaving group
LiOH lithium hydroxide
MeOH Methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ Ammonia
NH$_4$Cl ammonium chloride
NH$_4$OH ammonium hydroxide
OTf triflate or trifluoromethanesulfonate
Pd$_2$(dba)$_3$ tris(dibenzylideneacetone)dipalladium(0)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
POCl$_3$ phosphorus oxychloride
i-PrOH or IPA Isopropanol
PS Polystyrene
SEM-Cl 2-(trimethysilyl)ethoxymethyl chloride
SiO$_2$ silica oxide
SnCl$_2$ tin(II) chloride
TBAI tetra-n-butylammonium iodide
TFA trifluoroacetic acid
THF tetrahydrofuran
TMSCHN$_2$ trimethylsilyldiazomethane
T3P propane phosphonic acid anhydride
TRIS tris (hydroxymethyl) aminomethane The compounds of the present invention can be prepared in a number of ways known to one skilled in the art of organic synthesis. The compounds of the present invention can be synthesized using the methods described below, together with synthetic methods known in the art of synthetic organic chemistry, or by variations thereof as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 3rd Ed., Wiley-Interscience (1999)).

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders which include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis, for example, alterations of the vessel wall, changes in the flow of blood, and alterations in the composition of the vascular compartment. These risk factors are collectively known as Virchow's triad. (*Hemostasis and Thrombosis, Basic Principles and Clinical Practice*, 5th Ed., p. 853, Colman, R. W. et al., eds., Lippincott Williams & Wilkins (2006))

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy) are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood*, 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood*, 108:192-199 (2006)). Contact activation is a surface mediated process responsible in part for the regulation of thrombosis and inflammation, and is mediated, at least in part, by fibrinolytic, complement, kininogen/kinin, and other humoral and cellular pathways (for review, Coleman, R., "Contact Activation Pathway", *Hemostasis and Thrombosis*, pp. 103-122, Lippincott Williams & Wilkins (2001); Schmaier, A. H., "Contact Activation", *Thrombosis and Hemorrhage*, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J. Exp. Med.*, 202:271-281 (2005); Kleinschmitz et al., *J. Exp. Med.*, 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-1370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med.*, 10:198-204 (2000))

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.*, 101:329-354 (2001)). Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.*, 87:774-777 (2002); Wang et al., *J. Thromb. Haemost.*, 3:695-702 (2005)). Also, factor XI deficiency rescues the perinatal lethal phenotype of complete protein C deficiency (Chan et al., *Amer. J. Pathology*, 158:469-479 (2001)). Furthermore, baboon cross-reactive, function blocking antibodies to human factor XI protect against baboon arterial—venous shunt thrombosis (Gruber et al., *Blood*, 102:953-955 (2003)). Evidence for an antithrombotic effect of small molecule inhibitors of factor XIa is also disclosed in published U.S. Patent Application No. 2004/0180855A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., Frontiers in Bioscience, 6:201-207 (2001); Gailani, D. et al., *Blood Coagulation and Fibrinolysis*, 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N. Engl. J. Med.*, 342:696-701 (2000)).

Plasma kallikrein is a zymogen of a trypsin-like serine protease and is present in plasma at 35 to 50 μg/mL. The gene structure is similar to that of factor XI. Overall, the amino acid sequence of plasma kallikrein has 58% homology to factor XI. Proteolytic activation by factor XIIa at an internal I389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", *Hemostasis and Thrombosis, pp.* 103-122, Lippincott Williams & Wilkins (2001); Schmaier A. H., "Contact Activation", *Thrombosis and Hemorrhage*, pp. 105-128 (1998)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide*, 2nd Ed., pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the enzyme; (f) factors that decrease the liability for clinical drug-drug interactions; (g) factors that decrease the potential for adverse side-effects, including selectivity versus other biological targets; and (h) factors that improve manufacturing costs or feasibility, (i) factors that are ideal for use as a parenteral agent such as solubility profile and pharmocokinetics.

Pre-clinical studies demonstrated significant antithrombotic effects of small molecule factor XIa inhibitors in rabbit and rat model of arterial thrombosis, at doses that preserved hemostasis. (Wong P. C. et al., *American Heart Association Scientific Sessions*, Abstract No. 6118, Nov. 12-15, 2006; Schumacher, W. et al., *Journal of Thrombosis and Haemostasis*, Vol. 3 (Suppl. 1):P1228 (2005); Schumacher, W. A. et al., *European Journal of Pharmacology*, pp. 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore), 78(5):285-291 (1999); Levine M. et al., *N. Engl. J. Med.,* 334(11):677-681 (1996); Blom, J. W. et al., *JAMA,* 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery,* 88:913-930 (2001).)

A. In Vitro Assays

The effectiveness of compounds of the present invention as inhibitors of the coagulation factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 1-5 nM, recombinant soluble tissue factor at a concentration of 10-40 nM and the synthetic substrate H-D-Ile-Pro-Arg-pNA (5-2288; CHROMOGENIX® or BMPM-2; AnaSpec) at a concentration of 0.001-0.0075 M.

Factor IXa determinations were made in 0.005 M calcium chloride, 0.1 M sodium chloride, 0.0001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; CHROMOGENIX®) at a concentration of 0.0002-0.00035 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate SPECTROZYME® #312 (pyroGlu-Pro-Arg-pNA; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; CHROMOGENIX®) at a concentration of 0.00008-0.0004 M. The $K_m$ value used for calculation of $K_i$ was 0.00005 to 0.00007 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; CHROMOGENIX®) at a concentration of 0.0002-0.00026 M.

The Michaelis constant, $K_m$, for substrate hydrolysis by each protease, was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$(v_o-v_s)/v_s=I/(K_i(1+S/K_m))$ for a competitive inhibitor with one binding site; or $v_s/v_o=A+((B-A)/1+((IC_{50}/(I)_n)))$; and $K_i=IC_{50}/(1+S/K_m)$ for a competitive inhibitor where:

$v_o$ is the velocity of the control in the absence of inhibitor;

$v_s$ is the velocity in the presence of inhibitor;

I is the concentration of inhibitor;

A is the minimum activity remaining (usually locked at zero);

B is the maximum activity remaining (usually locked at 1.0);

n is the Hill coefficient, a measure of the number and cooperativity of potential inhibitor binding sites;

$IC_{50}$ is the concentration of inhibitor that produces 50% inhibition under the assay conditions;

$K_i$ is the dissociation constant of the enzyme:inhibitor complex;

S is the concentration of substrate; and $K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective. Compounds with selectivity ratios >100 are preferred, and compounds with selectivity ratios >500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5x or IC2x, the inhibitor concentration required to increase the clotting time by 50 or 100 percent, respectively. The IC1.5x or IC2x is found by linear interpolation from relative clotting time versus inhibitor concentration plots using inhibitor concentration that spans the IC1.5x or IC2x.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Ill.). Similarly, clotting times can be determined from laboratory animal species or humans dosed with compounds of the invention.

Activated Partial Thromboplastin Time (aPTT) is determined using ALEXINO (Trinity Biotech, Ireland) or ACTIN® (Dade-Behring, Ill.) following the directions in the package insert. Plasma (0.05 mL) is warmed to 37° C. for 1 minute. ALEXIN® or ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus, Dade-Behring, Ill.) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

The Examples disclosed below were tested in the Factor XIa assay described above and found having Factor XIa inhibitory activity. A range of Factor XIa inhibitory activity (Ki values) of ≤10 μM (10000 nM) was observed. The results are shown in Tables 1 and A. The activity ranges in Table A are: A is 500-5000 nanocromolar (nM); B is 100-500 nM; C is 5-10 nM; D is <5 nM. Note that by using the Example Number in the tables the structures of the compounds can be found herein.

TABLE 1

| Example No. | Factor XIa Ki (nM) |
|---|---|
| 1 | <5.00 |
| 4 | 10.26 |
| 7 | 49.73 |
| 13 | <5.00 |
| 15 | 2440.00 |
| 16 | 2294.00 |
| 22 | <5.00 |
| 28 | 1217.00 |
| 37 | 86.45 |
| 41 | 5641.00 |
| 43 | 20.60 |
| 52 | <5.00 |
| 63 | 34.46 |
| 71 | 491.50 |
| 81 | <5.00 |
| 90 | 314.00 |
| 94 | <5.00 |
| 98 | 632.4 |
| 106 | <5.00 |
| 119 | <5.00 |
| 125 | 1006.00 |
| 128 | 132.70 |
| 131 | <5.00 |
| 155 | <5.00 |
| 169 | 516.80 |
| 175 | <5.00 |
| 184 | <5.00 |
| 189 | 1690.00 |
| 191 | 1051.00 |
| 193 | 107.30 |
| 196 | 843.70 |
| 198 | 5736.00 |
| 215 | <5.00 |
| 216 | 955.00 |
| 228 | <5.00 |
| 235 | 74.48 |
| 237 | 4617.00 |
| 240 | 47.10 |
| 250 | <5.00 |
| 257 | 2570.00 |
| 266 | <5.00 |

TABLE A

| Example No. | Factor XIa Ki (nM) |
|---|---|
| 2 | B |
| 3 | D |
| 5 | C |
| 6 | C |
| 8 | C |
| 9 | C |
| 10 | C |
| 11 | D |
| 12 | C |
| 14 | D |
| 17 | C |
| 18 | D |
| 19 | C |
| 20 | C |
| 21 | D |
| 23 | C |
| 24 | C |
| 25 | C |
| 26 | C |
| 27 | D |
| 29 | C |
| 30 | B |
| 31 | D |
| 32 | B |
| 33 | C |
| 34 | D |
| 35 | D |
| 36 | B |
| 38 | C |
| 39 | C |
| 40 | D |
| 42 | C |
| 44 | C |
| 45 | C |
| 46 | D |
| 47 | D |
| 48 | B |
| 49 | D |
| 50 | B |
| 51 | C |
| 53 | D |
| 54 | D |
| 55 | B |
| 56 | C |
| 57 | C |
| 58 | B |
| 59 | C |
| 60 | D |
| 61 | C |
| 62 | D |
| 64 | D |
| 65 | C |
| 66 | C |
| 67 | B |
| 68 | B |
| 69 | B |
| 70 | B |
| 72 | A |
| 73 | A |
| 74 | B |
| 75 | B |
| 76 | A |
| 77 | B |
| 78 | D |
| 79 | D |
| 80 | D |
| 82 | D |
| 83 | D |
| 84 | D |
| 85 | D |
| 86 | D |
| 87 | D |
| 88 | C |
| 89 | D |
| 91 | C |
| 92 | D |
| 93 | C |
| 95 | D |

TABLE A-continued

| Example No. | Factor XIa Ki (nM) |
|---|---|
| 96 | D |
| 97 | D |
| 99 | D |
| 100 | D |
| 101 | D |
| 102 | C |
| 103 | D |
| 104 | D |
| 105 | D |
| 107 | C |
| 108 | D |
| 109 | C |
| 110 | C |
| 111 | A |
| 112 | D |
| 113 | B |
| 114 | D |
| 115 | D |
| 116 | D |
| 117 | D |
| 118 | C |
| 120 | D |
| 121 | D |
| 122 | D |
| 123 | D |
| 124 | D |
| 126 | D |
| 127 | D |
| 129 | D |
| 130 | D |
| 132 | B |
| 133 | D |
| 134 | D |
| 135 | D |
| 136 | D |
| 137 | D |
| 138 | D |
| 139 | D |
| 140 | D |
| 141 | D |
| 142 | D |
| 143 | D |
| 144 | D |
| 145 | D |
| 146 | D |
| 147 | D |
| 148 | D |
| 149 | D |
| 150 | D |
| 151 | D |
| 152 | D |
| 153 | C |
| 154 | D |
| 156 | C |
| 157 | C |
| 158 | D |
| 159 | D |
| 160 | C |
| 161 | D |
| 162 | D |
| 163 | C |
| 164 | D |
| 165 | C |
| 166 | C |
| 167 | C |
| 168 | D |
| 170 | D |
| 171 | C |
| 172 | D |
| 173 | C |
| 174 | D |
| 176 | D |
| 177 | C |
| 178 | D |
| 179 | B |
| 180 | D |
| 181 | C |
| 182 | C |

TABLE A-continued

| Example No. | Factor XIa Ki (nM) |
|---|---|
| 183 | B |
| 185 | C |
| 186 | A |
| 187 | B |
| 188 | D |
| 190 | C |
| 192 | C |
| 194 | D |
| 195 | D |
| 197 | C |
| 199 | D |
| 200 | B |
| 201 | D |
| 202 | B |
| 203 | C |
| 204 | D |
| 205 | C |
| 206 | D |
| 207 | C |
| 208 | D |
| 209 | D |
| 210 | D |
| 211 | D |
| 212 | D |
| 213 | D |
| 214 | D |
| 217 | D |
| 218 | D |
| 219 | D |
| 220 | D |
| 221 | C |
| 222 | D |
| 223 | D |
| 224 | C |
| 225 | D |
| 226 | C |
| 227 | D |
| 229 | B |
| 230 | B |
| 231 | B |
| 232 | C |
| 233 | C |
| 234 | C |
| 236 | C |
| 238 | C |
| 239 | D |
| 241 | D |
| 242 | B |
| 243 | D |
| 244 | D |
| 245 | D |
| 246 | D |
| 247 | D |
| 248 | D |
| 249 | D |
| 251 | D |
| 252 | D |
| 253 | C |
| 254 | D |
| 255 | D |
| 256 | D |
| 258 | D |
| 259 | D |
| 260 | D |
| 261 | D |
| 262 | D |
| 263 | D |
| 264 | D |
| 265 | D |
| 267 | D |
| 268 | D |
| 269 | D |
| 270 | D |

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.,* 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-Venous (AV) Shunt Thrombosis Model

The rabbit AV shunt model, described by Wong et al. (Wong, P. C. et al., *J. Pharmacol. Exp. Ther.* 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Ed. (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By “administered in combination” or “combination therapy” it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastro-intestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPARgamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXR beta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAl derivatives or apoAl peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., Heterocycles, 16(1):35-7 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Scheme 1 illustrates a few approaches to the synthesis of compounds of Formula (I). Amide 1c can be prepared by amide coupling of commercially available or readily accessible acid 1a and readily accessible aniline 1b using methods commonly used in the literature, such as T3P/base, HOAt/EDC/base and/or $POCl_3$, pyridine. Deprotection of the protecting group $PG_1$ using appropriate conditions known to those in the art of organic synthesis, followed by coupling with acid 1e can yield compounds of formula 1g. Alternatively, coupling of amine 1d with acid 1e followed by deprotection can give acid 1f. The coupling of acid if with amine 1b under standard peptide coupling procedures can yield compounds of formula 1g. Appropriate functionalization of intermediates used in this invention to prepare compounds of formula 1g can be achieved through the Suzuki, Buchwald, Ullman or Mitsunobu reactions or simple reactions known to those in the art.

Scheme 1:

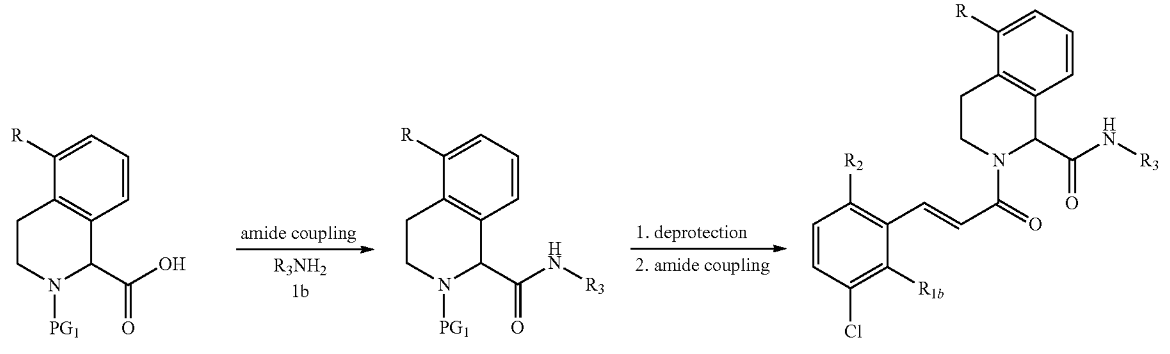

1a  1c  1g $PG_1$ = H/protecting group
R = halo or carbocyclic amine

-continued

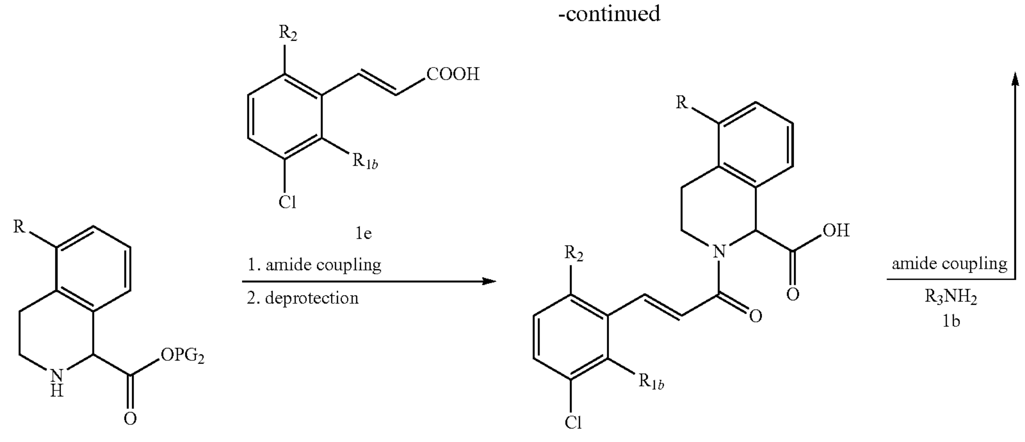

1d 1e 1f

Scheme 2 describes an alternative method to access compounds of this invention. Reaction of acid 1e, isocyanide 2a, and imine 2b can give Ugi product 2d (Schuster, I. et al., Letters in Organic Chemistry, 4(2):102-108 (2007)). Selective oxidation of tetrahydroisoquinoline 2c using known methods such as $MnO_2$ (Aoyama, T. et al., Synlett, 1:35-36 (1998)) can yield imine 2b, which can then be used via the three component Ugi coupling procedures described above. The Ugi coupling procedures can be used extensively with other imino derived intermediates contained in this invention. Further manipulations of the Ugi derived products can afford compounds of this invention.

Scheme 3 describes methods for preparing the tetrahydroisoquinoline intermediate 3c and 3e. Method A uses Bischler-Napieralski cyclization to access compounds such as intermediate 3c (Al-Hiari, Y. M. et al., Journal of Heterocyclic Chemistry, 42(4): 647-659 (2005)) or 3e (Zalan, Z. et al., Tetrahedron, 62(12): 2883-2891 (2006)). Method B uses the Friedel-Crafts alkylation reaction to access compounds such as intermediate 3c (Topsom, R. D. et al., Journal of the Chemical Society [Section] D: Chemical Communications, 15:799 (1971)). Alternatively, as described in Method C, cyclization of intermediate 3h and 3-aminopropanol (3i) can afford 3j. Reduction with $NaBH_4$, Scheme 2:

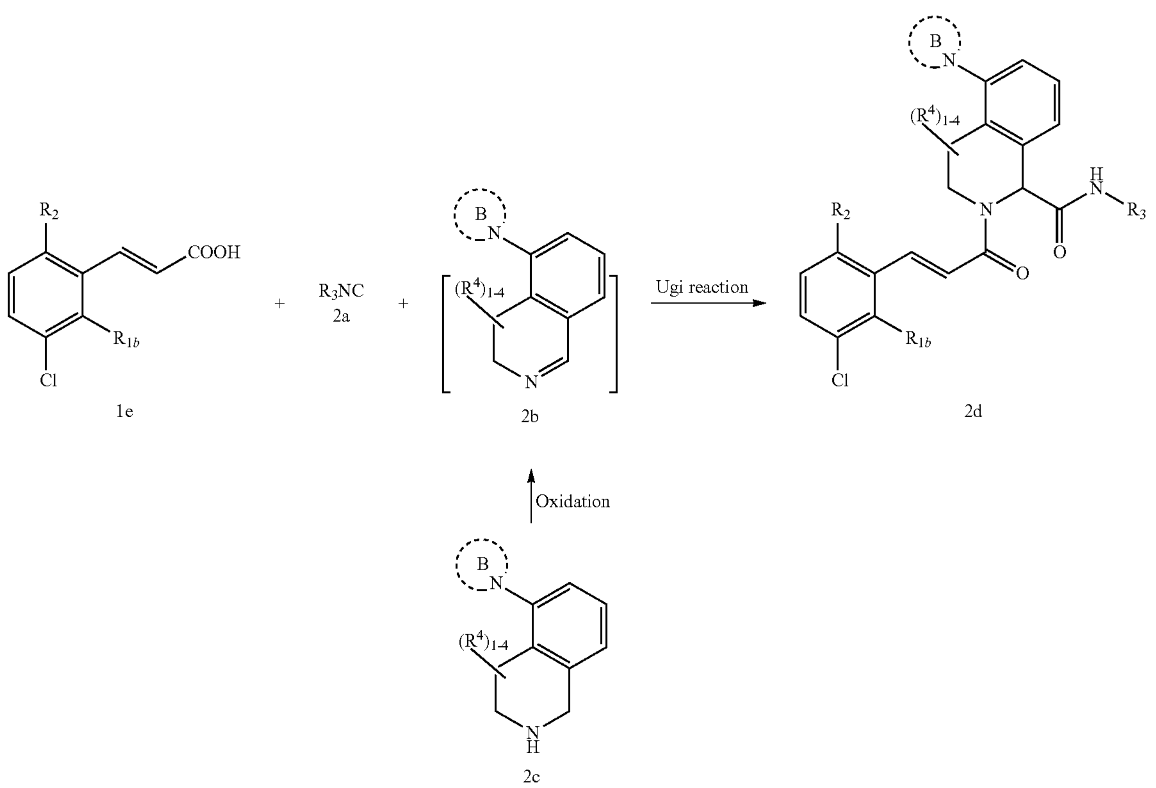

1e 2b 2d 2c followed by PCC oxidation gave β-amino aldehyde, which can be converted to 3c under basic conditions (Umetsu, K.; Asao, N., Tetrahedron Letters, 49(17): 2722-2725 (2008)). In Method D, lactam 3l can be synthesized from ketone 3k by the Beckmann rearrangement. Reduction of 3l can afford intermediates such as 3c (Vernier, J. et al., WO 2008024398 (2008)). In Method E, the dihydroisoquinoline carbaldehyde (3m) was converted to 3c under basic conditions (Martin, S. et al., WO 2006134143 (2006)). In Method F, dihydroisoquinolinethione was converted to 3c treating the thione 3o with bromopropene followed by treatment with perchloric acid and sodium borohydride (Mohinder, B, et al., Indian Journal of Chemistry, Section B: Organic Chemistry Including Medicinal Chemistry, 18B (4); 312-15 (1979)).

Scheme 3:

A)

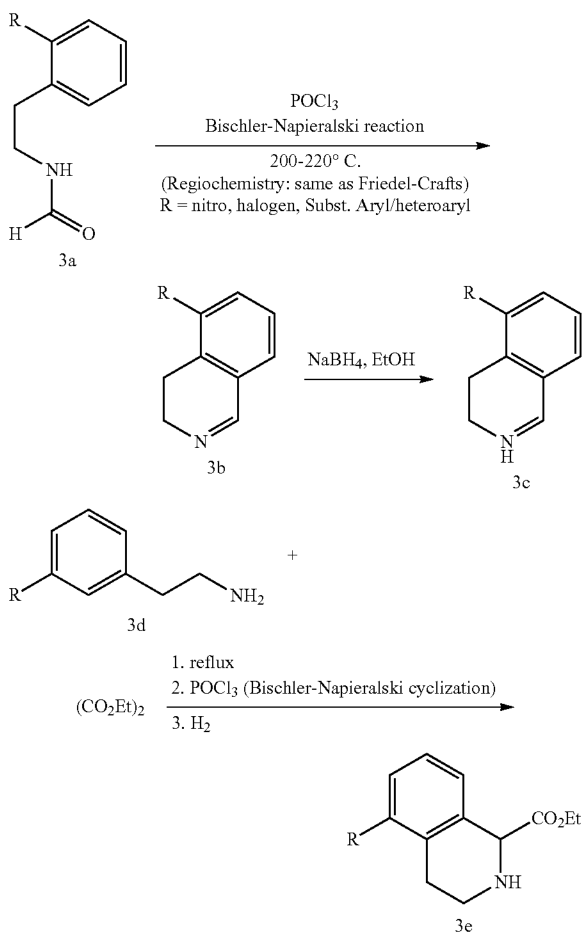

3a 3b 3c 3d 3e

B)

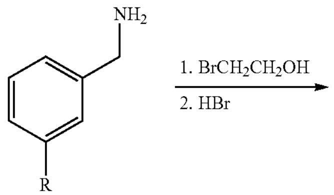

3f

-continued

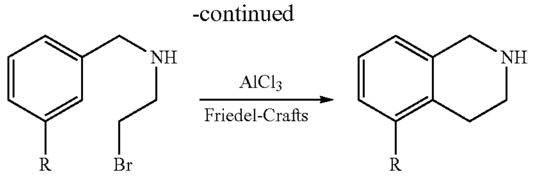

3g 3c

C)

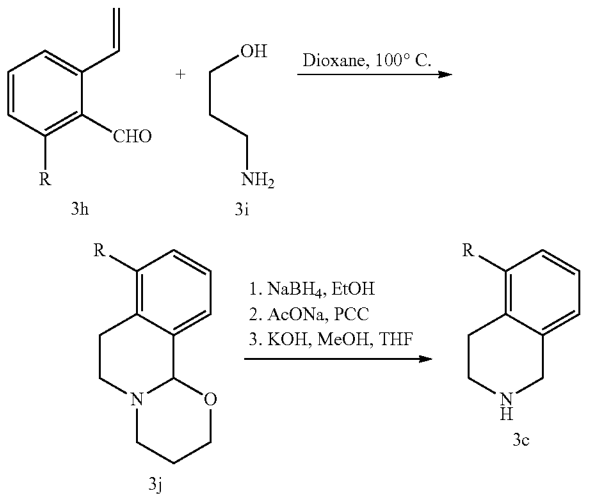

3h 3i 3j 3c

D)

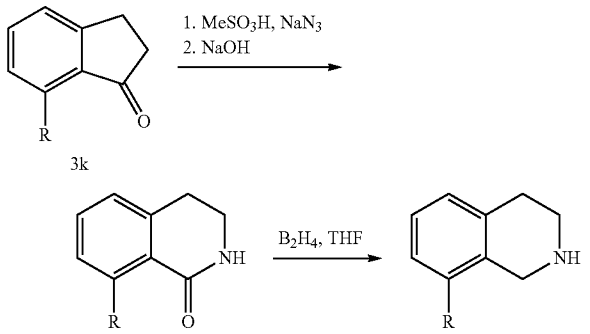

3k 3l 3c

E)

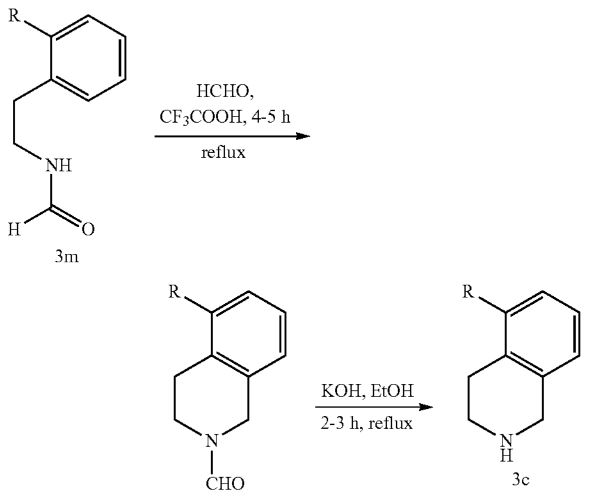

3m 3n 3c

-continued

F)

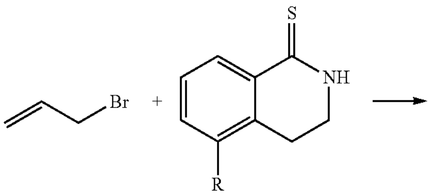

3o

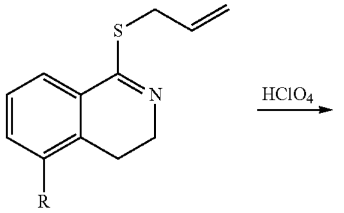

3p

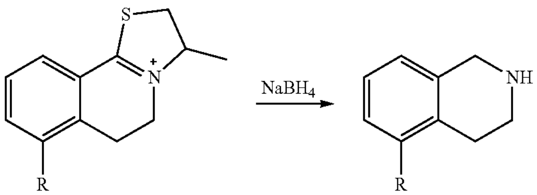

3q

3c

Preparation of substituted THQ analogs is shown in Scheme 4. Bromide 4a can be converted to nitrile 4b under lithiation conditions. Hydrolysis under basic conditions should lead to acid 4c, which can be converted to carbamate 4e via Curtius rearrangement. Formation of the THQ intermediate 4f can then be accomplished by treatment with paraformaldehyde in a mixture of acetic and sulfuric acid (Bigge, C. F. et al, Bioorganic & Medicinal Chemistry Letters, 3(1): 39-42 (1993)). Deprotection of carbamate 4f followed by protection with $Boc_2O$ should afford intermediate 4h, which can be subjected to the Suzuki cross coupling reaction with an appropriate boronate or boronic acid or the Stille coupling procedures known to those in the art.

Scheme 4:

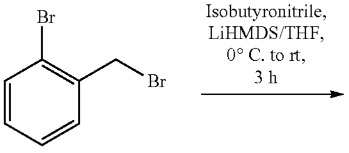

4a

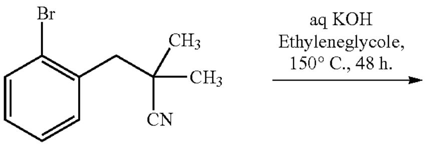

4b

-continued

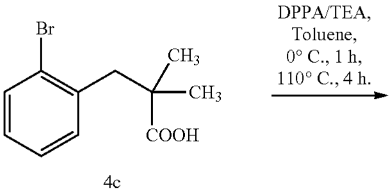

4c

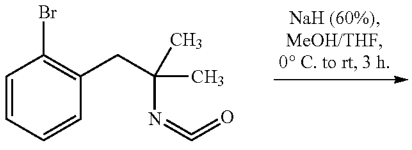

4d

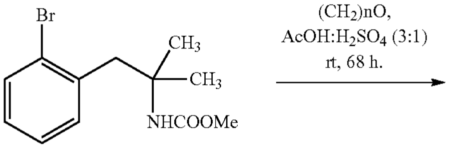

4e

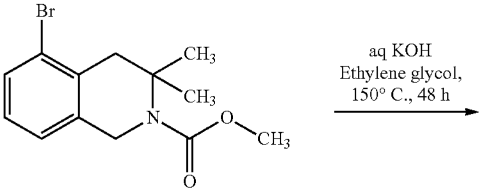

4f

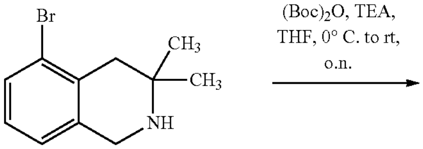

4g

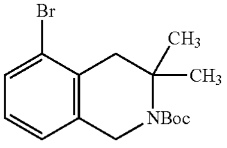

4h

Purification of intermediates and final products was carried out via either normal or reverse phase chromatography. Normal phase chromatography was carried out using prepacked $SiO_2$ cartridges eluting with either gradients of hexanes and EtOAc or DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% ACN, 0.1% TFA) and Solvent B (10% water, 90% ACN, 0.1% TFA, UV 220 nm) or with gradients of Solvent A (98% water, 2% ACN, 0.05% TFA) and Solvent B (98% ACN, 2% water, 0.05% TFA, UV 220 nm).

Unless otherwise stated, analysis of final products was carried out by reverse phase analytical HPLC.

Method A: A majority of analytical HPLC runs were: SunFire (4.6×150 mm) (15 min gradient—95:5 $H_2O$/ACN-to 95:5ACN/$H_2O$-0.05% TFA).

Method B: A minority of analytical HPLC runs were: Zorbax (4.6×75 mm) (8 min gradient-10:90 MeOH/$H_2O$ to 90:10 MeOH/$H_2O$, 0.2% $H_3PO_4$)

A majority of mass spectra runs were run using Phenomenex Luna C18 (2×30 mm) (2 min gradient 90% $H_2O$/10% MeOH/0.1% TFA to 90% MeOH/10% $H_2O$/0.1% TFA)

Intermediate 1

(E)-2,5-Dioxopyrrolidin-1-yl 3-(5-chloro-2-(1H-tetrazol-1-yl)phenyl)acrylate

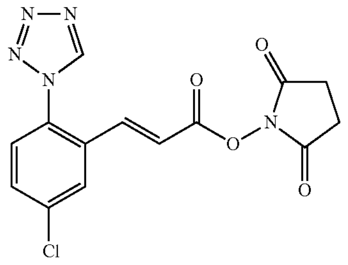 [SMILES: O=C(/C=C/c1cc(Cl)ccc1-n1cnnn1)ON1C(=O)CCC1=O]

The synthesis was described as Intermediate 1 in PCT International Application, WO 2009/114677 published Sep. 17, 2009.

Intermediate 2

(E)-3-(5-chloro-2-tetrazol-1-yl-phenyl)-acrylic acid

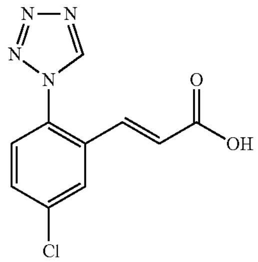 [SMILES: O=C(O)/C=C/c1cc(Cl)ccc1-n1cnnn1]

The synthesis was described as Intermediate 1B in PCT International Application, WO 2009/114677 published Sep. 17, 2009.

Intermediate 3

(E)-3-(3-Chloro-2-fluoro-6-tetrazol-1-yl-phenyl)-acrylic acid 2,5-dioxo-pyrrolidin-1-yl ester

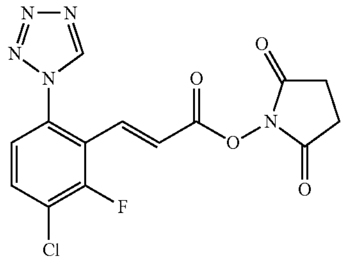 [SMILES: O=C(/C=C/c1c(-n2cnnn2)ccc(Cl)c1F)ON1C(=O)CCC1=O]

Intermediate 3A (E)-3-(3-chloro-2-fluoro-6-(1H-tetrazol-1-yl)phenyl) acrylic acid The synthesis of Intermediate 3A was described as Intermediate 7 in PCT International Application, WO 2009/114677 published Sep. 17, 2009.

Intermediate 3: To a slightly turbid mixture of Intermediate 3A (1.0 g, 3.72 mmol) in THF (18.70 mL) and DMF (1.870 mL) was added 1-hydroxypyrrolidine-2,5-dione (0.471 g, 4.09 mmol) and DIC (0.638 mL, 4.09 mmol). The reaction was stirred at rt and a white precipitate formed overtime. The solid was collected by suction filtration and washed with MeOH and $H_2O$. The crude product was then air-dried and finally dried under vacuum to give Intermediate 3 (0.98 g, 72%), as a white solid. $^1H$ NMR (500 MHz, DMSO-$d_6$) δ 9.92 (s, 1H), 8.06 (t, J=8.12 Hz, 1H), 7.72 (d, J=8.80 Hz, 1H), 7.36 (d, J=16.23 Hz, 1H), 6.81 (d, J=16.51 Hz, 1H), 2.84 (s, 4H) ppm. MS (ESI) m/z: 366.2 $(M+H)^+$.

Intermediate 4

(E)-3-(2-acetyl-5-chlorophenyl)acrylic acid

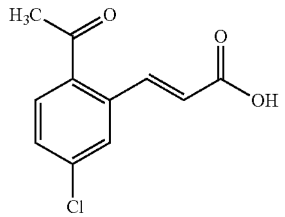

Intermediate 4A (E)-tert-butyl 3-(2-acetyl-5-chlorophenyl)acrylate

To a degassed solution of 1-(2-bromo-4-chlorophenyl) ethanone (1.0 g, 4.28 mmol), tributylamine (2.041 mL, 8.57 mmol), and tert-butyl acrylate (1.255 mL, 8.57 mmol) in DMF (10 mL) was added palladium on carbon (0.456 g, 0.428 mmol) and palladium (II) acetate (0.096 g, 0.428 mmol). The reaction mixture was warmed to 100° C. After 16 h, the reaction was cooled to rt and filtered. The solid was rinsed with DMF and the filtrate was diluted with EtOAc and washed with $H_2O$ (2×) followed by brine. The crude product was then dried over $Na_2SO_4$, filtered and concentrated. Purification by normal phase chromatography afforded Intermediate 4A (0.760 g, 63%), as a brown oil. MS (ESI) m/z: 225.0 $(M-C4H8+H)^+$.

Intermediate 4: A solution of Intermediate 4A (0.048 g, 0.171 mmol) in 50% TFA/DCM (2 mL) was stirred at rt. After 1 h, the reaction was concentrated to give Intermediate 4 (0.038 g, 100%) as a yellow solid. The material was carried onto the next step without further purification. MS (ESI) m/z: 225.1 $(M+H)^+$.

Intermediate 5

(E)-3-(5-chloro-4-fluoro-2-(1H-tetrazol-1-yl)phenyl) acrylic acid

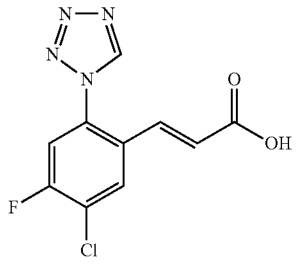 [SMILES: O=C(O)/C=C/c1cc(Cl)c(F)cc1-n1cnnn1]

Intermediate 5A: 4-chloro-5-fluoro-2-iodoaniline

To 4-chloro-3-fluoroaniline (25 g, 0.17 mmol) in 250 mL of $H_2O$ was added $NaHCO_3$ (21.6 g, 0.25 mmol). After cooling to 0° C., iodine (43.5 g, 0.17 mmol) was added. After 18 h at rt, an additional 10.8 g of iodine was added and the reaction was stirred overnight. The reaction was extracted with DCM (4×250 mL), the combined organics were washed with sodium thiosulfate solution (2×250 mL) and brine (2×250 mL) and dried ($Na_2SO_4$). Purification by silica gel chromatography gave 47 g of Intermediate 5A. MS (ESI) m/z: 145.2 $(M+H)^+$.

Intermediate 5B: 1-(4-chloro-5-fluoro-2-iodophenyl)-1H-tetrazole

To Intermediate 5A (47 g, 17.3 mmol) in AcOH (470 mL) was added $NaN_3$ (33.76 g, 51.9 mmol) and trimethyl orthoformate (56.8 mL, 51.9 mmol). After 30 h, the reaction was poured into ice $H_2O$, the solids were filtered-off and washed with petroleum ether to afford 49 g Intermediate 5B. MS (ESI) m/z: 324.8 $(M+H)^+$.

Intermediate 5C: (E)-methyl 3-(5-chloro-4-fluoro-2-(1H-tetrazol-1-yl)phenyl)acrylate A solution of Intermediate 5B (100 g, 324.4 mmol) in ACN (1000 mL) was degassed with N2. TEA (64 mL) and methyl acrylate (60 mL) were added and the reaction was further degassed. $Pd(OAc)_2$ (8 g, 11.8 mmol) was added and the reaction was heated to 85° C. for 18 h. The reaction was concentrated and the residue was diluted with $H_2O$. The aqueous layer was extracted with EtOAc and the combined organics were washed with brine. Purification by silica gel chromatography gave 25 g Intermediate 5C. MS (ESI) m/z: 283.0 $(M+H)^+$.

Intermediate 5: (E)-3-(5-chloro-4-fluoro-2-(1H-tetrazol-1-yl)phenyl)acrylic acid To Intermediate 5C (5 g, 17.7 mmol) in MeOH (50 mL) and THF (25 mL) was added 10% NaOH solution (25 mL). After 2 h, the reaction was concentrated and the residue was diluted with $H_2O$. The pH was adjusted to 2 to 3 with 1.5N HCl and the resultant solid was filtered and washed with petroleum ether to afford 2 g of Intermediate 5. MS (ESI) m/z: 269.0 $(M+H)^+$.

Intermediate 6 tert-Butyl 4-isocyanobenzoate

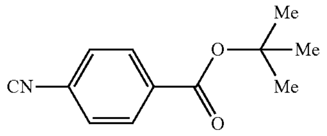

Intermediate 6A: tert-Butyl 4-formamidobenzoate

Combined tert-butyl 4-aminobenzoate (15.3 g, 79 mmol), DMAP (1.935 g, 15.84 mmol), N-methylmorpholine (15.67 mL, 143 mmol) in DCM (120 mL) and, after cooling to 0° C., slowly added formic acid (9.11 mL, 238 mmol). After stirring for 18 h, the reaction was concentrated and then partitioned with 1N HCl (100 mL) and EtOAc (200 mL). The aqueous layer was extracted with EtOAc (100 mL). The combined organic layer was washed with brine (50 mL) and dried ($MgSO_4$). The desired product was collected as yellow syrup (16 g).

Intermediate 6: To Intermediate 6A in THF (300 mL) was added TEA (33 mL, 238 mmol) and the after cooling to 0° C., $POCl_3$ (7.3 mL, 79 mmol) was slowly added and the reaction was stirred at room temperature. After 24 h, the reaction was partitioned between EtOAc (200 mL) and aqueous $NaHCO_3$ (100 mL). The aqueous layer was extracted with EtOAc (100 mL). The combined organic layer was washed with brine (50 mL) and dried ($MgSO_4$). Purification by normal phase chromatography afforded 10.4 g (64.6%) of intermediate 6 as a green solid. $^1H$ NMR (400 MHz, $CDCl_3$) δ□ 8.02 (d, J=8.59 Hz, 2H), 7.41 (d, J=8.34 Hz, 2H), 1.60 (s, 9H) ppm.

Intermediate 7

4-Isocyanobenzonitrile

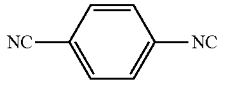

Intermediate 7 was prepared in a similar manner as Intermediate 6 from 4-isocyanoaniline. $^1H$ NMR (400 MHz, $CDCl_3$) δ 7.68-7.84 (m, 2H) 7.51 (d, J=8.34 Hz, 2H) ppm.

Intermediate 8 tert-Butyl 6-isocyano-1H-indazole-1-carboxylate

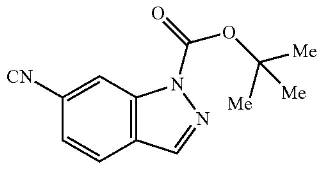

Intermediate 8 was prepared in a similar manner as Intermediate 6 from tert-butyl 6-amino-1H-indazole-1-carboxylate. $^1$H NMR (400 MHz, $CDCl_3$) δ 8.28 (1H, s), 8.20 (1H, s), 7.76 (1H, d, J=8.34 Hz), 7.28-7.40 (1H, m), 1.74 (9H, s) ppm. MS (ESI) m/z: 144 (M+H-Boc)$^+$.

Intermediate 9

Ethyl 4-isocyanobenzoate

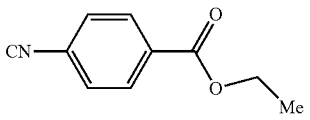

Intermediate 9 was prepared in a similar manner as Intermediate 6. $^1$H NMR (400 MHz, $CDCl_3$) δ 1.40 (t, J=7.20 Hz, 3H) 4.40 (q, J=7.24 Hz, 2H) 7.44 (d, J=8.59 Hz, 2H) 8.00-8.17 (m, 2H) ppm. MS (ESI) m/z: 176 (M+H)$^+$.

Intermediate 10

Methyl 4-isocyanophenylcarbamate

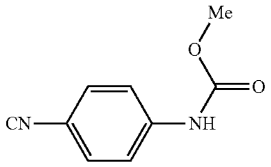

Intermediate 10A: 1-Boc-methyl 4-aminophenylcarbamate

To tert-butyl 4-aminophenylcarbamate (2.1 g, 10.08 mmol) in a separatory funnel with DCM (75 mL) and saturated aqueous $NaHCO_3$ (25 mL) was added methyl chloroformate (0.937 mL, 12.10 mmol). After shaking for 10 min a thick pink gel formed. The solid was filtered off and dried. The aqueous layer was extracted with DCM (50 mL) and dried (Mg504). All solids collected were combined to afford 2.6 g of Intermediate 10A. $^1$H NMR (400 MHz, MeOD) δ 7.32 (4H, s), 3.73 (3H, s), 1.53 (9H, s) ppm.

Intermediate 10B: methyl 4-aminophenylcarbamate

Intermediate 10A (2.6 g, 9.77 mmol) was deprotected with 30% TFA in DCM (40 mL). After 2 h, the reaction was concentrated and the residue was partitioned with EtOAc (75 mL) and saturated $NaHCO_3$ (50 mL). The organic layer was washed with brine (20 mL) and dried ($MgSO_4$). Crude Intermediate 10B was carried onto the next step. $^1$H NMR (400 MHz, DMSO-$d_6$) δ 9.86 (1H, s), 7.56 (2H, d, J=8.84 Hz), 7.28 (2H, d, J=8.84 Hz), 6.90 (2H, s), 3.68 (3H, s) ppm.

Intermediate 10C: methyl 4-formamidophenylcarbamate

Crude Intermediate 10B was heated to reflux in ethyl formate for several days. The solvent was removed and the residue was purified by silica gel chromatography to afford 2.9 g of Intermediate 10C as brown oil. MS (ESI) m/z: 195.0 (M+H)$^+$.

Intermediate 10 was made in a similar manner as Intermediate 6 to afford 0.31 g (17.8%) of a tan solid. $^1$H NMR (400 MHz, $CDCl_3$) δ 7.45 (2H, d, J=8.8 Hz), 7.33-7.41 (2H, m), 6.73 (1H, br. s.), 3.82 (3H, s) ppm.

Intermediate 11 benzyl 6-isocyano-1H-indazole-1-carboxylate

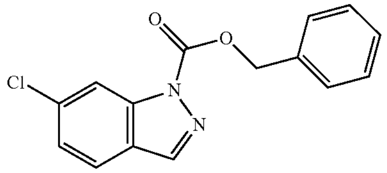 [SMILES: O=C(OCc1ccccc1)n1ncc2ccc(Cl)cc21]

Intermediate 11 was made in a similar manner as Intermediate 6 and Intermediate 8 starting from benzyl 6-amino-1H-indazole-1-carboxylate: $^1$H NMR (400 MHz, $CDCl_3$) δ 8.31 (1H, s), 8.21 (1H, s), 7.76 (1H, d, J=8.34 Hz), 7.54 (2H, d, J=6.82 Hz), 7.30-7.47 (4H, m), 5.56 (2H, s) ppm. MS (ESI) m/z: 234 (M+H–CO2)$^+$.

Intermediate 12

(E)-3-(6-acetyl-3-chloro-2-fluorophenyl)acrylic acid

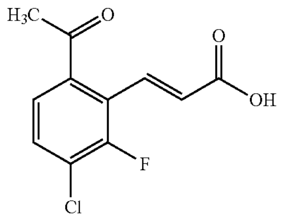 [SMILES: CC(=O)c1ccc(Cl)c(F)c1/C=C/C(=O)O]

Intermediate 12A: 2-bromo-4-chloro-3-fluorobenzoic acid

To a cooled (−78° C.) solution of DIEA (4.9 mL, 48 mmol) in THF was added dropwise n-BuLi (132 mL, 2.3 eq, 2.5 M). The mixture was stirred at −30° C. for 30 min. Again the reaction mixture was cooled to −78° C., and a solution of 4-chloro-3-fluorobenzoic acid (25 g, 143 mmol) in THF was added over 1 h. The reaction was stirred at −78° C. overnight. The next day a solution of 1,2-dibromo-1,1,2,2-tetrachloroethane (87 g, 267 mmol) in THF was added and the reaction was stirred at −78° C. for further 2 h and then rt for 4 h. The reaction mixture was quenched with $H_2O$, organic layer was separated and aqueous layer washed with $Et_2O$. Aqueous layer acidified with 1.5 N HCl and extracted in EtOAc (2×200 mL), dried over anhydrous $Na_2SO_4$, filtered and concentrated to afford Intermediate 12A (30 g, 83.3%). MS (ESI) m/z: 252.6 (M−H)$^+$.

Intermediate 12B: Diethyl 2-((2-bromo-4-chloro-3-fluorophenyl) (hydroxy)methylene)malonate To a suspension of Intermediate 12A (14.6 g, 57 mmol) in DCM (200 mL) was added thionyl chloride (6.6 mL, 88 mmol). The mixture was stirred at reflux for 3 h. Solvent was removed and the residue was dried in vacuum to give the acid chloride as a light brown solid. To a cooled (0° C.) suspension of sodium hydride (3.66 g (60%), 91.5 mmol) in THF was added a solution of diethyl malonate (0.612 g, 3.82 mmol) in THF (5 mL). After 10 min, a solution of the acid chloride (16.4 g, 60 mmol) in THF (160 mL) was added slowly. Following the addition, the reaction was warmed to rt. After 30 min, the solvent was removed and the residue was treated with cold (0° C.) 1.2 M HCl (150 mL). The mixture was extracted with EtOAc (3×250 mL). The combined organic layers were washed with brine, dried over $Na_2SO_4$, filtered, and concentrated to give Intermediate 12B (20 g, 87%) as a solid. MS (ESI) m/z: 395 $(M+H)^+$.

Intermediate 12C: 1-(2-Bromo-4-chloro-3-fluorophenyl)ethanone

A solution of Intermediate 12B (18.6 g, 47 mmol) in AcOH (200 mL), $H_2O$ (150 mL) and $H_2SO_4$ (2.0 mL) was stirred at 110° C. for 4 h. Most of the solvent was removed and the residue was diluted with EtOAc (400 mL), washed with $H_2O$ (5×20 mL), saturated $NaHCO_3$, 1N NaOH, and brine. The solvent was removed to give Intermediate 12C (10 g, 84% yield) as a low melting solid. $^1H$ NMR (400 MHz, DMSO-$d_6$) δ 7.42 (q, J=6.8, 6.4 Hz, 1H), 7.24 (q, J=6.4, 5.2 Hz, 1H), 2.5 (s, 3H) ppm.

Intermediate 12D: (E)-tert-Butyl 3-(6-acetyl-3-chloro-2-fluorophenyl)acrylate

To a mixture of Intermediate 12C (50 g, 198 mmol), tert-butyl acrylate (50.9 g, 397 mmol) and TEA (55 mL, 397 mmol) in DMF (500 mL) was added $Pd(OAc)_2$ (8.9 g, 39.7 mmol). The resulting mixture was stirred at 90° C. overnight. The reaction was cooled to rt, filtered, and the filtrate was concentrated. Purification by column chromatography gave Intermediate 12D (30 g, 51%) as a light yellow solid. MS (ESI) m/z: 242.7 $(M+H)^+$.

Intermediate 12: A solution of Intermediate 12D (25 g, 84 mmol) in DCM (330 mL) and TFA (330 mL) was stirred at rt. After 1.5 h, the solvent was concentrated to give Intermediate 12 (19.5 g, 97%) as a white solid. $^1H$ NMR (400 MHz, DMSO-$d_6$) δ 12.69 (bs, 1H), 7.80-7.76 (m, 2H), 7.62 (d, J=12.1 Hz, 1H), 6.30 (dd, J=2.4, 2.0 Hz, 1H), 2.6 (s, 3H) ppm. MS (ESI) m/z: 241 $(M-H)^+$.

Intermediate 13

(E)-3-(3-Chloro-6-cyano-2-fluorophenyl)acrylic acid

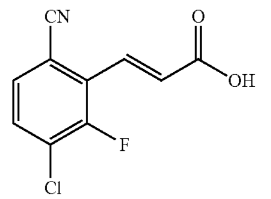 [SMILES: N#Cc1ccc(Cl)c(F)c1/C=C/C(=O)O]

Intermediate 13: 2-Bromo-4-chloro-3-fluorobenzamide

To a solution of 2-bromo-4-chloro-3-fluorobenzoic acid (20 g, 0.078 mol) in DCM (200 mL) was added thionyl chloride (14.7 g, 0.125 mol) followed by DMF (29.5 g, 0.5 moles) and the reaction was heated to reflux for 4 h. The reaction was then cooled to 0° C. and $NH_3$ gas was bubbled in until the pH was basic. After 30 min, the reaction mixture was quenched with $H_2O$ and extracted with DCM. The combined organics were washed with $H_2O$, brine, dried over $Na_2SO_4$, filtered and concentrated to yield the crude product. The crude product was finally suspended in petroleum ether and filtered to afford 16.5 g of Intermediate 13A. MS (ESI) m/z: 250.0 $(M+H)^+$.

Intermediate 13B: 2-Bromo-4-chloro-3-fluorobenzonitrile

To Intermediate 13A (10 g, 39 mmol) was added $POCl_3$ (100 mL) and NaOH (5 g, 87 mmol) and the reaction was heated to 110° C. for 2 h. The reaction mixture was concentrated and the residue was quenched with ice water. Extracted with EtOAc and the combined organics were washed with 10% $NaHCO_3$, brine, dried over $Na_2SO_4$, filtered, and concentrated to afford 8.5 g of 13B. MS (ESI) m/z: 232.9 $(M+H)^+$.

Intermediate 13C: (E)-Methyl 3-(3-chloro-6-cyano-2-fluorophenyl)acrylate

Combined Intermediate 13B (7 g, 29.9 mmol), tetrabutylammonium bromide (9.6 g, 29.9 mmol), $NaHCO_3$ (6.2 g, 74.8 mmol), methyl acrylate (5.2 g, 59.8 mmol) and $Pd(OAc)_2$ in DMF (50 mL). After stirring at rt for 18 h, the reaction was heated to 90° C. for 4 h. The reaction was then cooled to rt and filtered through Celite®. Purification by normal phase chromatography afforded 3.5 g of Intermediate 13C. MS (ESI) m/z: 257 $(M+H_2O)^+$.

Intermediate 13: To Intermediate 13C (0.5 g, 2.0 mmol) in THF (15 mL) and MeOH (5 mL) was added 1N LiOH (5 mL, 5 mmol). After 2 h, the volatile solvents were removed and the aqueous layer was extracted with EtOAc. The aqueous layer was acidified and extracted with EtOAc and the combined organics were washed with $H_2O$, brine, dried over $Na_2SO_4$, filtered and concentrated to afford 0.3 g of Intermediate 13. MS (ESI) m/z: 226.2 $(M+2+H)^+$.

Intermediate 14

(E)-3-(5-Chloro-2-(difluoromethyl)phenyl)acrylic acid

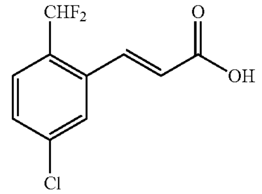 [SMILES: O=C(O)/C=C/c1cc(Cl)ccc1C(F)F]

Intermediate 14A: 2-Bromo-4-chloro-1-(difluoromethyl)benzene

To a solution of 2-bromo-4-chlorobenzaldehyde (1 g, 4.56 mmol) in DCM (15 mL) was added DAST (0.903 mL, 6.83 mmol) at 0° C. The reaction was allowed to warm to rt and stirred overnight. The reaction mixture was diluted with EtOAc, washed with saturated $NaHCO_3$ and brine. The organic phase was dried over $MgSO_4$, filtered and concentrated to give Intermediate 14A (0.88 g. 80%) as a clear oil. MS (ESI) m/z: 261.2 $(M+Na)^+$.

Intermediate 14B: (E)-tert-Butyl 3-(5-chloro-2-(difluoromethyl)phenyl) acrylate

To a solution of Intermediate 14A (0.88 g, 3.64 mmol) in DMF (10 mL) was added tert-butyl acrylate (1.401 g, 10.93 mmol), TEA (1.270 mL, 9.11 mmol) and $Pd(OAc)_2$ (0.082 g, 0.364 mmol). The reaction was warmed to 90° C. After 5 h, the reaction was cooled to rt and then filtered to remove the solid. The filtrate was diluted with EtOAc, washed with 1M HCl, saturated $NaHCO_3$, and brine. The organic phase was dried over $MgSO_4$, filtered and concentrated. Purification by normal phase chromatography gave Intermediate 14B (232 mg, 22%) as a tan oil. MS (ESI) m/z: 233.1 $(M-tBu)^+$.

Intermediate 14: To a solution of Intermediate 14B (232 mg, 0.804 mmol) in DCM (2.0 mL) was added TFA (2.0 mL, 26.0 mmol). The reaction was stirred under argon at rt. After 1 h, the solvent was removed and residue was dried to give Intermediate 14 (191 mg, 100%) as tan solid. $^1H$ NMR (400 MHz, MeOD) δ 7.99 (dt, J=15.8, 1.5 Hz, 1H), 7.83 (s, 1H), 7.60 (d, J=8.3 Hz, 1H), 7.55-7.48 (m, 1H), 7.01 (t, J=54.6 Hz, 1H), 6.51 (d, J=15.8 Hz, 1H). 19F NMR (376 MHz, MeOD) □δ −111.67 (s, 2F) ppm. MS (ESI) m/z: 233.1 $(M+H)^+$.

Intermediate 15

(E)-3-(5-Chloro-2-(difluoromethoxy)phenyl)acrylic acid

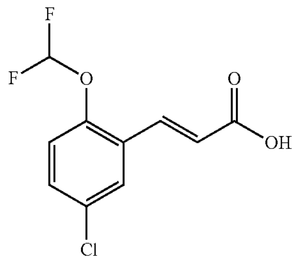 [SMILES: O=C(O)/C=C/c1cc(Cl)ccc1OC(F)F]

Intermediate 15A (E)-tert-Butyl 3-(5-chloro-2-(difluoromethoxy)phenyl) acrylate: To a solution of potassium tert-butoxide (0.407 g, 3.63 mmol) in THF (10 mL) were added tert-butyl 2-(dimethoxyphosphoryl)acetate (0.528 mL, 2.66 mmol) and 5-chloro-2-(difluoromethoxy)benzaldehyde (0.50 g, 2.420 mmol) at 0° C. After 4 h, $NH_4Cl$ solution was added and the reaction mixture was diluted with EtOAc, washed with saturated $NH_4Cl$ solution, saturated $NaHCO_3$, and brine. The organic phase was dried over $Na_2SO_4$, filtered and concentrated. The crude product was purified by normal phase chromatography to yield Intermediate 15A as a white solid (550 mg, 74%). MS (ESI) m/z: 327.0 $(M+Na)^+$. $^{19}F$ NMR (376 MHz, $CDCl_3$) δ −81.11 (1F, s) ppm.

Intermediate 15: To a solution of (E)-tert-butyl 3-(5-chloro-2-(difluoromethoxy) phenyl)acrylate (458 mg, 1.503 mmol) in DCM (4 mL) was added TFA (2.0 mL, 26.0 mmol). After 1 h, the solvent was removed to give Intermediate 15 as a white solid. MS (ESI) m/z: 249.0 $(M+H)^+$.

Intermediate 16

(E)-3-(3-chloro-2-fluoro-6-(trifluoromethyl)phenyl) acrylic acid

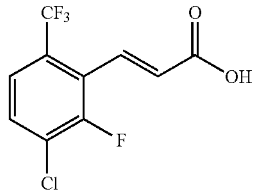 [SMILES: O=C(O)/C=C/c1c(C(F)(F)F)ccc(Cl)c1F]

Intermediate 16 was made in a similar manner as Intermediate 15 substituting 3-chloro-2-fluoro-6-(trifluoromethyl)benzaldehyde for 5-chloro-2-(difluoromethoxy) benzaldehyde followed by TFA deprotection. MS (ESI) m/z: 292 $(M+Na)^+$. $^1H$ NMR (400 MHz, $CDCl_3$) δ 7.87 (1H, dd, J=16.17, 2.02 Hz), 7.49-7.62 (2H, m), 6.67 (1H, dd, J=16.30, 1.39 Hz) ppm.

Intermediate 17: 1-cyclopentyl-3-(3,4-dihydroisoquinolin-5-yl)urea

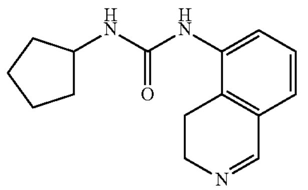 [SMILES: O=C(Nc1cccc2c1CCN=C2)NC1CCCC1]

Intermediate 17A

1-Cyclopentyl-3-(isoquinolin-5-yl)urea

To isoquinolin-5-amine (0.23 g, 1.595 mmol) in DCM (5 mL) was added DIEA (0.557 mL, 3.19 mmol) and isocyanatocyclopentane (0.180 mL, 1.595 mmol). After 24 h, the reaction was quenched with $H_2O$ (15 mL) and extracted with EtOAc (3×30 mL). The combined organic layers were washed with brine (10 mL) and dried ($MgSO_4$). The impure yellow solid was collected and was carried onto the next step. MS (ESI) m/z: 256 $(M+H)^+$.

Intermediate 17B: 1-Cyclopentyl-3-(1,2,3,4-tetrahydroisoquinolin-5-yl)urea 17A was hydrogenated at 55 psi in EtOH (25 mL) in the presence of $PtO_2$ (30 mg). After 24 h, the reaction was filtered through Celite® and filtrate concentrated to give 0.389 g of Intermediate 17B as a white oily solid. MS (ESI) m/z: 260.1 $(M+H)^+$.

Intermediate 17: Intermediate 17B was oxidized with $MnO_2$ (2.496 g, 28.7 mmol) in DCM (20 mL). After 24 h, the reaction was filtered through Celite® and concentrated to 0.34 g (83%) of brown solid. MS (ESI) m/z: 258.1 $(M+H)^+$.

Intermediate 18 tert-butyl 4-(3,4-dihydroisoquinolin-5-yl)piperazine-1-carboxylate

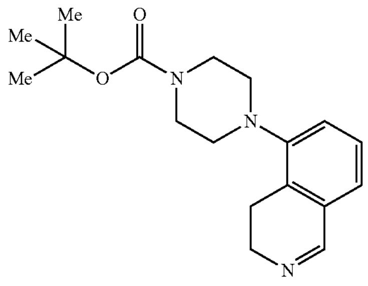 [SMILES: CC(C)(C)OC(=O)N1CCN(c2cccc3c2CCN=C3)CC1]

Intermediate 18A: tert-butyl 4-(1,2,3,4-tetrahydroisoquinolin-5-yl)piperazine-1-carboxylate To 5-(piperazin-1-yl)isoquinoline, HCl (0.58 g, 2.322 mmol) and NaOH (5.11 mL, 5.11 mmol) in dioxane (6 mL), cooled in ice bath, was added $Boc_2O$ (0.539 mL, 2.322 mmol) in dioxane (6 mL). The organics were stripped and the reaction was partitioned with $H_2O$ (30 mL) and EtOAc (100 mL). The organic layer was washed with brine (15 mL) and dried ($MgSO_4$). Collected Boc-protected compound as a yellow oil (0.86 g) which was then hydrogenated at 55 psi with $PtO_2$ in EtOH. The crude product was then filtered through Celite® and collected 0.73 g (99%) of the desired product as a off-white solid. MS (ESI) m/z: 318.1 $(M+H)^+$.

Intermediate 18: Intermediate 18A was reduced and then oxidized in a similar manner as described for Intermediate 17. MS (ESI) m/z: 316.1 $(M+H)^+$.

Intermediate 19

5-(4-Methylpiperazin-1-yl)-3,4-dihydroisoquinoline

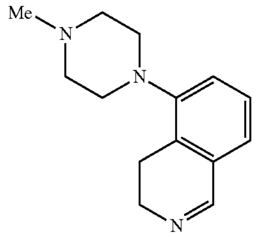 [SMILES: CN1CCN(c2cccc3c2CCN=C3)CC1]

Intermediate 19A: 5-(4-Methylpiperazin-1-yl)isoquinoline

To 5-(piperazin-1-yl) isoquinoline, HCl (0.28 g, 1.121 mmol) in MeOH (10 mL) was added sodium methoxide (1.026 mL, 4.48 mmol) and paraformaldehyde (0.040 g, 1.332 mmol). After 30 min, sodium borohydride (0.424 g, 11.21 mmol) was added to the above mixture. The reaction was quenched with 1N NaOH (15 mL) and extracted with EtOAc (3x30 mL). The combined organic layers were washed with brine (15 mL) and dried ($MgSO_4$) to afford 0.267 g of Intermediate 19A as yellow oil. MS (ESI) m/z: 228.1 $(M+H)^+$.

Intermediate 19: Intermediate 19A was reduced and then oxidized in a similar manner as described for Intermediate 17. MS (ESI) m/z: 230.0 $(M+H)^+$.

Intermediate 20

Ethyl 3-(4-(3,4-dihydroisoquinolin-5-yl)piperazine-1-carboxamido) propanoate

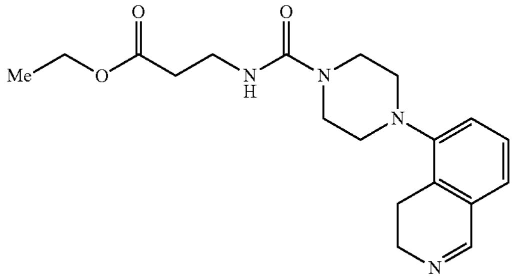 [SMILES: CCOC(=O)CCNC(=O)N1CCN(c2cccc3c2CCN=C3)CC1]

20A: Ethyl 3-(4-(isoquinolin-5-yl)piperazine-1-carboxamido)propanoate: To 5-(piperazin-1-yl)isoquinoline, HCl (0.216 g, 0.865 mmol) in DCM (5 mL) was added DIEA (0.302 mL, 1.730 mmol) and ethyl 3-isocyanatopropanoate (0.124 g, 0.865 mmol). The reaction was quenched with $H_2O$ (10 mL) and extracted with DCM (3x20 mL). The combined organic layers were washed with brine (10 mL) and dried ($MgSO_4$) which afforded Intermediate 20A as a white solid (0.39 g). MS (ESI) m/z: 357.0 $(M+H)^+$.

Intermediate 20: Intermediate 20A was reduced and then oxidized in a similar manner as described for Intermediate 18. MS (ESI) m/z: 359.0 $(M+H)^+$.

Intermediate 21 tert-butyl 4-(3,4-dihydroisoquinolin-5-yl)-3-oxopiperazine-1-carboxylate

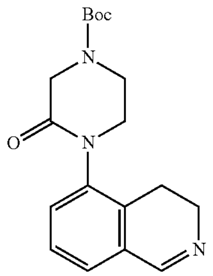 [SMILES: CC(C)(C)OC(=O)N1CCN(c2cccc3c2CCN=C3)C(=O)C1]

Intermediate 21A: tert-Butyl 4-(isoquinolin-5-yl)-3-oxopiperazine-1-carboxylate

To 5-bromoisoquinoline (0.3 g, 1.442 mmol) and tert-butyl 3-oxopiperazine-1-carboxylate (0.289 g, 1.442 mmol) was added DMSO (4 mL), 1,10-phenanthroline (0.026 g, 0.144 mmol) and $K_2CO_3$ (0.498 g, 3.60 mmol). The mixture was degassed for 10 min and then was added CuI (0.055 g, 0.288 mmol). The reaction was heated in a sealed tube in oil bath at 130° C. After 24 h, the reaction was incomplete. After cooling and degassing with argon, more CuI was added and heating was repeated. After 24 h, the reaction was quenched with dilute $NH_4OH$ (15 mL) and extracted with EtOAc (3×30 mL). The combined organic layers were washed with brine (15 mL) and dried ($MgSO_4$). The crude product was purified by normal phase chromatography followed by HPLC. After partitioning with saturated $NaHCO_3$ (15 mL) and EtOAc (50 mL), organic layer was washed with brine and dried ($MgSO_4$) to afford 0.157 g (54%) of Intermediate 21A as a white solid. MS (ESI) m/z: 328 $(M+H)^+$.

Intermediate 21 was prepared from Intermediate 21A as described for Intermediate 18. MS (ESI) m/z: 330.1 $(M+H)^+$.

Intermediate 22

1-(3,4-dihydroisoquinolin-5-yl)-4-methylpiperazin-2-one

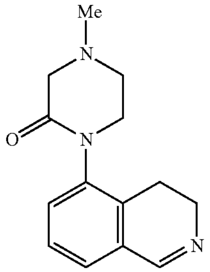 [SMILES: CN1CCN(c2cccc3c2CCN=C3)C(=O)C1]

Intermediate 22 was prepared in a similar manner as Intermediate 21 substituting 4-methylpiperazin-2-one for tert-butyl 3-oxopiperazine-1-carboxylate. MS (ESI) m/z: 244.1 $(M+H)^+$.

Intermediate 23

4-(3,4-dihydroisoquinolin-5-yl)morpholin-3-one

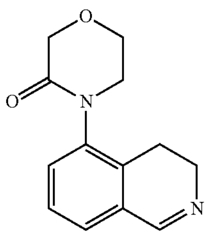 [SMILES: O=C1COCCN1c1cccc2c1CCN=C2]

Intermediate 23 was prepared in the same manner as Intermediate 22 substituting morpholin-3-one for tert-butyl 3-oxopiperazine-1-carboxylate. MS (ESI) m/z: 231.1 $(M+H)^+$.

Intermediate 24

5-Bromo-3,3-dimethyl-1,2,3,4-tetrahydroisoquinoline

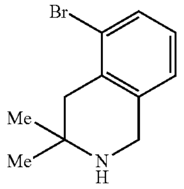 [SMILES: CC1(C)Cc2c(Br)cccc2CN1]

Intermediate 24A: 3-(2-Bromophenyl)-2,2-dimethylpropanenitrile

To a solution of isobutyronitrile (3.58 g, 52 mmol) in dry THF (30 mL) was added LiHMDS (1.0 M in THF) (80 mL, 80 mmol) at 0° C., stirred for 20 min, and to this solution was added 1-bromo-2-(bromomethyl)benzene (10 g, 40 mmol) in dry THF (70 mL). After 3 h at rt, the reaction mixture was quenched with saturated $NH_4Cl$ solution, extracted with EtOAc (2×), the combined organics were washed with $H_2O$, brine, dried over $Na_2SO_4$, filtered and concentrated to give 9.5 g (99%) of Intermediate 24A as red wine liquid. $^1H$ NMR (400 MHz, $CDCl_3$) δ 7.57-7.60 (2H, m), 7.30-7.34 (1H, m), 7.12-7.17 (1H, m), 3.08 (2H, s), 1.4 (6H, s) ppm.

Intermediate 24B: 3-(2-Bromophenyl)-2,2-dimethylpropanoic acid

To a solution of 24A (19 g, 79.83 mmol) in ethylene glycol (100 mL) was added potassium hydroxide pellets (20 g, 359.24 mmol) and the reaction was heated at 150° C. for 48 h. The reaction mixture was cooled, diluted with $H_2O$ and the aqueous layer was washed with EtOAc (2×). The aqueous layer was acidified with 1.5 N HCl, extracted with EtOAc (2×) and the combined organics were washed with $H_2O$, brine, dried over $Na_2SO_4$, filtered and concentrated. The crude product was then purified by silica gel column chromatography to give 18.0 g, (87.8%) of Intermediate 24B as a white solid. MS (ESI) m/z: 257 $(M+H)^+$.

Intermediate 24C: 1-Bromo-2-(2-isocyanato-2-methylpropyl)benzene

To a solution of Intermediate 24B (9.0 g, 35.0 mmol) in toluene (80 mL) at 0° C., was added TEA (4.7 mL, 33.2 mmol) and, slowly, diphenylphosphoryl azide (9.17 g, 33.2 mmol). After 45 min at 0° C., the reaction was heated to reflux for 4 h. The reaction mixture was cooled to rt, quenched with $H_2O$, and extracted with EtOAc (2×). The combined organics were washed with saturated $NaHCO_3$ solution, $H_2O$, brine, dried over $Na_2SO_4$, filtered and concentrated to give 8.0 g of Intermediate 24C as colorless liquid. $^1H$ NMR (400 MHz, $CDCl_3$) δ 7.37-7.59 (2H, m), 7.30 (1H, m), 7.14 (1H, m), 3.03 (2H, s), 1.41 (6H, s) ppm.

Intermediate 24D: Methyl 1-(2-bromophenyl)-2-methylpropan-2-ylcarbamate

To a stirred solution of Intermediate 24C (8.0 g, 31.5 mmol) in dry THF (80 mL) at 0° C., was added MeOH (5.0 mL, 157.5 mmol) and, slowly, NaH (60% in oil) (3.8 g, 94.5 mmol). After 3 h at rt, the reaction was quenched with ice cold water and extracted with EtOAc twice. The combined organics were washed with $H_2O$, brine, dried over $Na_2SO_4$, filtered and concentrated to give Intermediate 24D (8.5 g, 94.5%) as white solid. MS (ESI) m/z: 286.0 $(M+H)^+$.

Intermediate 24E: Methyl 5-bromo-3,3-dimethyl-3,4-dihydroisoquinoline-2(1H)-carboxylate To a solution of 24D (5.0 g, 17.5 mmol) in $AcOH/H_2SO_4$ (3:1; 15+5 mL) at 0° C. was, slowly, added paraformaldehyde (0.524 g, 17.5 mmol). After 48 h at rt, the reaction mixture was quenched with $H_2O$, extracted with EtOAc (2×). The combined organics were washed with saturated $NaHCO_3$ solution, $H_2O$, brine, dried over $Na_2SO_4$, filtered and concentrated to give 4.6 g of Intermediate 24E as a brown liquid. MS (ESI) m/z: 300.0 $(M+H)^+$.

Intermediate 24: 5-Bromo-3,3-dimethyl-1,2,3,4-tetrahydroisoquinoline

To a solution of Intermediate 24E (4.6 g) in ethylene glycol (50 mL) was added 50% aqueous KOH solution (23 mL) and the reaction was heated at 150° C. for 3 days. The reaction mixture was cooled, diluted with $H_2O$, extracted with EtOAc twice. The combined organics were extracted with 1.5 N HCl solution, the aqueous layer was basified with 10% NaOH solution, extracted with EtOAc twice and the combined organics were washed with $H_2O$, brine, dried over $Na_2SO_4$, filtered and concentrated to give Intermediate 24 (1.5 g, 39.4%) as a brown liquid. MS (ESI) m/z: 242.2 $(M+H)^+$.

Example 1

(E)-4-(2-(3-(5-chloro-2-(1H-tetrazol-1-yl)phenyl)acryloyl)-5-(piperazin-1-yl)-1,2,3,4-tetrahydroisoquinoline-1-carboxamido)benzoic acid, TFA

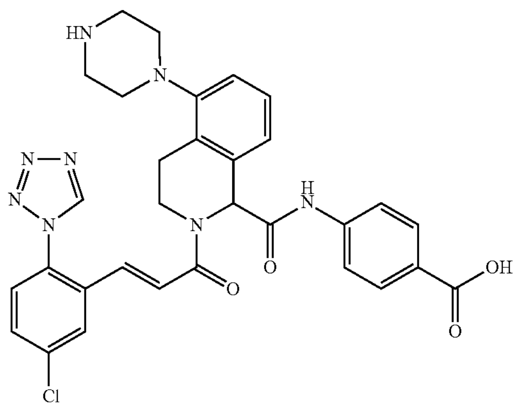 [SMILES: O=C(O)c1ccc(NC(=O)C2c3cccc(N4CCNCC4)c3CCN2C(=O)/C=C/c2cc(Cl)ccc2-n2cnnn2)cc1]

A mixture of Intermediate 18 (0.1 g, 0.317 mmol), Intermediate 6 (0.064 g, 0.317 mmol) and Intermediate 2 (0.079 g, 0.317 mmol) were heated in EtOH (3 mL) to reflux for 24 h. The reaction mixture was then cooled to rt and concentrated, followed by treatment with TFA/DCM to give the desired product as a yellow solid (0.018 g, 7.5%). $^1H$ NMR (400 MHz, DMSO-$d_6$) δ 12.64 (1H, br. s.), 10.68 (1H, s), 9.79 (1H, s), 8.60 (2H, br. s.), 8.32 (1H, d, J=2.02 Hz), 7.75-7.89 (2H, m), 7.63-7.71 (2H, m), 7.60 (1H, d, J=8.84 Hz), 7.43 (1H, d, J=15.41 Hz), 7.32 (1H, d, J=7.58 Hz), 7.20 (1H, t, J=7.83 Hz), 6.97 (1H, d, J=8.08 Hz), 6.91 (1H, d, J=15.41 Hz), 5.72 (1H, s), 4.23 (1H, d, J=5.56 Hz), 3.60-3.70 (1H, m), 3.21 (4H, br. s.), 2.85-3.11 (6H, m) ppm. MS (ESI) m/z: 613.1 $(M+H)^+$. Analytical HPLC: RT=5.54 min.

The following examples in Table 2 were made by the Ugi reaction as described in Example 1, using Intermediate 1, Intermediate 2 or Intermediate 3A; the corresponding imine intermediates, made in a similar manner as Intermediate 18, from commercially available piperazines and 5-bromoisoquinoline; and the appropriate isocyano benzoate intermediates.

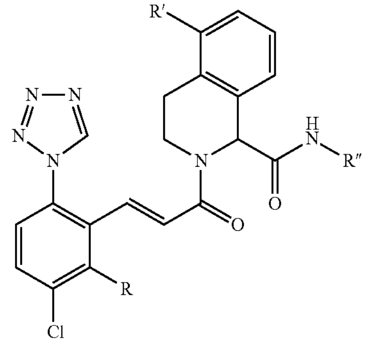

TABLE 2

| Example # | R | R' | R'' | M + H | RT |
|---|---|---|---|---|---|
| 2 | H | Piperazine | 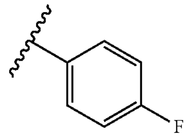 [SMILES: *c1ccc(F)cc1] | 587.0 | 5.54 |
| 3 | F | Piperazine | 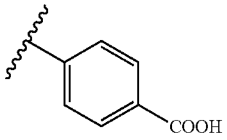 | 631.0 | 5.62 |
| 4 | F | Piperazine | 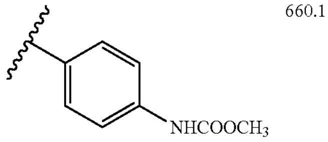 | 660.1 | 5.40 |
| 5 | F | Piperazine | 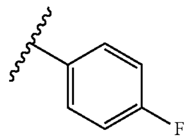 [SMILES: *c1ccc(F)cc1] | 605.1 | 6.06 |
| 6 | F | Piperazine | 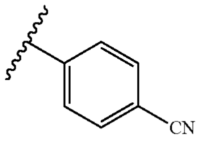 [SMILES: *c1ccc(C#N)cc1] | 612.1 | 5.88 |

TABLE 2-continued

| Example # | R | R' | R" | M + H | RT |
|---|---|---|---|---|---|
| 7 | F | Piperazine | 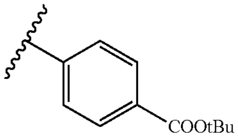 | 687.2 | 7.08 |
| 8 | F | Piperazine | 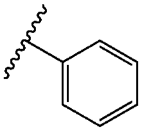 [SMILES: *c1ccccc1] | 587.3 | 5.93 |
| 9 | F | Piperazine | 6-indazole-1-CBz | 761.2 | 6.63 |
| 10 | F | Boc-piperazine | 6-indazole-1-tBoc | 827.1 | 12.14 |
| 11 | F | Piperazine | 6-indazole | 627.2 | 5.51 |

The following examples in Table 3 were obtained from HPLC chiral separation of corresponding examples, or their intermediates followed by deprotection, in Table 2.

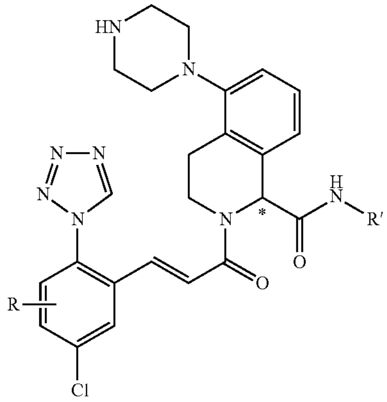

TABLE 3

| Example # | Stereochem | R | R' | M + H | RT |
|---|---|---|---|---|---|
| 12 | R enantiomer[a] | 2-F | 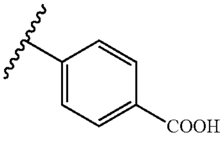 [SMILES: *c1ccc(C(=O)O)cc1] | 631.1 | 5.16 |
| 13 | S enantiomer[a] | 2-F | 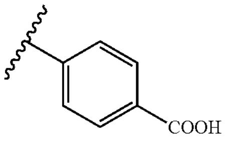 [SMILES: *c1ccc(C(=O)O)cc1] | 631.1 | 5.16 |
| 14 | S enantiomer[b] | 4-F | 6-indazole | 627.1 | 5.75 |
| 15 | R enantiomer[b] | 4-F | 6-indazole | 627.1 | 5.70 |
| 16 | R enantiomer[c] | 4-F | 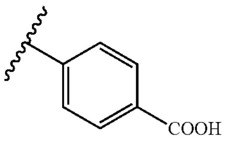 [SMILES: *c1ccc(C(=O)O)cc1] | 631.0 | 5.30 |
| 17 | S enantiomer[c] | 4-F | 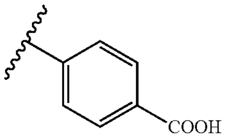 [SMILES: *c1ccc(C(=O)O)cc1] | 630.9 | 5.27 |

[a]Chiral HPLC Methods:
[a]Chiralcel OJ-H, 250 x 21 mm ID, 5 μm using 25/25/50 MeOH-IPA-Heptane-0.1% DEA, then 50/50 EtOH-IPA-0.1% DEA at 18 mL/min.
[b]Chiracel OD 5 cm x 50 cm column and 20% Heptane/80% (1:1 EtOH/MeOH) at 50 mL/min.
[c]Chiralpak AS-H, 2 x 15 cm using 30% IPA-0.1% DEA/$CO_2$ (100 bar) at 60 mL/min.

The following examples in Table 4 were made by the Ugi reaction, as shown in Example 1, using the corresponding imine intermediate such as Intermediates 18, 19 or 20 or an imine made in a similar manner as Intermediate 20 by substituting methyl chloroformate for ethyl 3-isocyanato-propanoate. The acids, Intermediates 1, 2 or 3A and the isonitriles, Intermediates 6, 7, 8, 9, 10, 11 or commercially available 1-fluoro-4-isocyanobenzene were used as required. Final deprotection of the t-butyl esters or carbamates with TFA/DCM yielded the final desired products as described previously.

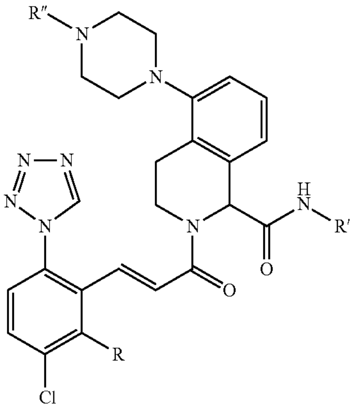

TABLE 4

| Example # | R | R' | R" | M + H | RT |
|---|---|---|---|---|---|
| 18 | F | -4-PhCOOH | $CH_3$ | 645.1 | 5.24 |
| 19 | H | -4-PhNHCOO $CH_3$ | $CH_3$ | 656.1 | 5.8 |
| 20 | F | -4-PhCN | $CH_3$ | 626.2 | 5.10* |

TABLE 4-continued

| Example # | R | R' | R" | M + H | RT |
|---|---|---|---|---|---|
| 21 | H | -4-PhCOOH | 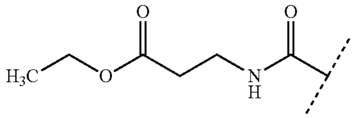 | 756.1 | 7.87 |
| 22 | H | -4-PhCOOH | $CH_3OOC$— | 671.1 | 8.49 |
| 23 | H | -4-PhNHCOO $CH_3$ | 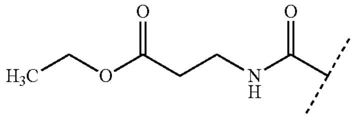 | 785.1 | 8.20 |
| 24 | F | -4-PhNHCOO $CH_3$ | $CH_3OOC$— | 660.1 | 5.43 |
| 25 | F | -4-PhF | $CH_3OOC$— | 663.4 | 9.50 |
| 26 | F | -4-PhCN | $CH_3OOC$— | 670.1 | 9.93 |
| 27 | F | 6-indazole | $CH_3$ | 641.2 | 6.21 |

*method B

The examples in Table 5 were made in a similar manner as Example 18 (Table 4) and separated by chiral HPLC.

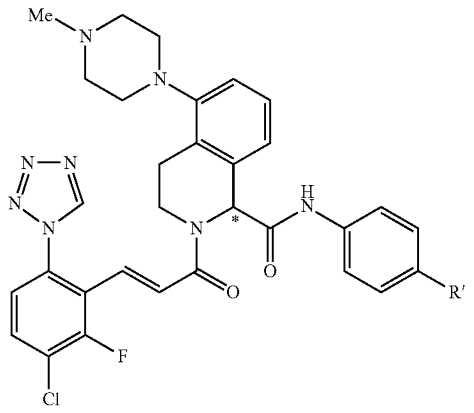

TABLE 5

| Example # | R' | Stereochemistry | M + H | RT |
|---|---|---|---|---|
| 28 | COOEt | R-enatiomer[a] | 673.3 | 6.47 |
| 29 | COOEt | S-enatiomer[a] | 673.3 | 6.46 |
| 30 | COOH | R-enatiomer[a] | 645.3 | 5.20 |
| 31 | COOH | S-enatiomer[a] | 645.3 | 5.20 |

[a]Chiralpak IA SFC (250 × 21 mm) using 40% EtOH-0.1% DEA/60% $CO_2$ at 60 mL/min, 150 bar, 35° C.

Example 32

(E)-4-(2-(3-(2-(Aminomethyl)-5-chlorophenyl)acryloyl)-5-(piperazin-1-yl)-1,2,3,4-tetrahydroisoquinoline-1-carboxamido)benzoic acid, tri TFA salt

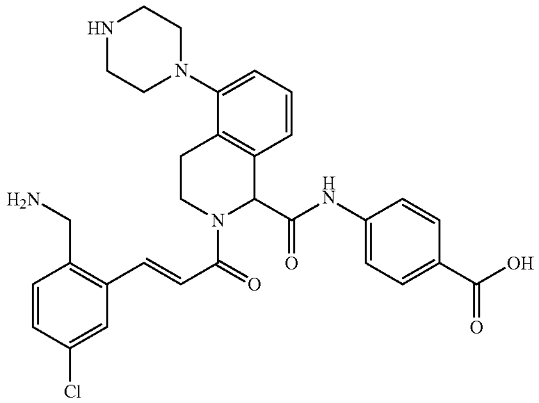 [SMILES: NCc1ccc(Cl)cc1/C=C/C(=O)N1CCc2c(cccc2N2CCNCC2)C1C(=O)Nc1ccc(C(=O)O)cc1]

Example 32 was prepared in a similar manner as Example 1, using Intermediate (E)-3-(2-((tert-butoxycarbonylamino)methyl)-5-chlorophenyl)acrylic acid in the Ugi reaction. $^1H$ NMR (400 MHz, MeOD) δ 7.98 (3H, d, J=8.84 Hz), 7.87 (1H, d, J=15.41 Hz), 7.69 (2H, d, J=8.84 Hz), 7.48-7.58 (2H, m), 7.29-7.45 (3H, m), 7.16 (1H, d, J=7.83 Hz), 5.86 (1H, s), 4.38-4.47 (1H, m), 4.30 (2H, s), 3.66-3.77 (1H, m), 3.38-3.52 (4H, m), 3.23-3.29 (4H, m), 3.15 (2H, d, J=177 Hz) ppm. MS (ESI) m/z: 574.1 $(M+H)^+$. Analytical HPLC: RT=3.55 min.

Example 33

(E)-4-(2-(3-(5-Chloro-2-(1H-tetrazol-1-yl)phenyl)acryloyl)-5-(2-oxopiperidin-1-yl)-1,2,3,4-tetrahydroisoquinoline-1-carboxamido)benzoic acid

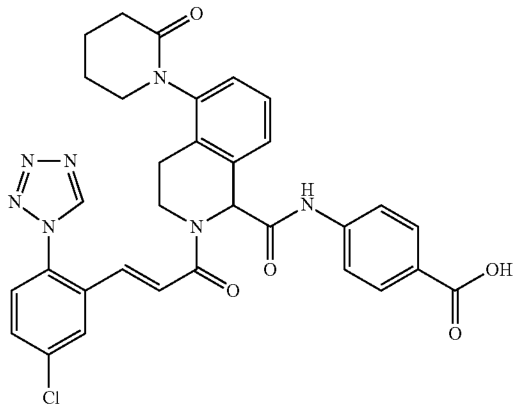 [SMILES: O=C(O)c1ccc(NC(=O)C2c3cccc(N4CCCCC4=O)c3CCN2C(=O)/C=C/c2cc(Cl)ccc2-n2cnnn2)cc1]

33A: 1-(Isoquinolin-5-yl)piperidin-2-one: To isoquinolin-5-amine (0.24 g, 1.665 mmol) in THF (5 mL) was added 5-bromopentanoyl chloride (0.223 mL, 1.665 mmol) followed by addition of THF (3 mL). The reaction was cooled with ice bath and to the above solution was added 1M KOtBu in THF (3.66 mL, 3.66 mmol). After 24 h, the reaction was quenched with $H_2O$ (10 mL) and extracted with EtOAc (3×20 mL). The combined organic layers were washed with brine (10 mL) and dried (Mg504) to afford 0.4 g of 33A as a dark solid. MS (ESI) m/z: 227 $(M+H)^+$.

33B: 1-(1,2,3,4-Tetrahydroisoquinolin-5-yl)piperidin-2-one: 33A was hydrogenated at 55 psi in EtOH (20 mL) in the presence of $PtO_2$ (30 mg). After 24 h, the reaction was filtered through Celite® and concentrated to afford 0.4 g of dark oil as desired product. MS (ESI) m/z: 231.3 $(M+H)^+$.

33C: 1-(3,4-Dihydroisoquinolin-5-yl)piperidin-2-one: 33B (0.38 g, 1.650 mmol) was oxidized with $MnO_2$ to afford 0.36 g of 33C as a dark oil. MS (ESI) m/z: 229.0 $(M+H)^+$.

Example 33 was made by the Ugi reaction combining 33C and Intermediates 2 and 6 as previously described for Example 1 followed by TFA deprotection. $^1H$ NMR (400 MHz, MeOD) δ 9.54 (1H, s), 8.17 (1H, t, J=2.78 Hz), 7.90-8.03 (2H, m), 7.61-7.73 (3H, m), 7.56-7.60 (1H, m), 7.52 (1H, d, J=7.83 Hz), 7.29-7.44 (2H, m), 7.14-7.27 (2H, m), 5.87-5.94 (1H, m), 4.19-4.32 (1H, m), 3.82-3.98 (1H, m), 3.63-3.73 (1H, m), 3.45-3.54 (1H, m), 2.98-3.11 (1H, m), 2.76-2.89 (1H, m), 2.50-2.62 (2H, m), 2.02 (4H, br. s) ppm. MS (ESI) m/z: 626.0 $(M+H)^+$. Analytical HPLC: RT=7.46 min.

The following examples in Table 6 were made by Ugi reaction as described in Example 1 using intermediate 33C and intermediates 1, 2, 3, 5 and 12 as appropriate. Deprotection with TFA/DCM was carried out where necessary. Single enantiomers were isolated by chiral HPLC.

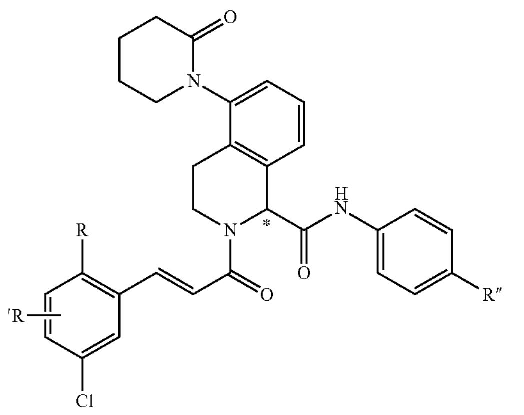

TABLE 6

| Example # | Stereochemistry | R | R' | R'' | M + H | RT |
|---|---|---|---|---|---|---|
| 34 | Racemic | tetrazole | 2-F | COOH | 644.1 | 7.50 |
| 35 | S-enantiomer[a] | tetrazole | 2-F | COOH | 644.1 | 7.62 |
| 36 | R-enantiomer[a] | tetrazole | 2-F | COOH | 644.1 | 7.69 |
| 37 | S-enantiomer[a] | tetrazole | 2-F | COOtBu | 700.1 | 10.65 |
| 38 | Racemic | —COMe | 2-F | COOH | 618.0 | 8.10 |
| 39 | R-enantiomer[a] | —COMe | 2-F | COOH | 618.0 | 5.68 |
| 40 | S-enantiomer[a] | —COMe | 2-F | COOH | 618.0 | 5.68 |
| 41 | R-enantiomer[b] | tetrazole | 4-F | COOH | 643.9 | 7.75 |
| 42 | S-enantiomer[b] | tetrazole | 4-F | COOH | 643.9 | 7.76 |
| 43 | Racemic | tetrazole | 2-F | COOEt | 672.3 | 9.35 |
| 44 | R-enantiomer[c] | tetrazole | 2-F | COOEt | 672.3 | 9.02 |
| 45 | S-enantiomer[c] | tetrazole | 2-F | COOEt | 672.3 | 9.06 |

[a]Chiral HPLC using Chiralcel OD 5 × 50 cm using 20% heptane and 80% (1:1MeOH/EtOH) at 50 mL/min.

[b]Chiralpak IA SFC, 150 × 30 mm using 55% EtOH-0.1% DEA/45% $CO_2$ at 70 mL/min, 100 Bar, 35° C.

[c]Chiralpak AD-H, 250 × 21 mm 30 mm using 45% (4:1 IPA-EtOH-0.1% DEA + 3% $H_2O$)/55% $CO_2$ at 60 mL/min, 100 Bar, 35° C.

The following examples in Table 7 were made by Ugi reaction as described in Example 1 using imine intermediates 19, 21, 22 or 23 and intermediates 6, 7, 8, 9, 10 or 11 as appropriate. Deprotection with TFA/DCM was carried out where necessary. Single enantiomers were isolated by chiral HPLC at a protected late stage intermediate and then, deprotected where indicated.

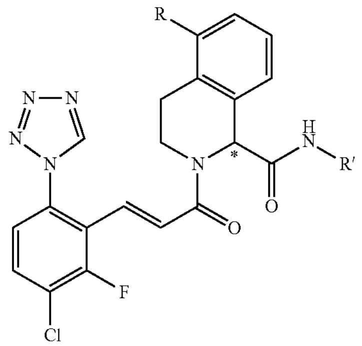

TABLE 7
| Example # | Stereochemistry | R | R' | M + H | RT |
|---|---|---|---|---|---|
| 46 | Racemic | 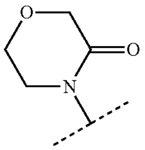 | -4-PhCOOH | 646.0 | 7.04 |
| 47 | Racemic | 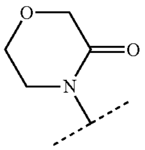 | 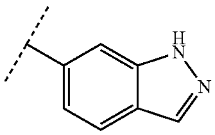 | 642.6 | 7.15 |
| 48 | R-enantiomer[a] | 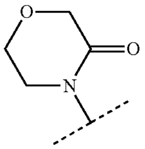 | -4-PhCOOH | 646.0 | 7.15 |
| 49 | S-enantiomer[a] | 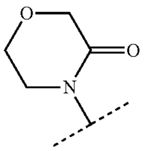 | -4-PhCOOH | 646.0 | 7.15 |
| 50 | S-enantiomer[a] | 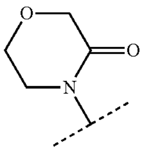 | -4-PhCOOtBu | 701.9 | 9.90 |
| 51 | Racemic | 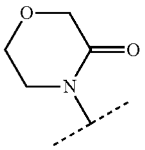 | -4-PhCOOEt | 674.0 | 8.61 |
| 52 | Racemic | 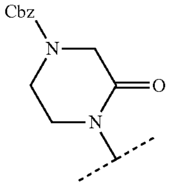 | -4-PhCOOH | 779.1 | 8.76 |
| 53 | Racemic | 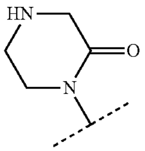 | 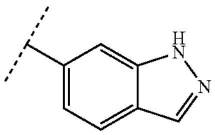 | 655.2 | 5.28 |
| 54 | Racemic | 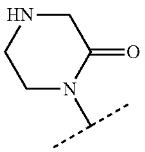 | -4-PhCOOH | 645.0 | 5.20 |

TABLE 7-continued
| Example # | Stereochemistry | R | R' | M + H | RT |
|---|---|---|---|---|---|
| 55 | Racemic | 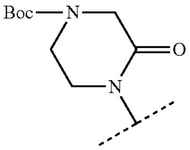 | -4-PhCOOtBu | 801.5 | 11.25 |
| 56 | Racemic | 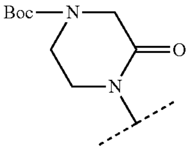 | -4-PhCOOEt | 773.5 | 10.3 |
| 57 | Racemic | 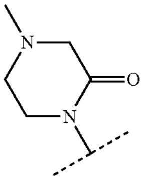 | -4-PhCOOtBu | 715.3 | 6.82 |
| 58 | Racemic | 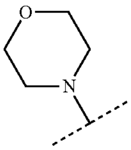 | -4-PhNHCOOCH$_3$ | 661.0 | 9.33 |
| 59 | Racemic | 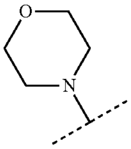 | -4-PhCOOtBu | 688.3 | 10.8 |
| 60 | Racemic | 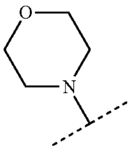 | 4-PhCOOH | 632.2 | 8.40 |
| 61 | R-enantiomer[b] | 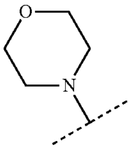 | 4-PhCOOH | 632.3 | 8.44 |
| 62 | S-enantiomer[b] | 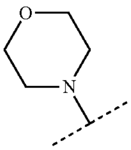 | 4-PhCOOH | 632.3 | 8.44 |
| 63 | Racemic | 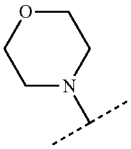 | -4-PhCOOEt | 660.3 | 10.6 |

TABLE 7-continued

| Example # | Stereochemistry | R | R' | M + H | RT |
|---|---|---|---|---|---|
| 64 | Diastereomer | 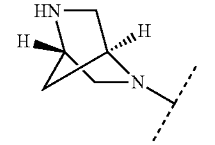 | 4-PhCOOH | 643.2 | 5.49 |

[a]Chiracel OD 5 x 50 cm using 20% Heptane/80% 1:1 EtOH/MeOH at 50 mL/min.
[b]Chiralpak 250 x 21 mm, using AD-H using 45% (1:1EtOH-IPA-0.1%DEA)/55% $CO_2$ at 60 mL/min, 100 bar, 35° C.

Example 65

(E)-4-(2-(3-(5-chloro-4-fluoro-2-(1H-tetrazol-1-yl) phenyl)acryloyl)-5-(piperazin-1-yl)-1,2,3,4-tetrahydroisoquinoline-1-carboxamido)benzoic acid, bis TFA Salt

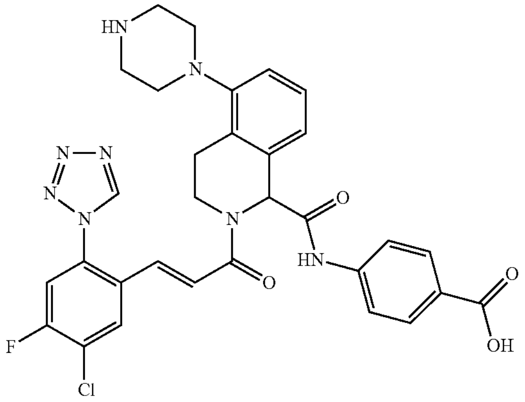 [SMILES: O=C(O)c1ccc(NC(=O)C2c3cccc(N4CCNCC4)c3CCN2C(=O)/C=C/c2cc(Cl)c(F)cc2-n2cnnn2)cc1]

Example 65 was prepared in a similar manner as Example 1 substituting Intermediate 5 for Intermediate 2. $^1H$ NMR (500 MHz, MeOD) δ 10.22-10.48 (1H, m), 9.37-9.51 (1H, m), 8.11-8.28 (1H, m), 7.75-7.96 (2H, m), 7.45-7.66 (2H, m), 7.15-7.34 (2H, m), 6.97-7.18 (3H, m), 5.63-5.75 (1H, m), 4.09-4.32 (2H, m), 3.48-3.61 (2H, m), 3.24-3.43 (4H, m), 2.97-3.19 (4H, m) ppm. MS (ESI) m/z: 631 $(M+H)^+$. Analytical HPLC: RT=5.55 min.

Example 66

(E)-N-(4-carbamoylphenyl)-2-(3-(5-chloro-4-fluoro-2-(1H-tetrazol-1-yl)phenyl)acryloyl)-5-(piperazin-1-yl)-1,2,3,4-tetrahydroisoquinoline-1-carboxamide, bis-TFA Salt

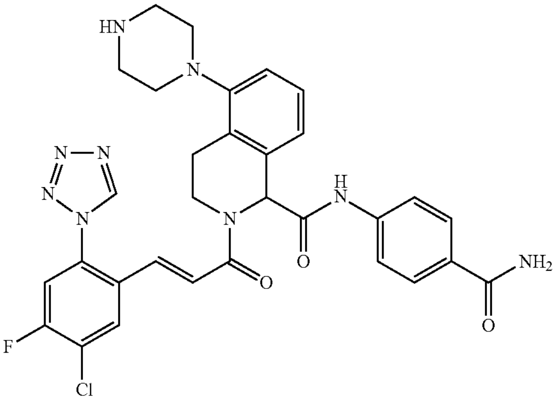 [SMILES: NC(=O)c1ccc(NC(=O)C2c3cccc(N4CCNCC4)c3CCN2C(=O)/C=C/c2cc(Cl)c(F)cc2-n2cnnn2)cc1]

66A: (E)-tert-butyl 4-(1-(4-carbamoylphenylcarbamoyl)-2-(3-(5-chloro-4-fluoro-2-(1H-tetrazol-1-yl)phenyl)acryloyl)-1,2,3,4-tetrahydroisoquinolin-5-yl)piperazine-1-carboxylate: To Boc-protected Compound 65 (piperazine as Boc protected) (0.2 g, 0.274 mmol) in DMF (2 mL) was added ammonium chloride (0.022 g, 0.410 mmol), PyBOP (0.142 g, 0.274 mmol) and DIEA (0.072 mL, 0.410 mmol). After 24 h, the reaction was partitioned with $H_2O$ (15 mL) and EtOAc (40 mL). The organic layer was washed with $H_2O$ (2×10 mL), 10% LiCl (10 mL), brine (10 mL) and dried ($MgSO_4$). MS (ESI) m/z: 730.0 $(M+H)^+$.

Example 66: 66A was deprotected with 30% TFA/DCM (10 mL). After 2 h, the reaction was concentrated and purified by reverse phase HPLC and freeze-dried to afford 4.6 mg (1.8%) of example 66 as a tan solid. $^1H$ NMR (400 MHz, MeOD) δ 9.46 (1H, s), 8.14-8.26 (1H, m), 7.72 (2H, d, J=8.84 Hz), 7.49-7.63 (4H, m), 7.17-7.30 (2H, m), 7.00-7.14 (2H, m), 5.69 (1H, s), 4.14-4.28 (1H, m), 3.50-3.67 (1H, m), 3.27-3.42 (4H, m), 2.99-3.17 (6H, m) ppm. MS (ESI) m/z: 630.0 $(M+H)^+$. Analytical HPLC: RT=5.26 min.

The examples in Table 8 were prepared in a similar manner as Example 66 using the appropriate amines in place of ammonium chloride.

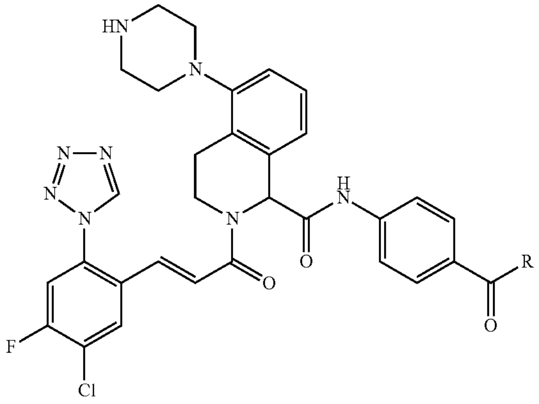

TABLE 8

| Example # | R | M + H | RT |
|---|---|---|---|
| 67 | Cyclopropanamine | 670.07 | 1.87* |
| 68 | 2-(1H-imidazol-4-yl)ethanamine | 724.13 | 1.66* |
| 69 | Aniline | 706.11 | 2.25* |
| 70 | N-(4-aminophenyl)acetamide | 763.26 | 1.88* |
| 71 | Ethyl | 658.11 | 1.85* |
| 72 | N-(2-aminoethyl)acetamide | 715.23 | 1.67* |
| 73 | 3-aminoprop anamide | 701.14 | 1.64* |
| 74 | methyl 2-aminoacetate | 702.12 | 1.83* |
| 75 | 3-methoxyaniline | 736.20 | 2.30* |

TABLE 8-continued

| Example # | R | M + H | RT |
|---|---|---|---|
| 76 | Dimethylamine | 658.1 | 5.52 |
| 77 | Methylamine | 643.9 | 5.38 |

*Column used: Supelco Ascentis Express 4.6 x 50 mm 2.7 uM C18. Mobile Phase: A = 5:95 Acetonitrile: $H_2O$; B = 95:5 Acetrile: $H_2O$; Modifier = 0.05% TFA Wavelength: 220 nm. The remaining samples used method A.

Example 78

(E)-4-(2-(3-(3-chloro-2-fluoro-6-(1H-tetrazol-1-yl) phenyl)acryloyl)-3,3-dimethyl-5-(piperazin-1-yl)-1, 2,3,4-tetrahydroisoquinoline-1-carboxamido)benzoic acid, bis-TFA Salt

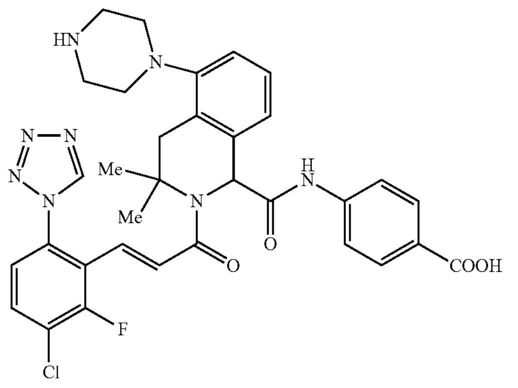 [SMILES: CC1(C)Cc2c(cccc2N2CCNCC2)C(C(=O)Nc2ccc(C(=O)O)cc2)N1C(=O)/C=C/c1c(-n2cnnn2)ccc(Cl)c1F]

78A: Benzyl 5-bromo-3,3-dimethyl-3,4-dihydroisoquinoline-2 (1H)-carboxylate: To intermediate 24 (900 mg, 3.75 mmol) in dry THF (9 mL), at 0° C., was added 10% aqueous NaOH (5.4 mL) followed by drop-wise addition of benzyl chloroformate (0.6 mL, 4.12 mmol). After 48 h, the reaction was quenched with ice cold $H_2O$, extracted with EtOAc (2×), the combined organics were washed with $H_2O$, brine, dried over $Na_2SO_4$ and concentrated. Purification by silica gel column chromatography afforded 78A (0.6 g, 42.8%) as a white liquid. MS (ESI) m/z: 347.0 $(M+H)^+$.

78B: Benzyl 5-(4-(tert-butoxycarbonyl)piperazin-1-yl)-3, 3-dimethyl-3,4-dihydroisoquinoline-2 (1H)-carboxylate: To 78A (600 mg, 1.60 mmol) in toluene (5 mL) was added NaOtBu (215 mg, 2.24 mmol), tert-butyl piperazine-1-carboxylate (358 mg, 1.92 mmol), $Pd_2(dba)_3$ (3.6 mg, 0.004 mmol) and BINAP (7.4 mg, 0.012 mmol). The reaction mixture was heated at 100° C. in a sealed tube. After 18 h, the reaction was cooled to rt, quenched with $H_2O$, extracted with EtOAc twice, the combined organics were washed with $H_2O$, brine, dried over anhydrous $Na_2SO_4$, filtered and concentrated. Purification by silica gel column chromatography afforded 78B (500 mg, 67%) as a green liquid. MS (ESI) m/z: 480.4 $(M+H)^+$.

78C: tert-Butyl-4-(3,3-dimethyl-1,2,3,4-tetrahydroisoquinolin-5-yl)piperazine-1-carboxylate: To 78B (340 mg) in EtOH (4 mL) was added 10% Pd/C (68 mg, 20 vol) and the reaction was hydrogenated under 14 psi of $H_2$. After 3 h, the reaction was filtered through Celite® and washed twice with MeOH. The combined organics were evaporated to afford 78C (170 mg, 69.6%) as a white solid. MS (ESI) m/z: 346.2 $(M+H)^+$.

78D: tert-Butyl-4-(3,3-dimethyl-3,4-dihydroisoquinolin-5-yl)piperazine-1-carboxylate: To a solution of 78C (170 mg, 0.49 mmol) in EtOH (2 mL) was added iodine (281 mg, 2.21 mmol) and NaOAc (60 mg, 0.73 mmol) and the reaction mixture was heated to 80° C. After 3 h, the solvent was evaporated and the residue was quenched with 10% sodium thiosulphate solution and extracted twice with EtOAc and the combined organics were washed with $H_2O$. The organic layer was extracted with 2 mL of 0.5 N HCl solution and the combined aqueous layers were basified with ammonia solution and extracted with EtOAc twice. The combined organics were washed with $H_2O$, brine and dried over $Na_2SO_4$, filtered and concentrated to give 78D (90 mg, 53.2%). MS (ESI) m/z: 344.2 $(M+H)^+$.

Example 78 was prepared in an Ugi reaction in a similar manner as Example 1 using 78D, Intermediate 3, and Intermediate 6 followed by TFA deprotection and HPLC purification. $^1H$ NMR (400 MHz, DMSO-$d_6$) δ 12.77 (1H, s), 10.48 (1H, s), 9.86 (1H, s), 8.63 (2H, bs), 7.88-7.97 (3H, m), 7.66 (3H, d, J=8.8 Hz), 7.53 (1H, d, J=7.6 Hz), 7.29 (1H, t, J=8.0 Hz), 7.07-7.11 (3.0H, m), 5.74 (1H, bs), 3.20-3.23 (2H, m), 3.06-3.10 (2H, m), 2.94 (3H, bs), 1.81 (3H, s), 1.11 (3H, s) ppm. LCMS m/z: 659.4 $(M+H)^+$. Analytical HPLC: RT=7.62 min.

Example 79

(E)-4-(2-(3-(6-acetyl-3-chloro-2-fluorophenyl)acryloyl)-5-(4-methylpiperazin-1-yl)-1,2,3,4-tetrahydroisoquinoline-1-carboxamido)benzoic acid, bis-TFA Salt

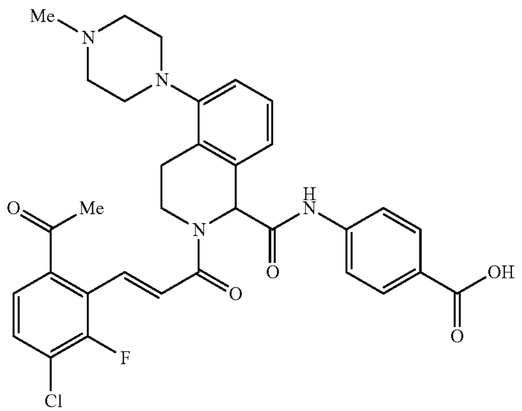 [SMILES: CC(=O)c1ccc(Cl)c(F)c1/C=C/C(=O)N1CCc2c(cccc2N2CCN(C)CC2)C1C(=O)Nc1ccc(C(=O)O)cc1]

Example 79 was prepared in a similar manner as Example 1 using Intermediate 19, Intermediate 6 and Intermediate 12 followed by TFA deprotection. $^1H$ NMR (500 MHz, DMSO-$d_6$) δ 10.83 (1H, s), 9.51-9.65 (1H, m), 7.88 (2H, d, J=8.80 Hz), 7.73-7.79 (1H, m), 7.70 (2H, d, J=8.80 Hz), 7.56 (1H, d, J=15.68 Hz), 7.44 (1H, d, J=7.70 Hz), 7.28 (1H, t, J=7.84 Hz), 7.03-7.12 (2H, m), 5.85 (1H, s), 4.21 (1H, ddd, J=12.04, 5.16, 4.81 Hz), 3.59-3.67 (1H, m), 3.47-3.56 (2H, m), 3.18-3.31 (5H, m), 3.09-3.17 (1H, m), 2.99-3.05 (2H, m), 2.85-2.93 (4H, m), 2.59 (3H, s) ppm. MS (ESI) m/z: 619 $(M+H)^+$. Analytical HPLC: RT=5.0 min.

Example 80

(E)-4-(2-(3-(3-Chloro-2-fluoro-6-(1H-tetrazol-1-yl)phenyl)acryloyl)-5-(4-(pyrrolidin-1-yl)piperidin-1-yl)-1,2,3,4-tetrahydroisoquinoline-1-carboxamido)benzoic acid, bis TFA Salt

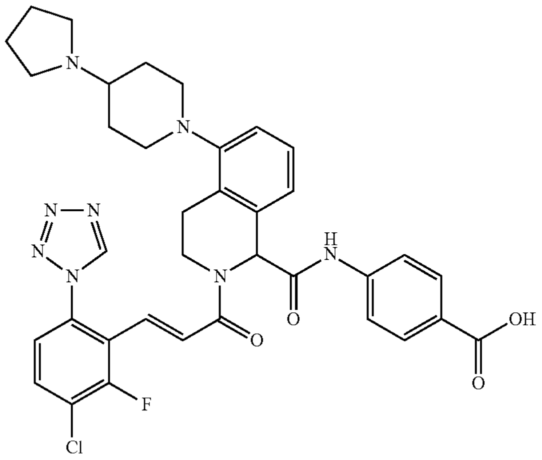 [SMILES: O=C(O)c1ccc(NC(=O)C2c3cccc(N4CCC(N5CCCC5)CC4)c3CCN2C(=O)/C=C/c2c(-n3cnnn3)ccc(Cl)c2F)cc1]

80A: 5-(4-(Pyrrolidin-1-yl)piperidin-1-yl)isoquinoline: To 5-bromoisoquinoline (1 g, 4.81 mmol), 4-(pyrrolidin-1-yl)piperidine (1.112 g, 7.21 mmol), and sodium tert-butoxide (0.647 g, 6.73 mmol), was added toluene (10 mL) and the mixture was degassed with argon. BINAP (0.090 g, 0.144 mmol) and $Pd_2(dba)_3$ (0.044 g, 0.048 mmol) were added and the reaction was heated to 130° C. in a microwave for 20 min. Purification by normal phase chromatography afforded 0.84 g (62.7%) of 80A as a tan solid. MS (ESI) m/z: 282.1 $(M+H)^+$.

80B: 5-(4-(Pyrrolidin-1-yl)piperidin-1-yl)-3,4-dihydroisoquinoline: 80A was hydrogenated in the presence of $PtO_2$ and then oxidized with $MnO_2$ to afford 0.85 g (62.8%) of 80B as a yellow oil. MS (ESI) m/z: 284.2 $(M+H)^+$.

Example 80 was prepared by the Ugi reaction as in Example 1 using 80B and Intermediates 3A and 6 followed by TFA deprotection. $^1$H NMR (400 MHz, MeOD) δ 9.56 (1H, s), 7.95 (2H, d, J=8.59 Hz), 7.72-7.85 (1H, m), 7.64 (2H, dd, J=8.72, 1.39 Hz), 7.49 (1H, dd, J=8.72, 1.39 Hz), 7.23-7.42 (2H, m), 7.14-7.23 (1H, m), 7.07 (1H, d, J=7.58 Hz), 6.91-7.05 (1H, m), 5.76 (1H, s), 4.12 (1H, ddd, J=11.75, 4.67, 4.55 Hz), 3.72 (2H, br. s.), 3.41-3.57 (1H, m), 3.07-3.32 (7H, m), 2.90 (1H, t, J=11.24 Hz), 2.57-2.71 (1H, m), 2.14-2.38 (4H, m), 1.83-2.11 (4H, m) ppm. MS (ESI) m/z: 699.4 $(M+H)^+$. Analytical HPLC: RT=5.51 min.

The following examples in Table 9 were prepared in a similar manner as Example 80 starting with the appropriate substituted piperidine and isonitriles (Intermediates 6, 7, 8, 9, 10 or 11 or commercial). Chiral separation was carried out using chiral HPLC on late stage intermediates followed by deprotection and purification where indicated.

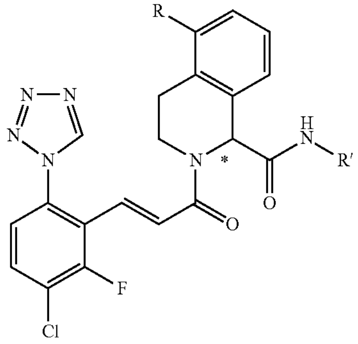

TABLE 9

| Example # | stereochemistry | R | R' | M + H | RT |
|---|---|---|---|---|---|
| 81 | Racemic | 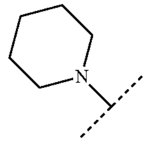 | -4-PhCOOH | 630.3 | 7.46 |
| 82 | Racemic | 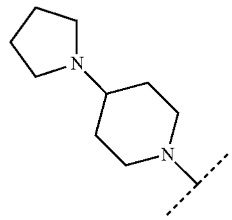 | -4-Ph—F | 673.4 | 6.83 |
| 83 | Racemic | 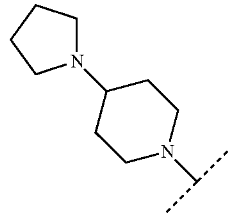 | -4-PhCOOEt | 727.4 | 6.70 |

TABLE 9-continued
| Example # | stereochemistry | R | R' | M + H | RT |
|---|---|---|---|---|---|
| 84 | Racemic | 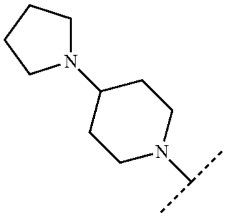 | -4-PhCOOtBu | 755.4 | 8.73 |
| 85 | Racemic | 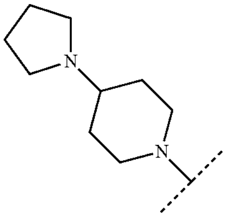 | 4-PhCN | 680.4 | 6.47 |
| 86 | S-enantiomer[a] | 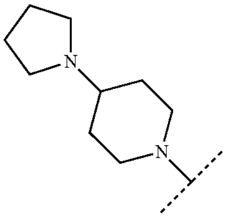 | -4-Ph—F | 673.5 | 6.69 |
| 87 | S-enantiomer[a] | 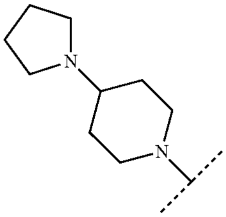 | -4-PhCOOH | 699.4 | 5.90 |
| 88 | R-enantiomer[a] | 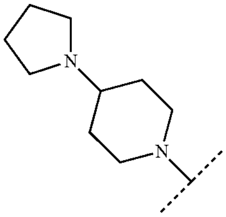 | -4-PhCOOH | 699.4 | 5.91 |
| 89 | Racemic | 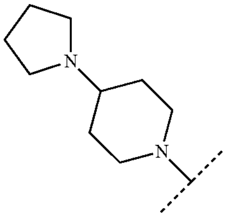 | -4-PhNHCOOCH$_3$ | 728.5 | 6.10 |
| 90 | R-enantiomer[a] | 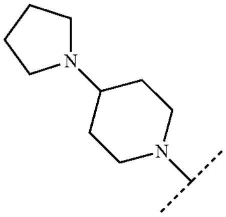 | -4-Ph—F | 673.5 | 6.85 |

TABLE 9-continued
| Example # | stereochemistry | R | R' | M + H | RT |
|---|---|---|---|---|---|
| 91 | Racemic | 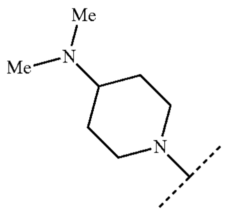 | -4-PhCOOtBu | 729.5 | 7.28 |
| 92 | Racemic | 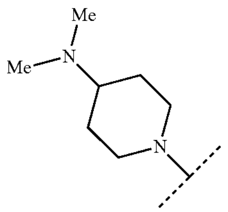 | -4-PhCOOH | 673.5 | 5.65 |
| 93 | R-enantiomer[b] | 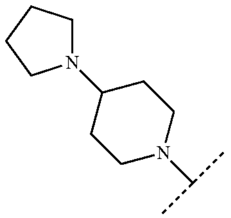 | -4-Ph—COOEt | 727.6 | 6.88 |
| 94 | S-enantiomer[b] | 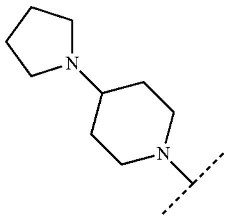 | -4-Ph—COOEt | 727.6 | 6.85 |
| 95 | Racemic | 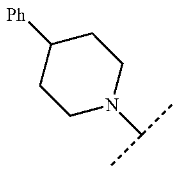 | -4-PhCOOH | 706.3 | 9.61 |
| 96 | Racemic | 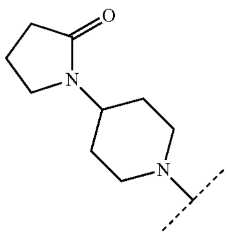 | -4-PhCOOH | 713.3 | 7.45 |
| 97 | Racemic | 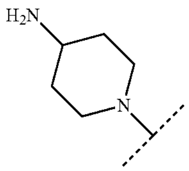 | -4-PhCOOH | 645.4 | 5.19 |

TABLE 9-continued
| Example # | stereochemistry | R | R' | M + H | RT |
|---|---|---|---|---|---|
| 98 | R-enantiomer[c] | 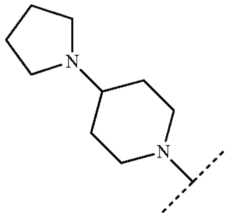 | -4-PhNHCOOCH$_3$ | 728.6 | 5.84 |
| 99 | S-enantiomer[c] | 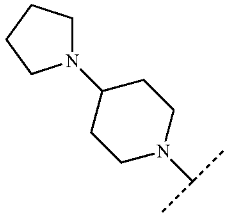 | -4-PhNHCOOCH$_3$ | 728.6 | 5.89 |
| 100 | Racemic | 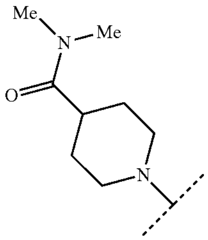 | -4-PhCOOH | 701.2 | 7.20 |
| 101 | S-enantiomer[h] | 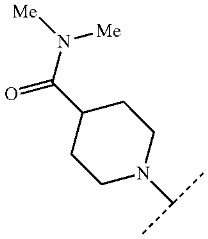 | -4-PhCOOH | 701.2 | 7.26 |
| 102 | R-enantiomer[a] | 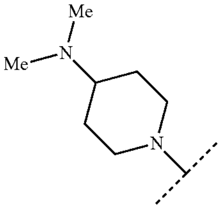 | -4-PhCOOH | 673.5 | 5.39 |
| 103 | S-enantiomer[a] | 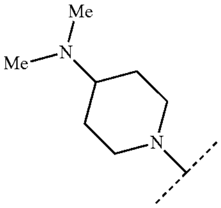 | -4-PhCOOH | 673.5 | 5.37 |
| 104 | Racemic | 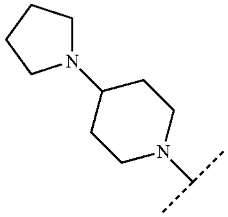 | -4-Ph—Cl | 689.5 | 6.94 |

TABLE 9-continued
| Example # | stereochemistry | R | R' | M + H | RT |
|---|---|---|---|---|---|
| 105 | Racemic | 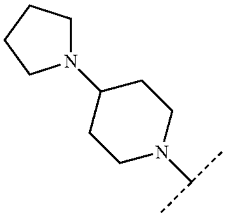 | -4-PhCOOnBu | 755.6 | 7.65 |
| 106 | Racemic | 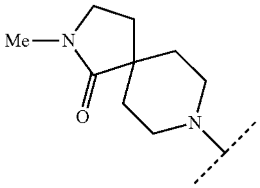 | -4-PhCOOH | 713.5 | 7.02 |
| 107 | R-enantiomer[e] | 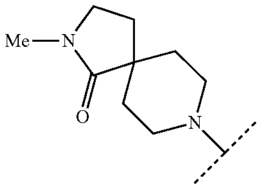 | -4-PhCOOH | 713.5 | 6.98 |
| 108 | S-enantiomer[e] | 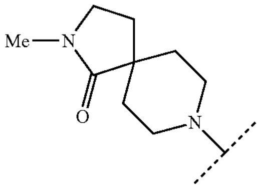 | -4-PhCOOH | 713.5 | 6.97 |
| 109 | Racemic | 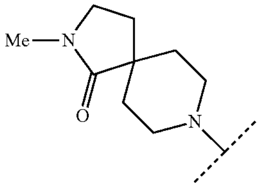 | -4-PhCOOEt | 741.6 | 8.45 |
| 110 | S-enantiomer | 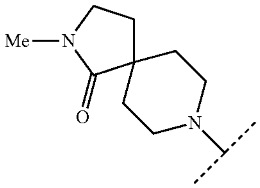 | -4-PhCOOEt | 741.3 | 9.20 |
| 111 | R-enantiomer[a] | 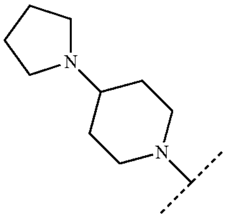 | -4-Ph—Cl | 689.5 | 7.36 |

TABLE 9-continued
| Example # | stereochemistry | R | R' | M + H | RT |
|---|---|---|---|---|---|
| 112 | S-enantiomer[a] | 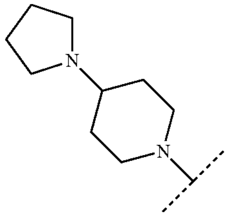 | -4-Ph—Cl | 689.5 | 6.95 |
| 113 | R-enantiomer[a] | 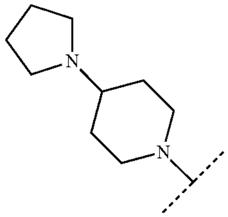 | -4-PhCOOnBu | 755.6 | 8.03 |
| 114 | S-enantiomer[a] | 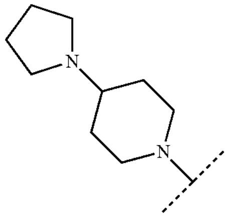 | -4-PhCOOnBu | 755.7 | 8.05 |
| 115 | Racemic | 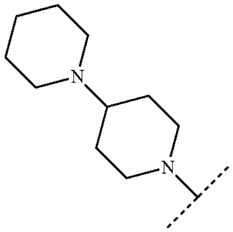 | -4-PhCOOH | 713.5 | 6.70 |
| 116 | Racemic | 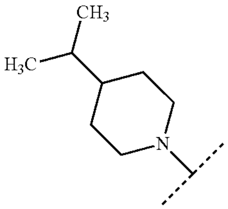 | -4-PhCOOH | 672.5 | 9.62 |
| 117 | Racemic | 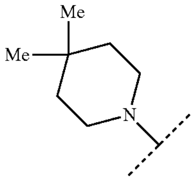 | 4-PhCOOH | 658.5 | 9.21 |
| 118 | R-enantiomer[c] | 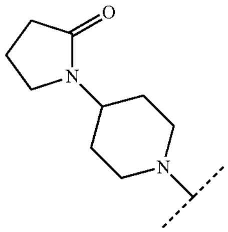 | -4-PhCOOH | 713.5 | 7.27 |

TABLE 9-continued
| Example # | stereochemistry | R | R' | M + H | RT |
|---|---|---|---|---|---|
| 119 | S-enantiomer[c] | 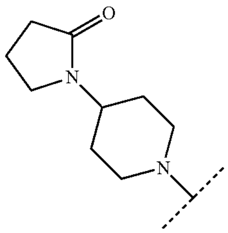 | -4-PhCOOH | 713.5 | 7.82 |
| 120 | Racemic | 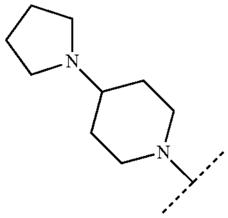 | 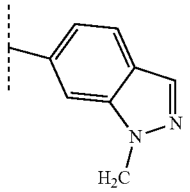 | 709.3 | 5.76 |
| 121 | Racemic | 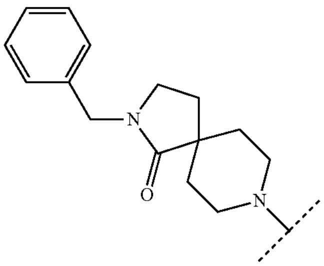 | -4-PhCOOH | 789.6 | 8.55 |
| 122 | Racemic | 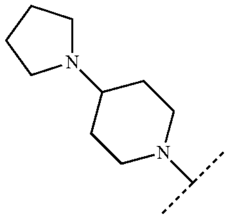 | -4-PhCOOiPr | 741.6 | 7.26 |
| 123 | Racemic | 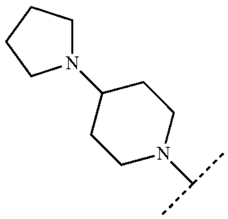 | -4-PhCOOiBu | 755.6 | 7.69 |
| 124 | Racemic | 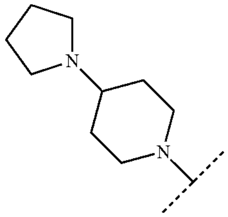 | 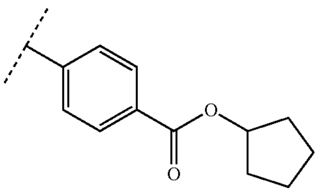 | 767.6 | 7.61 |

TABLE 9-continued
| Example # | stereochemistry | R | R' | M + H | RT |
|---|---|---|---|---|---|
| 125 | R-enantiomer[d] | 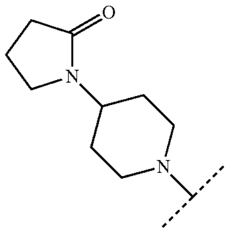 | -4-Ph—COOEt | 741.5 | 9.13 |
| 126 | S-enantiomer[d] | 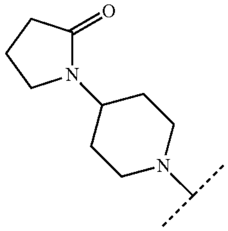 | -4-Ph—COOEt | 741.5 | 9.09 |
| 127 | Racemic | 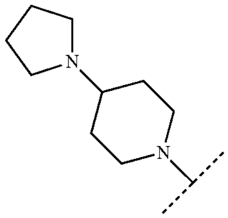 | 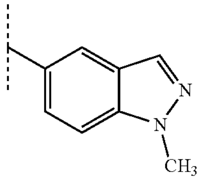 | 709.6 | 7.01 |
| 128 | R-enantiomer[e] | 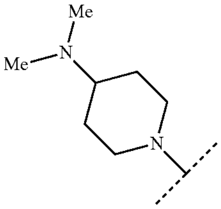 | -4-PhCOOEt | 701.5 | 7.45 |
| 129 | S-enantiomer[e] | 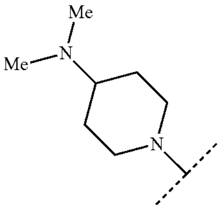 | -4-PhCOOEt | 701.5 | 7.45 |
| 130 | Racemic | 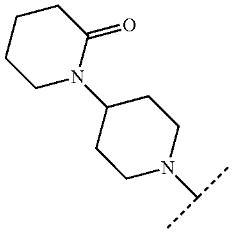 | -4-PhCOOH | 727.5 | 8.86 |

TABLE 9-continued
| Example # | stereochemistry | R | R' | M + H | RT |
|---|---|---|---|---|---|
| 131 | Racemic | 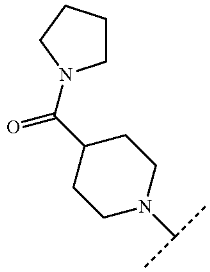 | -4-PhCOOH | 727.5 | 8.37 |
| 132 | R-enantiomer[f] | 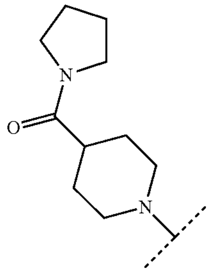 | -4-PhCOOH | 727.6 | 7.08 |
| 133 | S-enantiomer[f] | 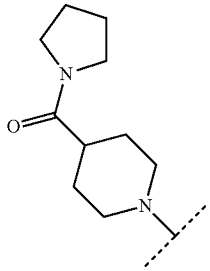 | -4-PhCOOH | 727.6 | 10.69 ? |
| 134 | Racemic | 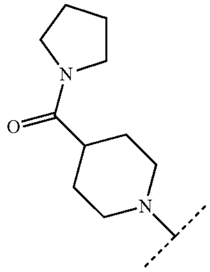 | -4-PhCOOEt | 755.5 | 8.56 |
| 135 | S-enantiomer[f] | 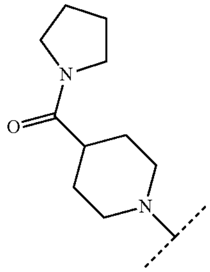 | -4-PhCOOEt | 755.3 | 9.3 |

TABLE 9-continued
| Example # | stereochemistry | R | R' | M + H | RT |
|---|---|---|---|---|---|
| 136 | Racemic | 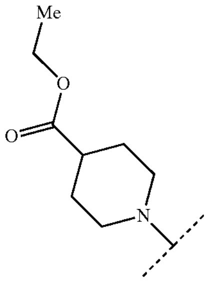 | -4-PhCOOH | 702.0 | 13.02 |
| 137 | Racemic | 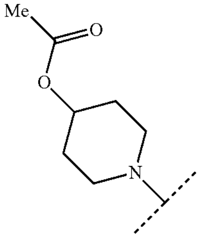 | -4-PhCOOH | 688.3 | 10.47 |
| 138 | Racemic | 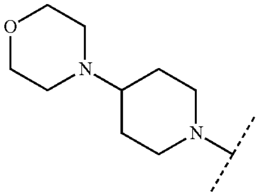 | -4-PhCOOH | 715.3 | 6.19 |
| 139 | S-enantiomer[k] | 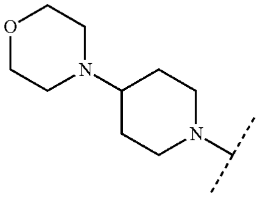 | -4-PhCOOH | 715.4 | 6.20 |
| 140 | Racemic | 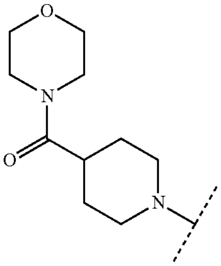 | -4-PhCOOH | 743.3 | 6.75 |
| 141 | S-enantiomer[f] | 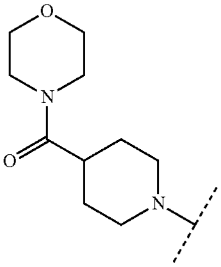 | -4-PhCOOH | 743.3 | 7.24 |

TABLE 9-continued
| Example # | stereochemistry | R | R' | M + H | RT |
|---|---|---|---|---|---|
| 142 | Racemic | 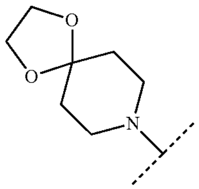 | -4-PhCOOH | 688.4 | 10.36 |
| 143 | S-enantiomer[g] | 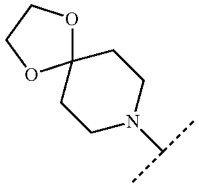 | -4-PhCOOH | 688.2 | 9.33 |
| 144 | S-enantiomer | 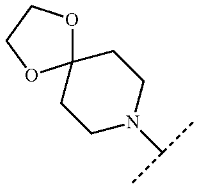 | -4-PhCOOMe | 702.3 | 2.18** |
| 145 | Racemic | 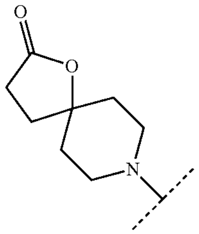 | -4-PhCOOH | 700.2 | 8.75 |
| 146 | Racemic | 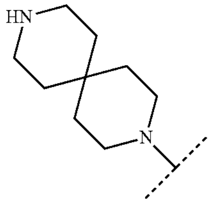 | -4-PhCOOH | 699.4 | 5.61 |
| 147 | Racemic | 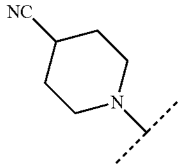 | -4-PhCOOH | 655.3 | 9.54 |
| 148 | Racemic | 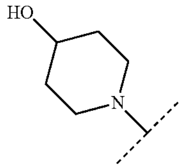 | -4-PhCOOH | 646.3 | 6.94 |
| 149 | S-enantiomer[j] | 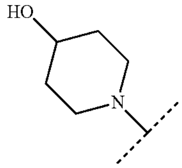 | -4-PhCOOH | 646.2 | 7.38 |

TABLE 9-continued

| Example # | stereochemistry | R | R' | M + H | RT |
|---|---|---|---|---|---|
| 150 | Racemic | 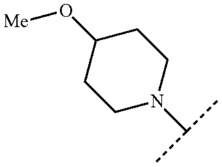 | -4-PhCOOH | 660.3 | 9.37 |
| 151 | S-enantiomer | 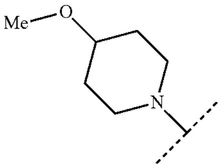 | -4-PhCOOH | 660.3 | 8.45 |
| 152 | Racemic | 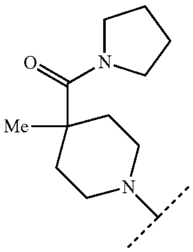 | -4-PhCOOH | 741.4 | 7.89 |

[a]Chiralpak AD-H, 250 × 21 mm ID, 5 μm, using 55/45 $CO_2$/(1:1) EtOH-IPA-0.1% DEA at 60 mL/min, 150 bar BP, 40° C.
[b]Chiralpak AD-H, 250 × 21 mm ID, 5 μm, using 50/50 $CO_2$/(1:1) EtOH-IPA-0.1% DEA at 90 mL/min, 150 bar BP, 40° C.
[c]Chiralpak AD-H, 250 × 21 mm ID, 5 μm, using 40/60 $CO_2$/(1:1) EtOH-IPA-0.1% DEA at 60 mL/min, 125 bar BP, 40° C.
[d]Chiralpak AD-H, 150 × 20 mm ID, 5 μm, using 50/50 $CO_2$/IPA-0.1% DEA at 55 mL/min, 150 bar BP, 35° C.
[e]Chiralpak AS-H, 150 × 20 mm ID, 5 μm, using 60/40 $CO_2$/MeOH-0.1% DEA at 60 mL/min, 100 bar BP, 35° C.
[f]Chiralpak AD-H, 250 × 30 mm ID, 5 μm, using 50/50 $CO_2$/(1:1) EtOH-0.1% DEA at 100 mL/min, 150 bar BP, 40° C.
[g]Chiralpak AD-H, 150 × 21 mm ID, 5 μm, using 55/45 $CO_2$/(1:1) EtOH-IPA-0.1% DEA at 45 mL/min, 150 bar BP, 40° C.
[h]Chiralpak AD-H, 150 × 21 mm ID, 5 μm, using 50/50 $CO_2$/(1:1) EtOH-IPA-0.1% DEA at 50 mL/min, 150 bar BP, 50° C.
[i]Chiralpak OD-H, 250 × 30 cm ID, 5 μm, using 65/35 $CO_2$/EtOH-0.1%DIPA at 90 mL/min, 150 bar BP, 45° C.
[j]Chiralpak AD-H, 25 × 2 cm ID, 5 μm, using 60/40 $CO_2$/IPA-20 mM $NH_4OH$ at 50 mL/min, 100 bar BP.
[k]Chiralcel OJ-H, 25 × 2 cm ID, 5 μm, using 70/30 $CO_2$/IPA-0.1% DEA at 70 mL/min, 100 bar BP.
**LCMS retention time.

The following examples in Table 10 were prepared in a similar manner as Example 80 substituting Intermediate 3A for the appropriate carboxylic acid listed and were separated by chiral HPLC on late stage intermediates followed by deprotection and purification where indicated.

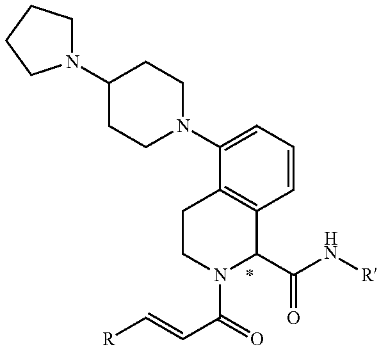

TABLE 10
| Example | Stereochemistry | R | R' | M + H | RT |
|---|---|---|---|---|---|
| 153 | Racemic | 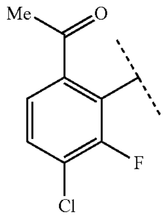 | -4-PhCOOtBu | 729.4 | 7.76 |
| 154 | Racemic | 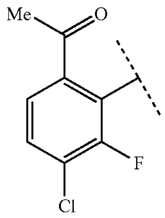 | -4-PhCOOH | 673.5 | 6.07 |
| 155 | Racemic | 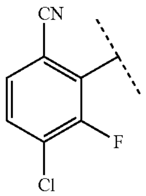 | -4-PhCOOH | 656.5 | 6.18 |
| 156 | Racemic | 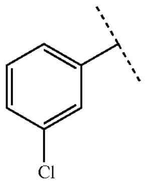 | -4-PhCOOH | 613.4 | 6.31 |
| 157 | Racemic | 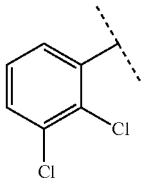 | -4-PhCOOH | 647.5 | 7.45 |
| 158 | Racemic | 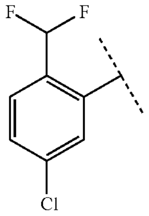 | -4-PhCOOH | 663.5 | 6.39 |

TABLE 10-continued
| Example | Stereochemistry | R | R' | M + H | RT |
|---|---|---|---|---|---|
| 159 | Racemic | 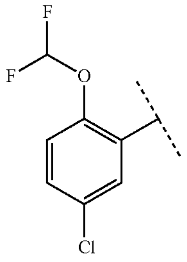 | -4-PhCOOH | 679.6 | 6.47 |
| 160 | Racemic | 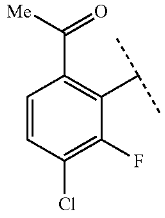 | -4-PhCOOEt | 701.6 | 7.07 |
| 161 | Racemic | 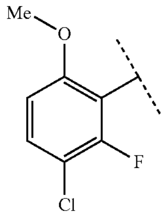 | -4-PhCOOH | 661.2 | 6.99 |
| 162 | Racemic | 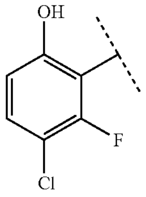 | -4-PhCOOH | 647.2 | 7.16 |
| 163 | R-enantiomer[a] | 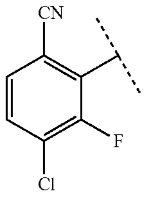 | -4-PhCOOH | 656.4 | 5.99 |
| 164 | S-enantiomer[a] | 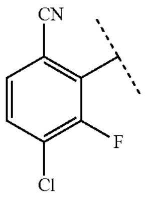 | -4-PhCOOH | 656.4 | 5.97 |

TABLE 10-continued
| Example | Stereochemistry | R | R' | M + H | RT |
|---|---|---|---|---|---|
| 165 | Racemic | 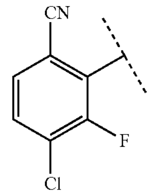 | -4-PhCOOEt | 684.5 | 9.90 |
| 166 | S-enantiomer[c] | 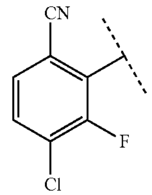 | -4-PhCOOEt | 684.3 | 7.39 |
| 167 | R-enantiomer[a] | 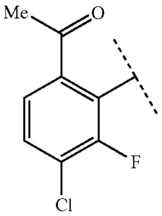 | -4-PhCOOH | 673.4 | 5.83 |
| 168 | S-enantiomer[a] | 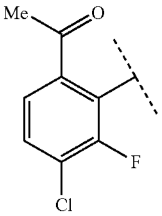 | -4-PhCOOH | 673.4 | 5.82 |
| 169 | R-enantiomer[a] | 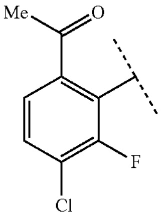 | -4-PhCOOEt | 701.4 | 7.05 |
| 170 | S-enantiomer[a] | 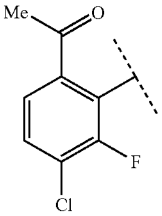 | -4-PhCOOEt | 701.4 | 7.06 |
| 171 | S-enantiomer | 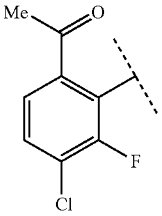 | -4-PhCOOBzl | 763.2 | 6.72* |

TABLE 10-continued
| Example | Stereochemistry | R | R' | M + H | RT |
|---|---|---|---|---|---|
| 172 | S-enantiomer | 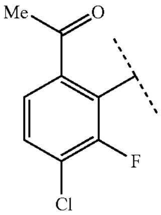 | -4-PhCOOCH2CON($CH_3$)$_2$ | 758.2 | 6.74 |
| 173 | S-enantiomer | 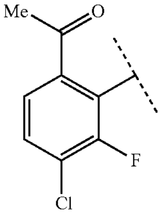 | 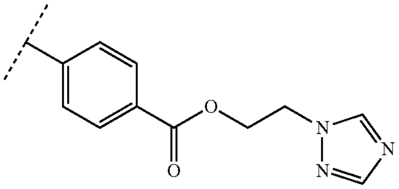 | 768.2 | 6.53 |
| 174 | S-enantiomer | 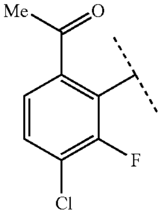 | 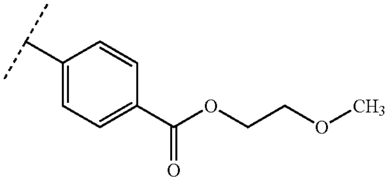 | 731.2 | 7.59 |
| 175 | Racemic | 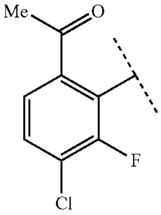 | -4-PhCOOCH$_3$ | 687.1 | 7.53 |
| 176 | Racemic | 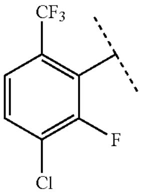 | -4-PhCOOH | 699.5 | 8.26 |
| 177 | S-enantiomer[b] | 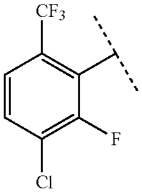 | -4-PhCOOEt | 727.5 | 9.14 |
| 178 | S-enantiomer[b] | 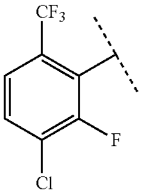 | -4-PhCOOH | 699.5 | 6.81 |

TABLE 10-continued

| Example | Stereochemistry | R | R' | M + H | RT |
|---|---|---|---|---|---|
| 179 | R-enantiomer[b] | 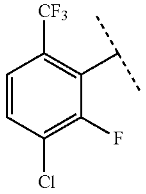 | -4-PhCOOH | 699.5 | 6.84 |
| 180 | Racemic | 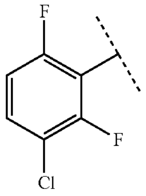 | -4-PhCOOH | 649.5 | 7.86 |
| 181 | Racemic | 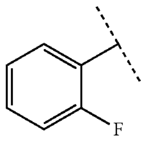 | -4-PhCOOH | 597.5 | 6.08 |
| 182 | Racemic | 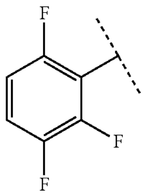 | -4-PhCOOH | 633.5 | 6.87 |

[a]Chiralpak AD-H, 250 x 21 cm ID, 5 μm, using 50/50 $CO_2$/EtOH-IPA-0.1% DEA at 60 mL/min, 125 bar BP, 40° C.
[b]Chiralpak AD-H, 250 x 21 cm ID, 5 μm, using 60/40 $CO_2$/EtOH-IPA-0.1% DEA at 45.5 mL/min, 150 bar BP, 50° C.
[c]Chiralcel OD-H, 250 x 30 mm ID, 5 μm, using 55/45 $CO_2$/EtOH-IPA-0.1% DEA at 85 mL/min, 100 bar BP, 40° C.

*Method B

Example 183

(R,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido) benzoic acid, TFA salt

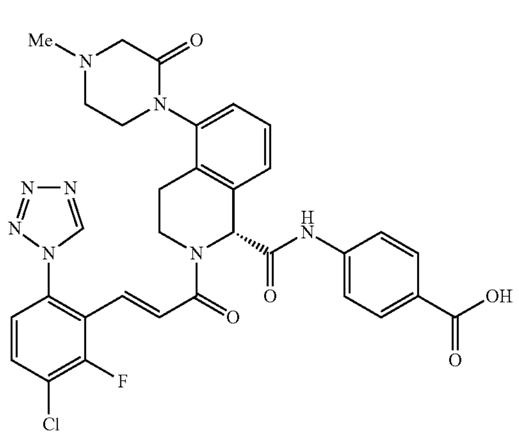 [SMILES: CN1CCN(c2cccc3c2CCN(C(=O)/C=C/c2c(-n4cnnn4)ccc(Cl)c2F)[C@H]3C(=O)Nc2ccc(C(=O)O)cc2)C(=O)C1]

Example 57 (Table 7): (E)-tert-butyl 4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoate: Intermediate 3A (0.320 g, 1.192 mmol) and Intermediate 22 (0.29 g, 1.192 mmol) were combined in a vial in EtOH (5 mL) and after 10 min., Intermediate 6 (0.315 g, 1.550 mmol) in EtOH (3 mL) was added and reaction was heated at 55° C. for 24 h. The reaction was concentrated and the residue was purified by silica gel column chromatography followed by reverse phase HPLC and freeze-dried to afford 0.339 g (32.6%) of Example 57 (Table 7) as a white solid. $^1$H NMR (400 MHz, MeOD) δ: 9.44 (1H, s), 7.74-7.84 (2H, m), 7.62-7.73 (1H, m), 7.43-7.58 (3H, m), 7.37 (1H, dd, J=8.72, 1.64 Hz), 7.31 (1H, td, J=7.83, 2.78 Hz), 7.19 (1H, t, J=6.82 Hz), 6.98-7.11 (1H, m), 6.79-6.94 (1H, m), 5.80 (1H, s), 3.94-4.20 (3H, m), 3.84-3.95 (1H, m), 3.62-3.80 (3H, m), 3.53-3.64 (1H, m), 2.99 (3H, s), 2.92-2.96 (1H, m), 2.61-2.77 (1H, m), 1.47 (9H, d, J=2.02 Hz) ppm. MS (ESI) m/z: 715.3. Analytical HPLC: RT=6.82 min.

Example 183 was prepared from Example 57 (Table 7) and isolated as the first eluting peak after chiral HPLC separation using Chiralpak AD-H, 250×30 mm, 5 μm, using 60/40 $CO_2$/1:1 EtOH-IPA-0.1% DEA at 90 mL/min, 150 bar BP, 35° C. followed by deprotection with TFA/DCM and HPLC purification to afford 96.8 mgs (25.8%) of a white solid. $^1$H NMR (400 MHz, MeOD) δ: 9.44 (1H, s), 7.78-7.95 (2H, m), 7.69 (1H, td, J=8.08, 2.53 Hz), 7.44-7.60 (3H, m), 7.27-7.41 (2H, m), 7.15-7.25 (1H, m), 6.98-7.11 (1H, m), 6.77-6.98 (1H, m), 5.78-5.88 (1H, m), 3.83-4.19 (4H, m), 3.64-3.80 (3H, m), 3.54-3.64 (1H, m), 3.03 (3H, s), 2.93-3.00 (1H, m), 2.63-2.78 (1H, m) ppm MS (ESI) m/z: 659.3 $(M+H)^+$. Analytical HPLC: RT=4.90 min.

Example 184

(S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid, TFA salt

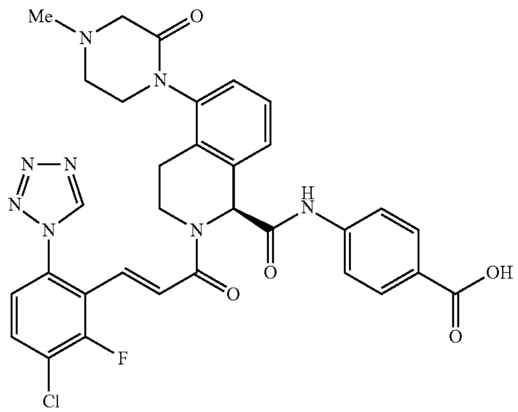 [SMILES: CN1CCN(c2cccc3c2CCN(C(=O)/C=C/c2c(-n4cnnn4)ccc(Cl)c2F)[C@@H]3C(=O)Nc2ccc(C(=O)O)cc2)C(=O)C1]

Example 184 was isolated as the second eluting enantiomer from Example 57 (Table 7) and deprotected and purified as described in Example 183 to afford 104 mgs (27.7%) of a white solid. $^1$H NMR (400 MHz, MeOD) δ: 9.45 (1H, s), 7.79-7.92 (2H, m), 7.64-7.74 (1H, m), 7.44-7.62 (3H, m), 7.27-7.43 (2H, m), 7.15-7.24 (1H, m), 6.97-7.12 (1H, m), 6.72-6.90 (1H, m), 5.77-5.88 (1H, m), 3.82-4.17 (4H, m), 3.53-3.82 (4H, m), 2.99-3.03 (1H, m), 2.98 (3H, s), 2.60-2.77 (1H, m) ppm. MS (ESI) m/z: 659.3 $(M+H)^+$. Analytical HPLC: RT=4.94 min.

The following compounds listed in Table 11 were isolated following chiral HPLC separation of the appropriate racemic example listed.

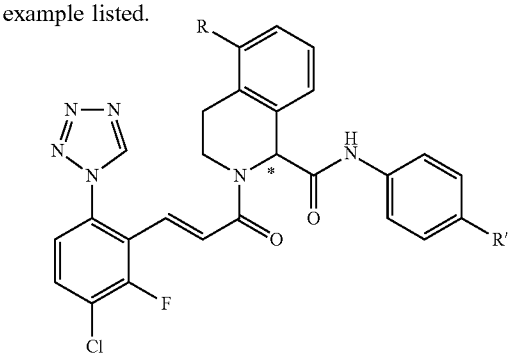

TABLE 11

| Example # | Racemic Example # | Stereo-chemistry | R | R' | M + H | RT |
|---|---|---|---|---|---|---|
| 185 | 63 | S-enantiomer[a] | 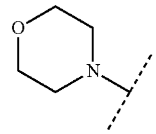 | —COOEt | 660.4 | 10.13 |
| 186 | 63 | R-enantiomer[a] | 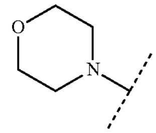 | —COOEt | 660.4 | 10.14 |
| 187 | 54 | R-enantiomer[b] | 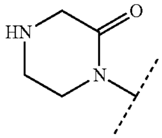 | —COOH | 645.3 | 4.85 |
| 188 | 54 | S-enantiomer[b] | 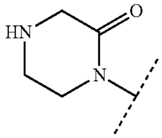 | —COOH | 645.3 | 4.87 |
| 189 | 56 | R-enantiomer[c] | 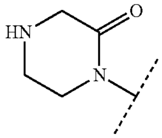 | —COOEt | 672.3 | 5.80 |
| 190 | 56 | S-enantiomer[c] | 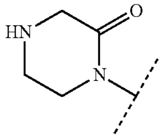 | —COOEt | 672.3 | 5.77 |

[a]Chiralpak IA, 250 x 30 mm, 5 μm, using 60/40 $CO_2$/1:1EtOH-IPA-0.1% DEA at 90 mL/min, 150 bar BP, 35° C.
[b]Chiralpak IA, 250 x 21 mm, 5 μm, using 55/45 to 60/40 $CO_2$/1:1EtOH-ACN at 40 mL/min, 150 bar BP, 35° C.
[c]Chiralpak AD-H, 250 x 21 mm, 5 μm, using 55/45 to 60/40 $CO_2$/1:1EtOH-ACN at 40 mL/min, 150 bar BP, 35° C.

Example 191

(R,E)-Ethyl 4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoate, TFA Salt

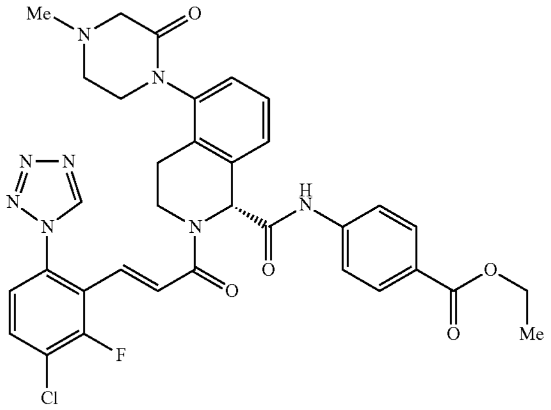 [SMILES: CCOC(=O)c1ccc(NC(=O)[C@H]2c3cccc(N4CCN(C)CC4=O)c3CCN2C(=O)/C=C/c2c(-n3cnnn3)ccc(Cl)c2F)cc1]

Example 191 was prepared as in Example 189 (Table 11) using Intermediate 22, Intermediate 9 and Intermediate 3A to afford 84.4 mg (43%) as the first peak after chiral HPLC separation using Chiralpak IA, 250×30 mm, 5 μm, using 60/40 $CO_2$/1:1 EtOH-IPA-0.1% DEA at 100 mL/min, 150 bar BP, 40° C. $^1$H NMR (400 MHz, MeOD) δ 9.50 (1H, s), 7.85-7.96 (2H, m), 7.72-7.77 (1H, m), 7.61 (2H, dd, J=8.79, 6.05 Hz), 7.48-7.56 (1H, m), 7.44 (1H, d, J=8.79 Hz), 7.35 (1H, td, J=7.83, 3.02 Hz), 7.16-7.27 (1H, m), 7.05-7.14 (1H, m), 6.94-7.05 (1H, m), 5.84 (1H, d, J=7.70 Hz), 4.22-4.33 (2H, m), 4.09 (1H, s), 3.51-3.82 (2H, m), 3.43 (2H, br. s.), 2.94-3.07 (4H, m), 2.70-2.81 (1H, m), 2.55 (3H, br. s.), 1.25 (3H, t, J=7.42 Hz) ppm. MS (ESI) m/z: 687.3 $(M+H)^+$. Analytical HPLC: RT=5.91 min.

Example 192

(S,E)-Ethyl 4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoate, TFA Salt

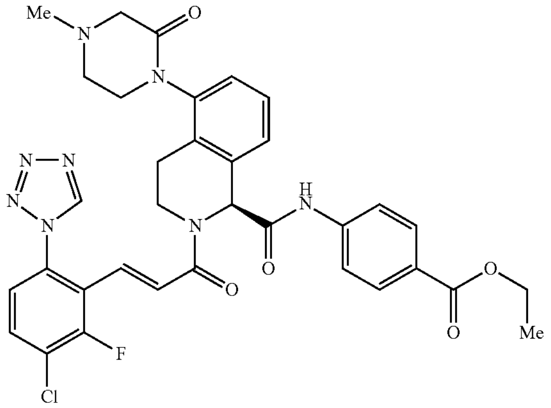 [SMILES: CCOC(=O)c1ccc(NC(=O)[C@@H]2c3cccc(N4CCN(C)CC4=O)c3CCN2C(=O)/C=C/c2c(-n3cnnn3)ccc(Cl)c2F)cc1]

Example 192 was prepared as in Example 190 (Table 11) using Intermediate 22, Intermediate 9 and Intermediate 3A to afford 84.4 mg (43%) as the second peak after chiral HPLC separation using Chiralpak IA, 250×30 mm, 5 μm, using 60/40 $CO_2$/1:1 EtOH-IPA-0.1% DEA at 100 mL/min, 150 bar BP, 40° C. $^1$H NMR (400 MHz, MeOD) δ: 9.54 (1H, s), 7.90-7.99 (2H, m), 7.74-7.82 (1H, m), 7.61-7.70 (2H, m), 7.56 (1H, dd, J=19.24, 7.70 Hz), 7.47 (1H, d, J=8.79 Hz), 7.38 (1H, td, J=7.70, 3.85 Hz), 7.24 (1H, t, J=6.87 Hz), 6.98-7.16 (2H, m), 5.88 (1H, d, J=8.24 Hz), 4.26-4.38 (2H, m), 4.06-4.16 (1H, m), 3.60-3.81 (3H, m), 3.47-3.58 (1H, m), 3.02-3.16 (2H, m), 2.83-2.95 (2H, m), 2.75-2.85 (1H, m), 2.45 (3H, s), 1.36 (3H, t, J=7.15 Hz) ppm. MS (ESI) m/z: 687.3 $(M+H)^+$. Analytical HPLC: RT=5.90 min.

Example 193

(R,E)-4-(2-(3-(3-Chloro-2-fluoro-6-(1H-tetrazol-1-yl)phenyl)acryloyl)-3,3-dimethyl-5-(piperazin-1-yl)-1,2,3,4-tetrahydroisoquinoline-1-carboxamido) benzoic acid, bis-TFA salt

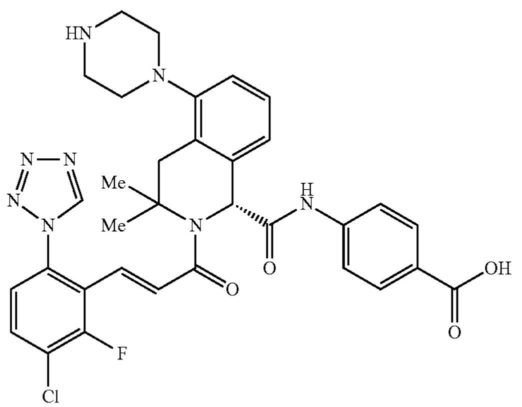 [SMILES: CC1(C)Cc2c(cccc2N2CCNCC2)[C@H](C(=O)Nc2ccc(C(=O)O)cc2)N1C(=O)/C=C/c1c(-n2cnnn2)ccc(Cl)c1F]

Example 193 was prepared from Example 78 tert-butyl ester intermediate by chiral HPLC separation using Chiralpak IA (250×4.6) mm eluting with hexane:EtOH (50:50) and 0.2% DEA at 1 mL/min. $^1$H NMR (400 MHz, DMSO-$d_6$) δ 12.77 (1H, s), 10.48 (1H, s), 9.86 (1H, s), 8.67 (2H, q), 7.95 (2H, t, J=8.4 Hz), 7.88 (1H, bs), 7.64 (3H, d, J=9.2 Hz), 7.53 (1H, d, J=7.6 Hz), 7.29 (1H, t, J=8.0 Hz), 7.07-7.11 (3.0H, m), 5.74 (1H, bs), 3.23 (2H, q), 3.08 (2H, t, J=12.4 Hz), 2.91-2.95 (3H, m), 1.81 (3H, s), 1.11 (3H, s) ppm. MS (ESI) m/z: 659.2 $(M+H)^+$. Analytical HPLC: RT=11.26 min.

Example 194

(S,E)-4-(2-(3-(3-Chloro-2-fluoro-6-(1H-tetrazol-1-yl)phenyl)acryloyl)-3,3-dimethyl-5-(piperazin-1-yl)-1,2,3,4-tetrahydroisoquinoline-1-carboxamido) benzoic acid, bis-TFA salt

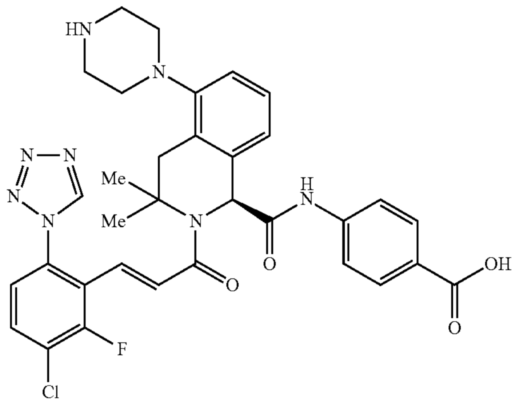 [SMILES: CC1(C)Cc2c(cccc2N2CCNCC2)[C@@H](C(=O)Nc2ccc(C(=O)O)cc2)N1C(=O)/C=C/c1c(-n2cnnn2)ccc(Cl)c1F]

Example 194 was prepared from Example 78 tert-butyl ester intermediate by chiral HPLC separation using Chiralpak IA (250×4.6) mm eluting with hexane:EtOH (50:50) and 0.2% DEA at 1 mL/min. $^1$H NMR (400 MHz, DMSO-$d_6$) δ 12.77 (1H, s), 10.51 (1H, s), 9.86 (1H, s), 8.68 (2H, bs), 7.95 (2H, t, J=8.4 Hz), 7.88 (1H, bs), 7.65 (3H, d, J=8.8 Hz), 7.52 (1H, d, J=7.6 Hz), 7.29 (1H, t, J=8.0 Hz), 7.09 (3H, t, J=9.2 Hz), 6.82 (1H, bs), 5.79 (1H, bs), 3.15-3.35 (2H, m), 3.10-2.80 (5H, m), 1.80 (3H, s), 1.10 (3H, s). MS (ESI) m/z: 659.2 (M+H)$^+$. Analytical HPLC: RT=11.28 min.

The following compounds listed in Table 12 were isolated following chiral HPLC separation of the appropriate racemic example listed.

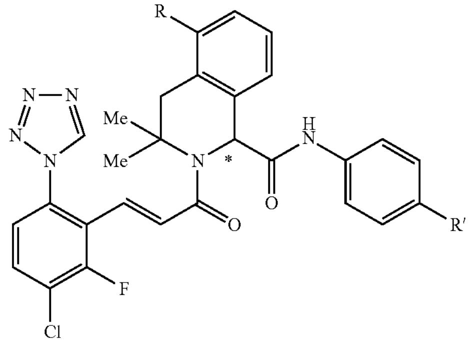

TABLE 12

| Example # | Stereochemistry | R | R' | M + H | RT |
|---|---|---|---|---|---|
| 195 | S-enantiomer[a] | 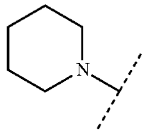 | —COOH | 658.2 | 2.093 |
| 196 | R-enantiomer[a] | 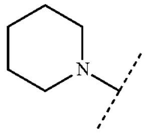 | —COOH | 658.2 | 2.094 |
| 197 | S-enantiomer[b] | 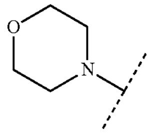 | —COOEt | 688.2 | 2.141 |
| 198 | R-enantiomer[b] | 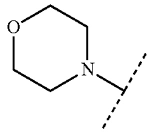 | —COOEt | 688.2 | 2.142 |
| 199 | S-enantiomer[c] | 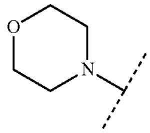 | —COOH | 660.2 | 1.974 |
| 200 | R-enantiomer[c] | 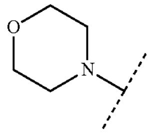 | —COOH | 660.2 | 1.973 |
| 201 | S-enantiomer[d] | 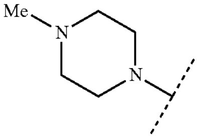 | —COOH | 673.2 | 1.515 |
| 202 | R-enantiomer[d] | 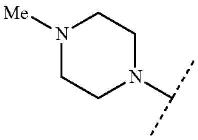 | —COOH | 673.2 | 1.509 |

TABLE 12-continued

| Example # | Stereochemistry | R | R' | M + H | RT |
|---|---|---|---|---|---|
| 203 | S-enantiomer[d] | 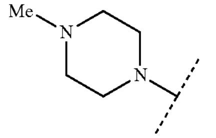 | —COOEt | 701.2 | 1.746 |
| 204 | S-enantiomer[d] | 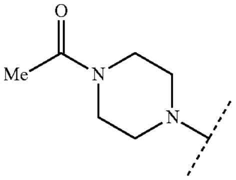 | —COOH | 701.2 | 1.859 |
| 205 | R-enantiomer[d] | 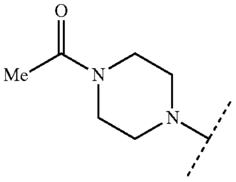 | —COOH | 701.2 | 1.858 |

1. [a]Chiralpak AD-H, 250 × 30 mm, 5 μm, using 40/60 $CO_2$/1:1EtOH-IPA-0.1% DEA at 90.0 mL/min, 150 bar BP, 35° C.
2. [b]Chiralpak IA, 250 × 30 mm, 5 μm, using 60/40 $CO_2$/1:1EtOH-IPA-0.1% DEA at 90.0 mL/min, 150 bar BP, 35° C.
3. [c]Chiralpak IA, 250 × 21 mm, 5 μm, using 55/45 to 60/40 $CO_2$/1:1EtOH-ACN at 40.0 mL/min, 150 bar BP, 35° C.
4. [d]Chiralpak AD-H, 250 × 21 mm, 5 μm, using 55/45 to 60/40 $CO_2$/1:1EtOH-ACN at 40.0 mL/min, 150 bar BP, 35° C.

Example 206

4-((S)-2-((E)-3-(3-Chloro-2-fluoro-6-(1H-tetrazol-1-yl)phenyl)acryloyl)-5-((S)-3-(dimethylamino)pyrrolidin-1-yl)-1,2,3,4-tetrahydroisoquinoline-1-carboxamido)benzoic acid, bis-TFA salt

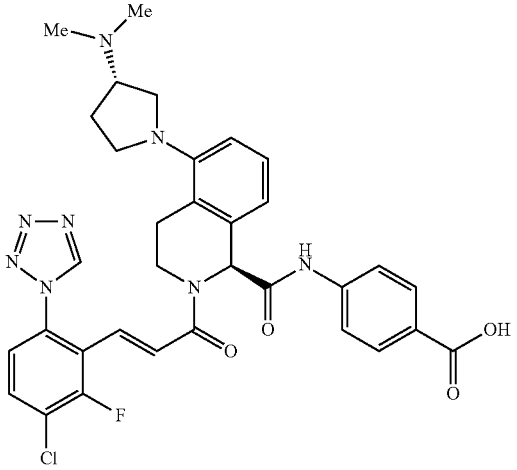 [SMILES: CN(C)[C@H]1CCN(c2cccc3c2CCN(C(=O)/C=C/c2c(-n4cnnn4)ccc(Cl)c2F)[C@@H]3C(=O)Nc2ccc(C(=O)O)cc2)C1]

206A: (S)-1-(3,4-Dihydroisoquinolin-5-yl)-N,N-dimethylpyrrolidin-3-amine: To 5-bromoisoquinoline (0.60 g, 2.88 mmol), (S)—N,N-dimethylpyrrolidin-3-amine (0.428 g, 3.75 mmol), $Pd_2(dba)_3$ (0.053 g, 0.058 mmol), BINAP (0.072 g, 0.115 mmol), and sodium tert-butoxide (0.39 g, 4.04 mmol) was added degassed toluene (10 mL) and the mixture was heated to 85° C. overnight. The reaction mixture was dissolved in EtOAc, washed with brine, dried over $Na_2SO_4$, filtered, and concentrated. This intermediate was reduced and then, oxidized as described in Example 1 to afford 206A (577 mg, 82%).

Example 206: 206A (0.25 g, 1.03 mmol), Intermediate 3A (0.28 g, 1.03 mmol), and Intermediate 6 (0.23 g, 1.13 mmol) were combined in an Ugi reaction as described in Example 1 and then, deprotected by TFA. Purification by reverse phase HPLC afforded Example 206 as the first of two diastereomers. The compound was obtained as a light yellow solid after lyophilization. $^1H$ NMR (500 MHz, DMSO-$d_6$) δ 10.78 (1H, s), 9.88 (1H, s), 7.97 (1H, t, J=8.12 Hz), 7.87 (2H, d, J=8.80 Hz), 7.68 (3H, d, J=8.80 Hz), 7.30 (1H, d, J=7.70 Hz), 7.22 (1H, t, J=7.84 Hz), 7.03-7.09 (1H, m), 6.93-7.02 (2H, m), 5.75 (1H, s), 3.94-4.10 (1H, m), 3.20-3.55 (9H, m), 2.79-3.06 (5H, m), 2.27-2.40 (1H, m), 2.06-2.21 (1H, m) ppm. MS (ESI) m/z: 659.3 $(M+H)^+$. Analytical HPLC: RT=4.53 min.

Example 207 tert-butyl 4-((S)-2-((E)-3-(3-chloro-2-fluoro-6-(1H-tetrazol-1-yl)phenyl)acryloyl)-5-((S)-3-(dimethylamino)pyrrolidin-1-yl)-1,2,3,4-tetrahydroisoquinoline-1-carboxamido) benzoate, bis TFA salt:

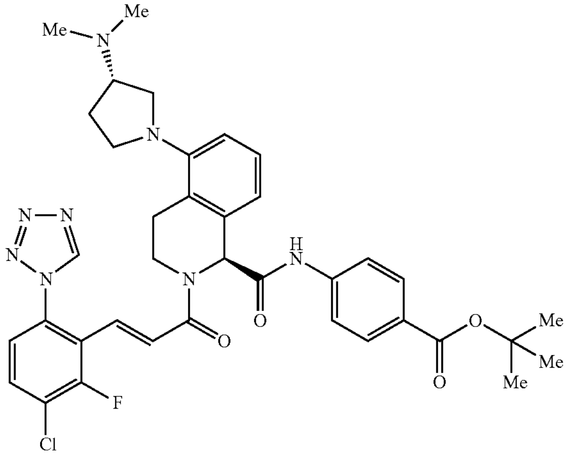 [SMILES: CN(C)[C@H]1CCN(c2cccc3c2CCN(C(=O)/C=C/c2c(-n4cnnn4)ccc(Cl)c2F)[C@@H]3C(=O)Nc2ccc(C(=O)OC(C)(C)C)cc2)C1]

Example 207: 206A (0.25 g, 1.03 mmol), Intermediate 3A (0.28 g, 1.03 mmol), and Intermediate 6 (0.23 g, 1.13 mmol) were combined in an Ugi reaction as described in Example 1. Purification by reverse phase HPLC afforded Example 207. $^1$H NMR (500 MHz, DMSO-$d_6$) δ 10.77 (1H, s), 9.86 (1H, s), 7.96 (1H, t, J=8.25 Hz), 7.82 (2H, d, J=8.80 Hz), 7.67 (3H, d, J=9.08 Hz), 7.29 (1H, d, J=7.43 Hz), 7.17-7.25 (1H, m), 6.87-7.08 (3H, m), 5.75 (1H, s), 3.92-4.07 (2H, m), 3.23-3.54 (4H, m), 2.80-3.05 (9H, m), 2.26-2.37 (1H, m), 2.09-2.19 (1H, m), 1.50-1.55 (9H, m) ppm. MS (ESI) m/z: 715.5 (M+H)$^+$. Analytical HPLC: RT=8.68 min Example 208

4-((R)-2-((E)-3-(3-Chloro-2-fluoro-6-(1H-tetrazol-1-yl)phenyl)acryloyl)-5-((S)-3-(dimethylamino)pyrrolidin-1-yl)-1,2,3,4-tetrahydroisoquinoline-1-carboxamido)benzoic acid, bis-TFA salt

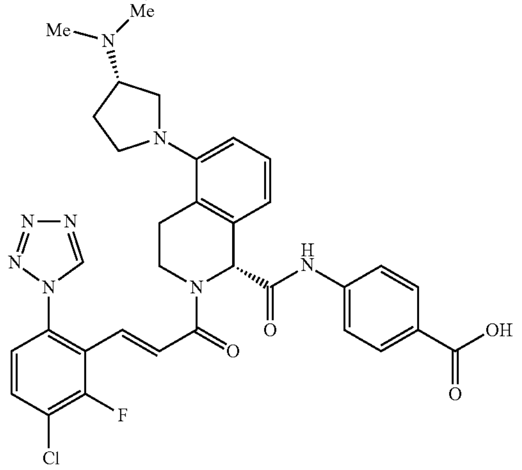 [SMILES: CN(C)[C@H]1CCN(c2cccc3c2CCN(C(=O)/C=C/c2c(-n4cnnn4)ccc(Cl)c2F)[C@H]3C(=O)Nc2ccc(C(=O)O)cc2)C1]

Example 208 was obtained as the second eluting diastereomer during the synthesis and purification of Example 206. The compound was obtained as a light yellow solid after lyophilization. $^1$H NMR (500 MHz, DMSO-$d_6$) δ 12.73 (1H, br. s.), 10.75 (1H, s), 9.88 (1H, s), 7.97 (1H, t, J=8.12 Hz), 7.81-7.93 (2H, m), 7.63-7.72 (2H, m), 7.31 (1H, d, J=7.70 Hz), 7.21 (1H, t, J=7.84 Hz), 7.03-7.12 (1H, m), 6.91-7.00 (2H, m), 5.72 (1H, s), 4.03-4.19 (1H, m), 3.86-3.98 (1H, m), 3.37-3.49 (3H, m), 3.07-3.30 (5H, m), 2.81-2.92 (7H, m) ppm. MS (ESI) m/z: 659.3 (M+H)$^+$. Analytical HPLC: RT=4.64 min.

Example 209

4-((R)-2-((E)-3-(3-Chloro-2-fluoro-6-(1H-tetrazol-1-yl)phenyl)acryloyl)-5-((R)-3-(dimethylamino)pyrrolidin-1-yl)-1,2,3,4-tetrahydroisoquinoline-1-carboxamido)benzoic acid, bis TFA salt

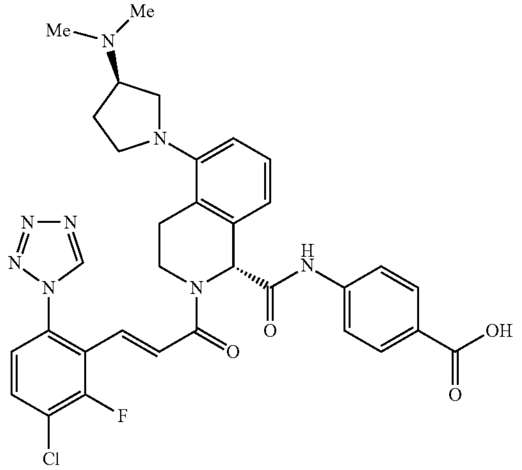 [SMILES: CN(C)[C@@H]1CCN(c2cccc3c2CCN(C(=O)/C=C/c2c(-n4cnnn4)ccc(Cl)c2F)[C@H]3C(=O)Nc2ccc(C(=O)O)cc2)C1]

Example 209 was prepared in a similar manner as Example 206 substituting (R)—N,N-dimethylpyrrolidin-3-amine instead of (S)—N,N-dimethylpyrrolidin-3-amine in Buchwald reaction. The compound was the first eluting diastereomer during purification by reverse phase prep HPLC. $^1$H NMR (500 MHz, DMSO-$d_6$) δ 12.74 (1H, br. s.), 10.78 (1H, s), 9.88 (1H, s), 7.97 (1H, t, J=8.12 Hz), 7.87 (1H, d, J=8.80 Hz), 7.67 (1H, d, J=8.80 Hz), 7.30 (1H, d, J=7.43 Hz), 7.21 (1H, t, J=7.84 Hz), 7.03-7.09 (1H, m), 6.94-7.01 (2H, m), 5.75 (1H, s), 3.90-4.18 (2H, m), 3.40-3.56 (3H, m), 3.19-3.33 (5H, m), 2.80-2.98 (7H, m) ppm. MS (ESI) m/z: 659.3 (M+H)$^+$. Analytical HPLC: RT=4.57 min.

Example 210

4-((S)-2-((E)-3-(3-Chloro-2-fluoro-6-(1H-tetrazol-1-yl)phenyl)acryloyl)-5-((R)-3-(dimethylamino)pyrrolidin-1-yl)-1,2,3,4-tetrahydroisoquinoline-1-carboxamido)benzoic acid, bis-TFA salt

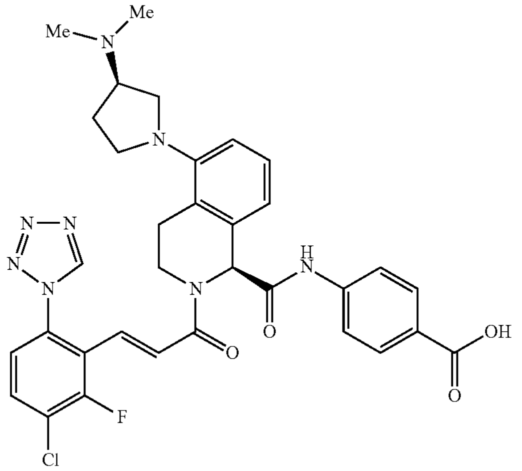 [SMILES: CN(C)[C@@H]1CCN(c2cccc3c2CCN(C(=O)/C=C/c2c(-n4cnnn4)ccc(Cl)c2F)[C@@H]3C(=O)Nc2ccc(C(=O)O)cc2)C1]

Example 210 was prepared in a similar manner as Example 206 substituting (R)—N,N-dimethylpyrrolidin-3-amine instead of (S)—N,N-dimethylpyrrolidin-3-amine in Buchwald reaction. The compound was the second eluting diastereomer during purification by reverse phase prep HPLC. $^1$H NMR (500 MHz, DMSO-$d_6$) δ 10.74 (1H, s), 9.87 (1H, s), 7.96 (1H, t, J=8.12 Hz), 7.83-7.88 (2H, m), 7.63-7.70 (3H, m), 7.27-7.34 (1H, m), 7.17-7.23 (1H, m), 7.02-7.10 (1H, m), 6.90-7.01 (2H, m), 5.71 (1H, s), 4.07-4.20 (1H, m), 3.84-3.98 (1H, m), 3.35-3.44 (3H, m), 3.09-3.29 (5H, m), 2.79-2.92 (7H, m) ppm. MS (ESI) m/z: 659.3 (M+H)$^+$. Analytical HPLC: RT=4.64 min.

The following examples in Table 13 were made by Ugi reaction as described in Example 1 using appropriate imine intermediates and carboxylic acids (Intermediates 3A, 12, or 16). Deprotection with TFA/DCM was carried out where necessary. Single enantiomers were isolated by chiral HPLC at a protected late stage intermediate and then, deprotected where indicated.

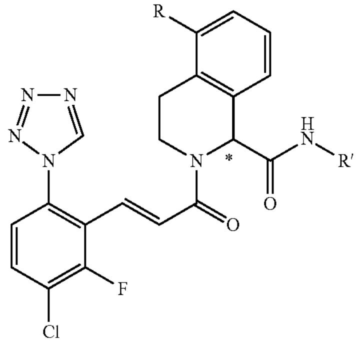

TABLE 13

| Example # | Stereo-chemistry | R | R' | M + H | RT |
|---|---|---|---|---|---|
| 211 | Racemic | 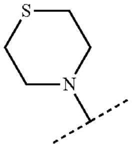 | -4-PhCOOH | 648.3 | 9.53 |
| 212 | S-enantiomer[a] | 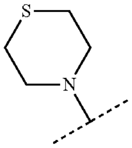 | -4-PhCOOH | 648.2 | 10.61 |
| 213 | Racemic | 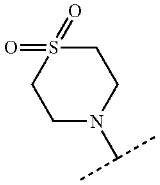 | -4-PhCOOH | 680.4 | 11.28 |

TABLE 13-continued

| Example # | Stereo-chemistry | R | R' | M + H | RT |
|---|---|---|---|---|---|
| 214 | S-enantiomer[b] | 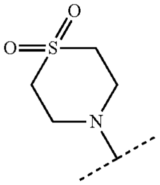 | -4-PhCOOH | 680.4 | 7.80 |

[a]Chiralpak AD-H, 250 × 21 mm ID, 45% (1:1EtOH-IPA-0.1%DEA)/55% $CO_2$ at 45 mL/min, 120 bar, 45° C.

[b]Chiralpak AD-H, 250 × 21 mm ID, 45% (1:1EtOH-IPA-0.1%DEA)/55% $CO_2$ at 60 mL/min, 100 bar, 35° C.

The following examples in Table 14 were made by Ugi reaction as described in Example 18 using appropriate imine intermediates. Deprotection with TFA/DCM was carried out where necessary. Single enantiomers were isolated by chiral HPLC at a protected late stage intermediate and then, deprotected where indicated.

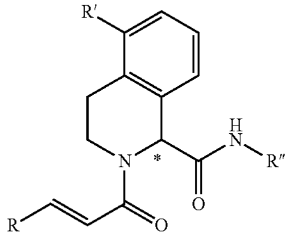

TABLE 14

| Example # | Stereochemistry | R | R' | R" | M + H | RT |
|---|---|---|---|---|---|---|
| 215 | Racemic | 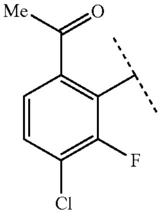 | 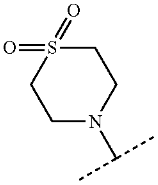 | -4-PhCOOH | 655.4 | 8.19 |
| 216 | R-enantiomer[a] | 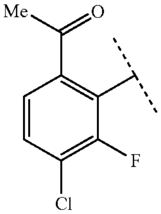 | 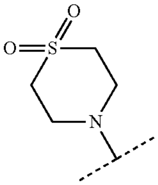 | -4-PhCOOH | 654.3 | 9.43 |

TABLE 14-continued
| Example # | Stereochemistry | R | R' | R" | M + H | RT |
|---|---|---|---|---|---|---|
| 217 | S-enantiomer[a] | 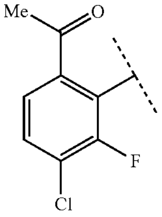 | 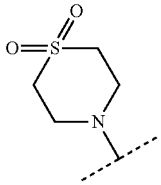 | -4-PhCOOH | 654.3 | 8.19 |
| 218 | Racemic | 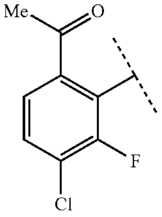 | 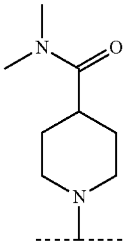 | -4-PhCOOH | 675.3 | 7.97 |
| 219 | S-enantiomer[b] | 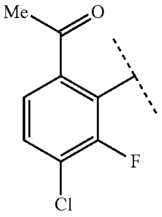 | 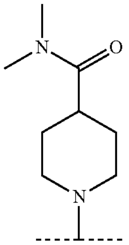 | -4-PhCOOH | 675.3 | 8.31 |
| 220 | Racemic | 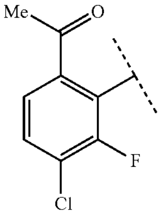 | 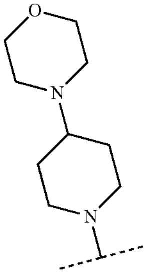 | -4-PhCOOH | 689.3 | 7.15 |
| 221 | R-enantiomer[c] | 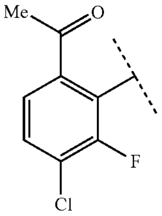 | 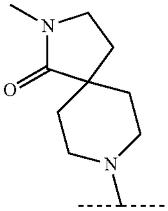 | -4-PhCOOH | 687.5 | 8.50 |
| 222 | S-enantiomer[c] | 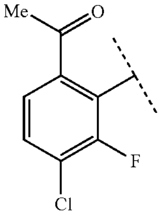 | 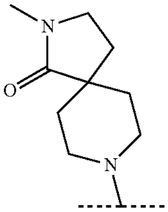 | -4-PhCOOH | 687.3 | 10.88 |

TABLE 14-continued
| Example # | Stereochemistry | R | R' | R" | M + H | RT |
|---|---|---|---|---|---|---|
| 223 | Racemic | 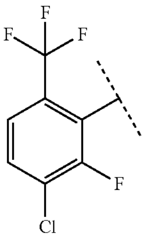 | 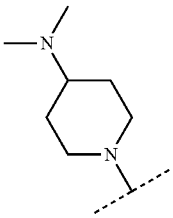 | -4-PhCOOH | 673.5 | 6.67 |
| 224 | Racemic | 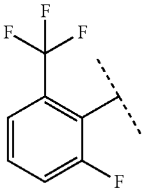 | 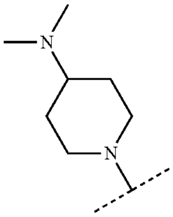 | -4-PhCOOH | 639.5 | 6.33 |
| 225 | Racemic | 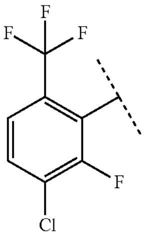 | 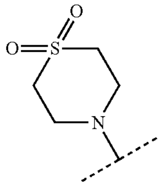 | -4-PhCOOH | 680.41 | 0.55 |
| 226 | Racemic | 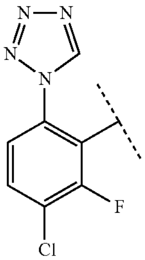 | 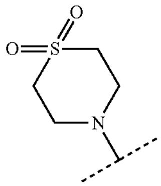 | -4-PhCOOEt | 708.41 | 0.51 |
| 227 | Racemic | 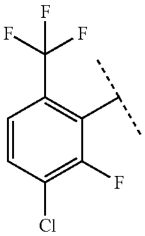 | 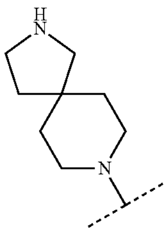 | -4-PhCOOH | 685.4 | 6.92 |
| 228 | Racemic | 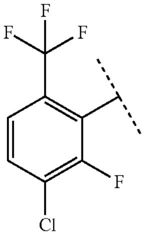 | 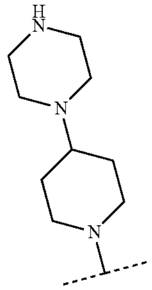 | -4-PhCOOH | 714.3 | 9.77 |
[a]Chiralpak IA-H, 150 x 21 cm ID, 45% (1:1 EtOH-IPA-0.1% DEA)/55% $CO_2$ at 70 mL/min, 100 bar, 35° C.
[b]Chiralcel OD-H, 2 x 20 cm ID, 30% MeOH-0.1% DEA)/70% $CO_2$ at 70 mL/min, 100 bar, 35° C.
[c]Chiralpak AD-H, 250 x 21 cm ID, 45% (1:1 EtOH-IPA-0.1% DEA)/55% $CO_2$ at 60 mL/min, 150 bar, 35° C.

The following examples in Table 15 were made by Ugi reaction as described in Example 1 using appropriate nitrile intermediates. Deprotection with TFA/DCM was carried out where necessary. Single enantiomers were isolated by chiral HPLC at a protected late stage intermediate and then, deprotected where indicated.

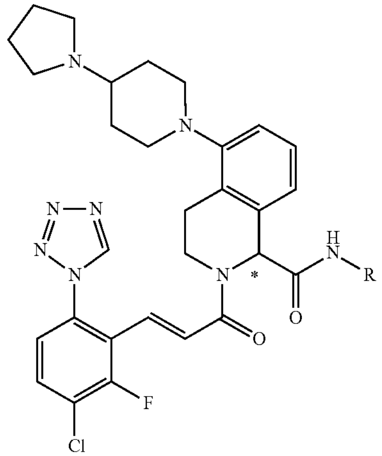

TABLE 15

| Example # | Stereochemistry | R | M + H | RT |
|---|---|---|---|---|
| 229 | Racemic | 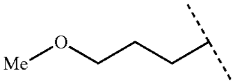 | 651.5 | 5.71 |
| 230 | Racemic | 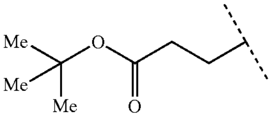 | 707.6 | 6.69 |
| 231 | Racemic | 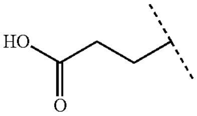 | 651.5 | 5.54 |
| 232 | Racemic | 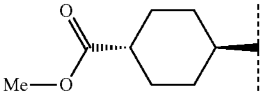 | 719.6 | 6.38 |
| 233 | Racemic | 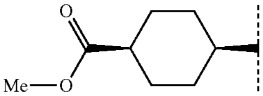 | 719.4 | 6.13 |
| 234 | Racemic | 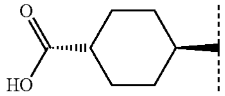 | 705.4 | 5.34 |
| 235 | Racemic | 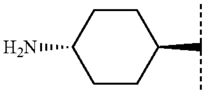 | 676.4 | 4.41 |
| 236 | Racemic | 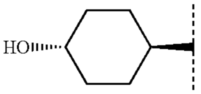 | 677.6 | 5.32 |
| 237 | Racemic | 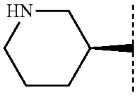 | 662.5 | 4.27 |

TABLE 15-continued

| Example # | Stereochemistry | R | M + H | RT |
|---|---|---|---|---|
| 238 | Racemic | 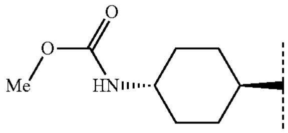 | 734.6 | 6.70 |
| 239 | Racemic | 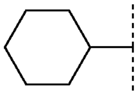 | 661.5 | 6.45 |
| 240 | Racemic | 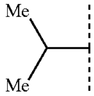 | 621.4 | 4.64 |

Example 241

(E)-4-(2-(3-(3-Chloro-2-fluoro-6-(1H-tetrazol-1-yl)phenyl)acryloyl)-5-(3-(ethoxycarbonyl)-5-methyl-1H-pyrazol-1-yl)-1,2,3,4-tetrahydroisoquinoline-1-carboxamido)benzoic acid

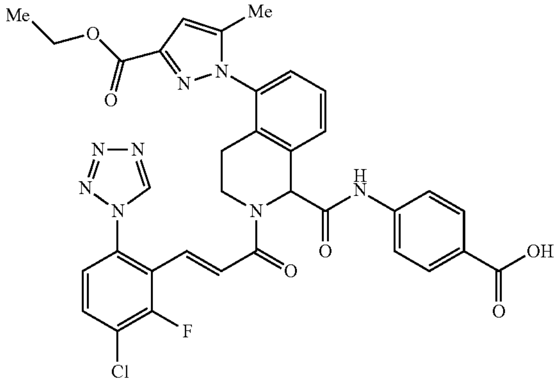 [SMILES: CCOC(=O)c1cc(C)n(-c2cccc3c2CCN(C(=O)/C=C/c2c(-n4cnnn4)ccc(Cl)c2F)C3C(=O)Nc2ccc(C(=O)O)cc2)n1]

241A: A solution of isoquinolin-5-amine (1.442 g, 10 mmol) in $H_2O$ (10 mL) containing concentrated HCl (3.0 mL, 36.5 mmol) at 0° C. was treated dropwise with a solution of sodium nitrite (0.759 g, 11.00 mmol) in $H_2O$ (3 mL). After stirring for an additional hour at 0° C., the contents were transferred to an addition funnel and added drop wise to a vigorously stirred solution of tin(II) chloride dihydrate (5.64 g, 25.00 mmol) in concentrated HCl (25 mL) at 0° C. After stirring for 1 h, the pH was adjusted to 7-8 by adding 10 N NaOH with cooling in an ice bath. The mixture was extracted with $CHCl_3$/MeOH (9:1). The combined organic extracts were dried over $MgSO_4$, filtered, and concentrated to give a light brown solid. Ethyl 2,4-dioxovalerate (1.582 g, 10.00 mmol) was added to a solution of the hydrazine in EtOH and heated at 80° C. After cooling to rt, the reaction mixture was concentrated. The residue was dissolved in EtOAc (75 mL) and washed with saturated $NaHCO_3$ solution, $H_2O$, brine, dried over $Na_2SO_4$, filtered, and concentrated. The crude material was purified by column chromatography. The desired product was isolated as a brown solid. MS(ESI) m/z: 282.0 $(M+H)^+$.

241B: Adam's Catalyst (0.061 g, 0.267 mmol) was added to a solution of 241A (1.5 g, 5.33 mmol) in EtOH (50 mL) and stirred under a hydrogen atmosphere (55 psi) overnight. The reaction mixture was filtered through a plug of Celite®, the filter-cake rinsed with EtOH, and the combined filtrate concentrated. The residue was dissolved in DCM (50 mL), treated with $MnO_2$ (8.34 g, 96 mmol), and left to stir overnight. The reaction mixture was filtered through a plug of Celite® and the filter cake rinsed with DCM/MeOH (9:1). The combined filtrate was concentrated to yield the desired product. MS(ESI) m/z: 284.1 $(M+H)^+$ 241C: 241B (0.150 g, 0.529 mmol) was dissolved in EtOH (10 mL), treated with intermediate 3A (0.142 g, 0.529 mmol) and intermediate 6 (0.108 g, 0.529 mmol) and heated at 60° C. overnight. The reaction mixture was concentrated, dissolved in EtOAc, washed with 1.5M $K_3PO_4$ solution, brine, dried over $Na_2SO_4$, filtered, and concentrated. The t-butyl ester was converted into the corresponding carboxylic acid by treatment with 50% TFA/DCM for 2 h. The reaction mixture was concentrated and purified by reverse phase HPLC. $^1H$ NMR (400 MHz, DMSO-$d_6$) δ 10.89 (s, 1H), 9.85 (s, 1H), 8.00-7.80 (m, 4H), 7.75-7.62 (m, 3H), 7.55-7.46 (m, 1H), 7.41 (s, 1H), 7.14-7.05 (m, 1H), 7.01-6.91 (m, 1H), 6.78 (s, 1H), 5.96 (s, 1H), 4.29 (q, J=7.1 Hz, 2H), 4.11-3.99 (m, 1H), 3.77-3.59 (m, 1H), 2.81-2.67 (m, 1H), 2.44-2.30 (m, 1H), 2.11 (s, 3H), 1.29 (t, J=6.9 Hz, 3H) ppm. MS(ESI) m/z: 699.1 $(M+H)^+$ Analytical HPLC: RT=9.10 min Example 242

(E)-Ethyl 1-(2-(3-(3-chloro-2-fluoro-6-(1H-tetrazol-1-yl)phenyl)acryloyl)-1-(4-fluorophenylcarbamoyl)-1,2,3,4-tetrahydroisoquinolin-5-yl)-5-methyl-1H-pyrazole-3-carboxylate

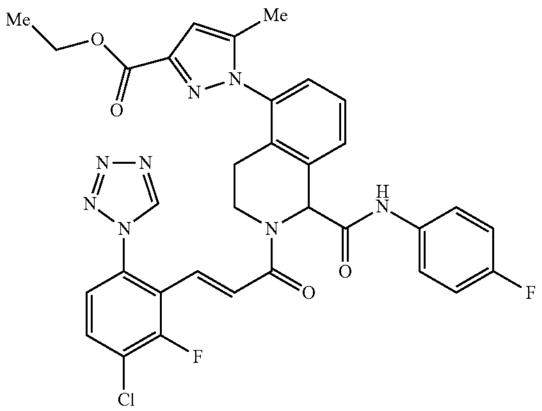 [SMILES: CCOC(=O)c1cc(C)n(-c2cccc3c2CCN(C(=O)/C=C/c2c(-n4cnnn4)ccc(Cl)c2F)C3C(=O)Nc2ccc(F)cc2)n1]

241B (0.150 g, 0.529 mmol) was dissolved in EtOH (10 mL), treated with intermediate 3A (0.142 g, 0.529 mmol) and 1-fluoro-4-isocyanobenzene (0.064 g, 0.529 mmol) and heated at 60° C. overnight. The reaction mixture was concentrated, dissolved in EtOAc, washed with 1.5 M $K_3PO_4$ solution, brine, dried over $Na_2SO_4$, filtered, and concentrated. The reaction mixture was concentrated and purified by reverse phase HPLC. $^1H$ NMR (400 MHz, DMSO-$d_6$) δ 10.63 (1H, s), 9.85 (1H, s), 7.94 (1H, t, J=8.08 Hz), 7.81 (1H, d, J=7.83 Hz), 7.56-7.70 (3H, m), 7.49 (1H, t, J=7.83 Hz), 7.35-7.42 (1H, m), 7.04-7.22 (3H, m), 6.91-7.02 (1H, m), 6.78 (1H, s), 5.93 (1H, s), 4.28 (2H, q, J=7.07 Hz), 4.00-4.11 (1H, m), 3.62-3.75 (1H, m), 2.64-2.78 (1H, m), 2.29-2.41 (1H, m), 2.11 (2H, s), 1.29 (3H, t, J=7.07 Hz) ppm. MS (ESI) m/z: 673.1 $(M+H)^+$ Analytical HPLC: RT=10.54 min.

The following examples in Table 16 were made by Ugi reaction as described in Example 1 using appropriate intermediates. Deprotection with TFA/DCM was carried out where necessary. Single enantiomers were isolated by chiral HPLC at a protected late stage intermediate and then, deprotected where indicated.

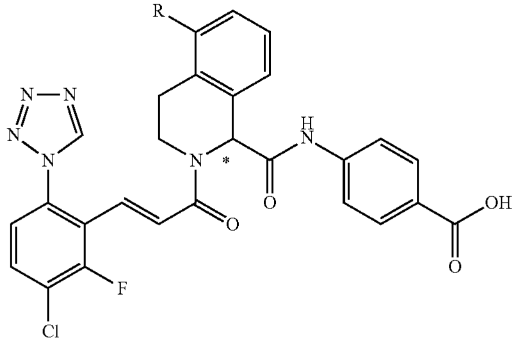

TABLE 16

| Example # | Stereochemistry | R | M + H | RT |
|---|---|---|---|---|
| 243 | Diastereomer | 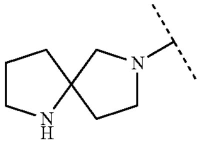 | 671.5 | 9.04 |
| 244 | Diastereomer | 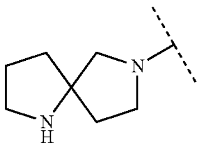 | 671.5 | 9.12 |

TABLE 16-continued
| Example # | Stereochemistry | R | M + H | RT |
|---|---|---|---|---|
| 245 | Diastereomer | 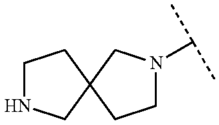 | 671.2 | 5.3* |
| 246 | Diastereomer | 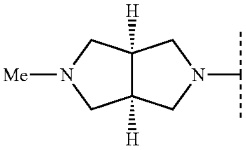 | 671.5 | 5.97 |
| 247 | Diastereomer | 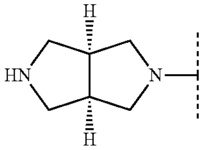 | 657.1 | 6.62 |
| 248 | Diastereomer | 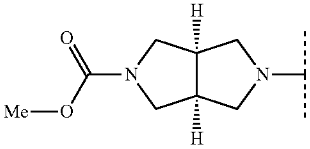 | 715.4 | 9.72 |
| 249 | Diastereomer | 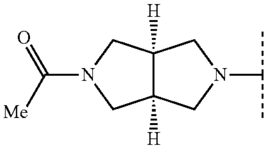 | 699.4 | 8.25 |
| 250 | Diastereomer | 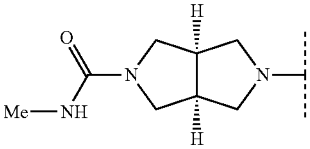 | 714.4 | 7.90 |
| 251 | Diastereomer | 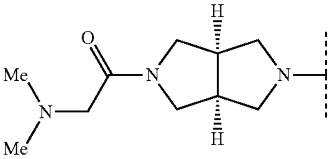 | 742.4 | 5.87 |
| 252 | Racemate | 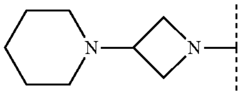 | 685.2 | 4.98* |
*Method B The following examples in Table 17 were made by Ugi reaction as described in Example 1 using appropriate intermediates. Deprotection with TFA/DCM was carried out where necessary. Single enantiomers were isolated by chiral HPLC at a protected late stage intermediate and then, deprotected where indicated.

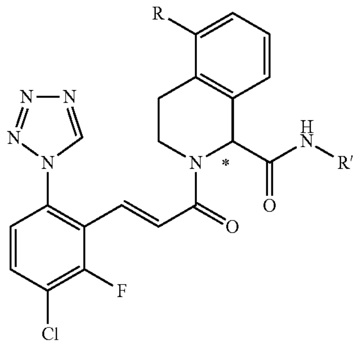

The following examples in Table 18 were made by Ugi reaction as described in Example 1 using appropriate intermediates. Deprotection with TFA/DCM was carried out where necessary. Single enantiomers were isolated by chiral HPLC at a protected late stage intermediate and then, deprotected where indicated.

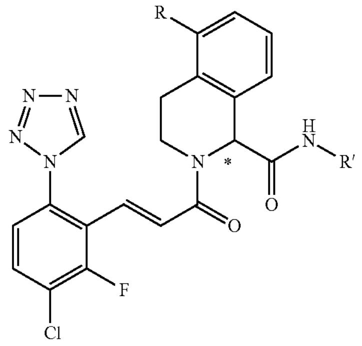

TABLE 17

| Example # | Stereochemistry | R | R' | M + H | RT |
|---|---|---|---|---|---|
| 253 | S-enantiomer[a] | 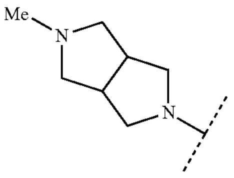 | 4-PhCOOEt | 699.3 | 7.79 |
| 254 | S-enantiomer[a] | 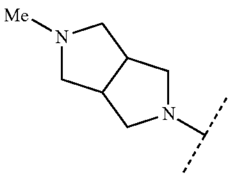 | 4-PhCOOH | 671.3 | 6.64 |
| 255 | Racemic | 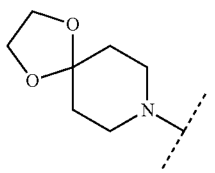 | 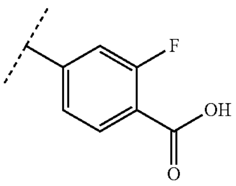 | 706.3 | 9.37 |

[a]Kromasil cellulocoat, 250 x 4.6 mm ID, 40% (MeOH-0.1% DEA)/60% $CO_2$ at 45 mL/min, 100 bar, 40° C.

TABLE 18
| Example # | Stereochemistry | R | R' | M + H | RT |
|---|---|---|---|---|---|
| 256 | Racemic | 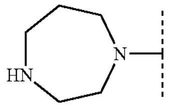 | 4-PhCOOH | 645.2 | 5.42 |
| 257 | Racemic | 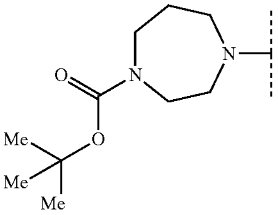 | 4-PhCOOtBu | 801.4 | 13.15 |
| 258 | Racemic | 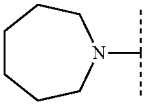 | 4-PhCOOH | 644.3 | 7.82 |
| 259 | Racemic | 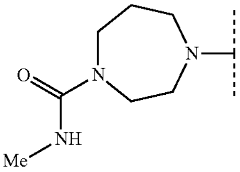 | 4-PhCOOH | 702.3 | 8.14 |
| 260 | S-enantiomer[a] | 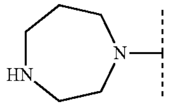 | 4-PhCOOH | 645.2 | 5.02* |
| 261 | Racemic | 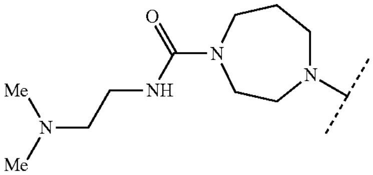 | 4-PhCOOH | 759.3 | 5.46* |
| 262 | Racemic | 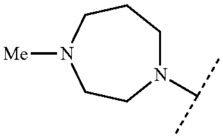 | 4-PhCOOH | 659.2 | 4.90* |
| 263 | Racemic | 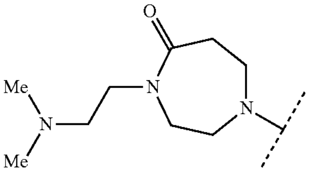 | 4-PhCOOH | 730.3 | 5.06* |
| 264 | Racemic | 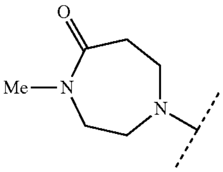 | 4-PhCOOH | 673.3 | 8.36 |
| 265 | S-enantiomer | 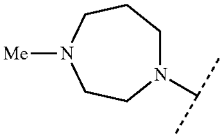 | 4-PhCOOH | 659.2 | 6.75 |

TABLE 18-continued

| Example # | Stereochemistry | R | R' | M + H | RT |
|---|---|---|---|---|---|
| 266 | S-enantiomer | 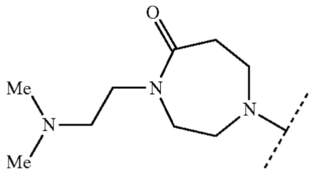 | 4-PhCOOH | 730.4 | 6.33 |

[a]Chiralpak AD-H, 150 x 21 mm ID, 45% (1:1 EtOH-IPA-0.1% DEA)/55% $CO_2$ at 45 mL/min, 150 bar, 40° C.
*Method B The following examples in Table 19 were made by Ugi reaction as described in Example 206 using appropriate intermediates. Deprotection with TFA/DCM was carried out where necessary. Single enantiomers were isolated by chiral HPLC at a protected late stage intermediate and then, deprotected where indicated.

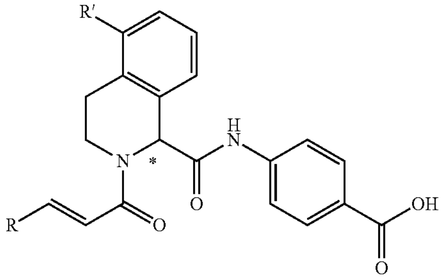

TABLE 19

| Example # | Stereochemistry | R | R' | M + H | RT |
|---|---|---|---|---|---|
| 267 | S-enantiomer[a] | 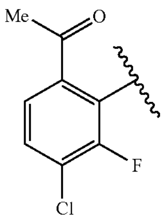 [SMILES: *c1c(C(C)=O)ccc(Cl)c1F] | 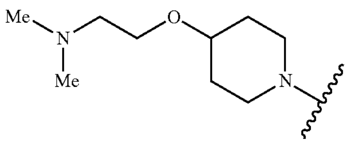 [SMILES: *N1CCC(OCCN(C)C)CC1] | 691.3 | 5.86 |
| 268 | S-enantiomer[b] | 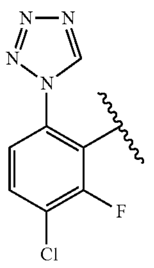 [SMILES: *c1c(-n2cnnn2)ccc(Cl)c1F] | 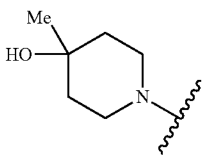 [SMILES: *N1CCC(C)(O)CC1] | 660.2 | 6.68 |

TABLE 19-continued

| Example # | Stereochemistry | R | R' | M + H | RT |
|---|---|---|---|---|---|
| 269 | Racemic | 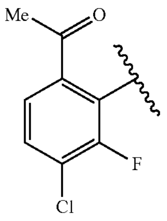 [SMILES: *c1c(C(C)=O)ccc(Cl)c1F] | 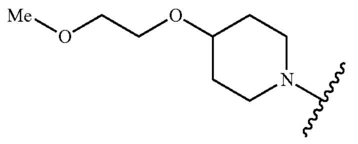 [SMILES: *N1CCC(OCCOC)CC1] | 678.2 | 8.44 |
| 270 | S-enantiomer[a] | 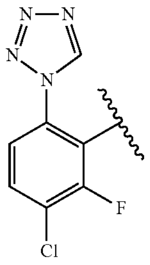 [SMILES: *c1c(-n2cnnn2)ccc(Cl)c1F] | 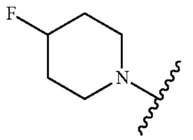 [SMILES: *N1CCC(F)CC1] | 648.2 | 9.91 |

[a]Chiralpak AD-H, 250 x 21 mm ID, 45% (1:1 EtOH-IPA-0.1% DEA)/55% $CO_2$ at 65 mL/min, 150 bar, 45° C.
[b]Chiralpak AD-H, 250 x 21 mm ID, 40% (1:1 EtOH-IPA-0.1% DEA)/60% $CO_2$ at 65 mL/min, 150 bar, 45° C.

VII. Polymorphs

The compounds of the present invention may exist as polymorphs. As used herein "polymorph" refers to crystalline forms having the same chemical composition but different spatial arrangements of the molecules, and/or ions forming the crystal. The present invention provides crystalline forms as a pharmaceutically acceptable form. The term "pharmaceutically acceptable", as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

In one embodiment, a compound of the present invention is in substantially pure form. The term "substantially pure", as used herein, means a compound having a purity greater than about 90% including greater than 90, 91, 92, 93, 94, 95, 96, 97, 98, and 99 weight %, and also including equal to about 100 weight % of the compound, based on the weight of the compound. The remaining material comprises other form(s) of the compound, and/or reaction impurities and/or processing impurities arising from its preparation. For example, a crystalline form of a compound may be deemed substantially pure in that it has a purity greater than 90 weight %, as measured by means that are at this time known and generally accepted in the art, where the remaining less than 10 weight % of material comprises other form(s) of the compound and/or reaction impurities and/or processing impurities.

Samples of the crystalline forms may be provided with substantially pure phase homogeneity, indicating the presence of a dominant amount of a single crystalline form and optionally minor amounts of one or more other crystalline forms. The presence of more than one crystalline form in a sample may be determined by techniques such as powder X-ray diffraction (PXRD) or solid state nuclear magnetic resonance spectroscopy (SSNMR). For example, the presence of extra peaks in the comparison of an experimentally measured PXRD pattern with a simulated PXRD pattern may indicate more than one crystalline form in the sample. The simulated PXRD may be calculated from single crystal X-ray data. see Smith, D. K., "*A FORTRAN Program for Calculating X-Ray Powder Diffraction Patterns*," Lawrence Radiation Laboratory, Livermore, Calif., UCRL-7196, April 1963. Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated XRPD pattern. Most preferred is a crystalline form having substantially pure phase homogeneity with less than 1% of the total peak area in the experimentally measured PXRD pattern arising from the extra peaks that are absent from the simulated PXRD pattern.

The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Ind., 1999.

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility. Suitable solvents for preparing crystals include polar and nonpolar solvents.

In one method to prepare crystals, the compound of the present invention is suspended and/or stirred in a suitable solvent to afford a slurry, which may be heated to promote dissolution. The term "slurry", as used herein, means a saturated solution of the compound and a solvent at a given temperature. Suitable solvents in this regard include, for example, polar aprotic solvents, and polar protic solvents, and nonpolar solvents, and mixtures of two or more of these.

Suitable polar aprotic solvents include, for example, dicholomethane ($CH_2Cl_2$ or DCM), tetrahydrofuran (THF), acetone, methyl ethyl ketone (MEK), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN or MeCN), dimethylsulfoxide (DMSO), propionitrile, ethyl formate, methyl acetate (MeOAc), ethyl acetate (EtOAc), isopropyl acetate (IpOAc), butyl acetate (BuOAc), t-butyl acetate, hexachloroacetone, dioxane, sulfolane, N,N-dimethylpropionamide, nitromethane, nitrobenzene and hexamethylphosphoramide.

Suitable polar protic solvents include, for example, alcohols and glycols, such as $H_2O$, methanol, ethanol, 1-propanol, 2-propanol, isopropanol (IPA), 1-butanol (1-BuOH), 2-butanol (2-BuOH), i-butyl alcohol, t-butyl alcohol, 2-nitroethanol, 2-fluoroethanol, 2,2,2-trifluoroethanol, ethylene glycol, 2-methoxyethanol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol and methyl t-butyl ether (MTBE).

Preferred solvents include, for example, acetone, $H_2O$, $CH_2Cl_2$, methanol, ethanol, MEK, IPA, and EtOAc.

Other solvents suitable for the preparation of slurries, in addition to those exemplified above, would be apparent to one skilled in the art, based on the present disclosure.

Seed crystals may be added to any crystallization mixture to promote crystallization. As will be clear to the skilled artisan, seeding is used as a means of controlling growth of a particular crystalline form or as a means of controlling the particle size distribution of the crystalline product. Accordingly, calculation of the amount of seeds needed depends on the size of the seed available and the desired size of an average product particle as described, for example, in "Programmed cooling of batch crystallizers," J. W. Mullin and J. Nyvlt, *Chemical Engineering Science,* 1971, 26, 369-377. In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity of the desired crystal form or form conversions (i.e. change to amorphous or to another polymorph).

A cooled mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as SSNMR, DSC, PXRD, or the like, to assure formation of the preferred crystalline form of the product. The resulting crystalline form is typically produced in an amount of greater than about 70 weight % isolated yield, but preferably greater than 90 weight % based on the weight of the compound originally employed in the crystallization procedure. The product may be comilled or passed through a mesh screen to delump the product, if necessary.

Crystalline forms may be prepared directly from the reaction medium of the final process step for preparing the compound of the present invention. This may be achieved, for example, by employing in the final process step a solvent or mixture of solvents from which the compound may be crystallized. Alternatively, crystalline forms may be obtained by distillation or solvent addition techniques. Suitable solvents for this purpose include any of those solvents described herein, including protic polar solvents such as alcohols, and aprotic polar solvents such as ketones.

By way of general guidance, the reaction mixture may be filtered to remove any undesired impurities, inorganic salts, and the like, followed by washing with reaction or crystallization solvent. The resulting solution may be concentrated to remove excess solvent or gaseous constituents. If distillation is employed, the ultimate amount of distillate collected may vary, depending on process factors including, for example, vessel size, stirring capability, and the like, by way of general guidance, the reaction solution may be distilled to about {fraction (1/10)} the original volume before solvent replacement is carried out. The reaction may be sampled and assayed to determine the extent of the reaction and the wt % product in accordance with standard process techniques. If desired, additional reaction solvent may be added or removed to optimize reaction concentration. Preferably, the final concentration is adjusted to about 50 wt % at which point a slurry typically results.

It may be preferable to add solvents directly to the reaction vessel without distilling the reaction mixture. Preferred solvents for this purpose are those which may ultimately participate in the crystalline lattice as discussed above in connection with solvent exchange. Although the final concentration may vary depending on desired purity, recovery and the like, the final concentration of the in solution is preferably about 4% to about 7%. The reaction mixture may be stirred following solvent addition and simultaneously warmed. By way of illustration, the reaction mixture may be stirred for about 1 hour while warming to about 70° C. The reaction is preferably filtered hot and washed with either the reaction solvent, the solvent added or a combination thereof. Seed crystals may be added to any crystallization solution to initiate crystallization.

The various forms described herein may be distinguishable from one another through the use of various analytical techniques known to one of ordinary skill in the art. Such techniques include, but are not limited to, solid state nuclear magnetic resonance (SSNMR) spectroscopy, X-ray powder diffraction (PXRD), differential scanning calorimetry (DSC), and/or thermogravimetric analysis (TGA).

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

The crystalline forms of the compound of the present invention may be formulated into pharmaceutical compositions and/or employed in therapeutic and/or prophylactic methods. These methods include, but are not limited to, the administration of the crystalline compound, alone or in combination with one or more other pharmaceutically active agents, including agents that may be useful in the treatment of the disorders mentioned herein.

The crystalline forms of the compound of the present invention and pharmaceutical composition thereof may be useful in inhibiting Factor XIa. Accordingly, the present invention provides methods for the treatment and/or prevention of thromboembolic disorders in mammals (i.e., factor XIa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular thromboembolic disorders, and thromboembolic disorders in the chambers of the heart. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor XIa or thrombin.

The methods preferably comprise administering to a patient a pharmaceutically effective amount of the novel crystals of the present invention, preferably in combination with one or more pharmaceutically acceptable carriers and/or excipients. The relative proportions of active ingredient and carrier and/or excipient may be determined, for example, by the solubility and chemical nature of the materials, chosen route of administration and standard pharmaceutical practice.

The crystalline forms of the compound may be administered to a patient in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They may be administered alone, but generally will be administered with a pharmaceutical carrier selected on the basis of the chosen route of administration and standard pharmaceutical practice.

The dosage regimen for the crystalline forms of the compound will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder. Obviously, several unit dosage forms may be administered at about the same time. The dosage of the crystalline form of the compound that will be most suitable for prophylaxis or treatment may vary with the form of administration, the particular crystalline form of the compound chosen and the physiological characteristics of the particular patient under treatment. Broadly, small dosages may be used initially and, if necessary, increased by small increments until the desired effect under the circumstances is reached.

By way of general guidance, in the adult, suitable doses may range from about 0.001 to about 1000 mg/Kg body weight, and all combinations and subcombinations of ranges and specific doses therein. Preferred doses may be from about 0.01 to about 100 mg/kg body weight per day by inhalation, preferably 0.1 to 70, more preferably 0.5 to 20 mg/Kg body weight per day by oral administration, and from about 0.01 to about 50, preferably 0.01 to 10 mg/Kg body weight per day by intravenous administration. In each particular case, the doses may be determined in accordance with the factors distinctive to the subject to be treated, such as age, weight, general state of health and other characteristics which can influence the efficacy of the medicinal product. The crystalline forms of the compound may be administered in a single daily dose, or the total daily dosage may be administered in divided doses of two, three, or four times daily.

For oral administration in solid form such as a tablet or capsule, the crystalline forms of the compound can be combined with a non-toxic, pharmaceutically acceptable inert carrier, such as lactose, starch, sucrose, glucose, methylcellulose, magnesium stearate, dicalcium phosphate, calcium sulfate, mannitol, sorbitol and the like.

Preferably, in addition to the active ingredient, solid dosage forms may contain a number of additional ingredients referred to herein as "excipients". These excipients include among others diluents, binders, lubricants, glidants and disintegrants. Coloring agents may also be incorporated. "Diluents", as used herein, are agents which impart bulk to the formulation to make a tablet a practical size for compression. Examples of diluents are lactose and cellulose. "Binders", as used herein, are agents used to impart cohesive qualities to the powered material to help ensure the tablet will remain intact after compression, as well as improving the free-flowing qualities of the powder. Examples of typical binders are lactose, starch and various sugars. "Lubricants", as used herein, have several functions including preventing the adhesion of the tablets to the compression equipment and improving the flow of the granulation prior to compression or encapsulation. Lubricants are in most cases hydrophobic materials. Excessive use of lubricants is undesired, however, as it may result in a formulation with reduced disintegration and/or delayed dissolution of the drug substance. "Glidants", as used herein, refer to substances which may improve the flow characteristics of the granulation material. Examples of glidants include talc and colloidal silicon dioxide. "Disintegrants", as used herein, are substances or a mixture of substances added to a formulation to facilitate the breakup or disintegration of the solid dosage form after administration. Materials that may serve as disintegrants include starches, clays, celluloses, algins, gums and cross-linked polymers. A group of disintegrants referred to as "super-disintegrants" generally are used at a low level in the solid dosage form, typically 1% to 10% by weight relative to the total weight of the dosage unit. Croscarmelose, crospovidone and sodium starch glycolate represent examples of a cross-linked cellulose, a cross-linked polymer and a cross-linked starch, respectively. Sodium starch glycolate swells seven- to twelve-fold in less than 30 seconds effectively disintegrating the granulations that contain it.

The disintegrant preferably used in the present invention is selected from the group comprising modified starches, croscarmallose sodium, carboxymethylcellulose calcium and crospovidone. A more preferred disintegrant in the present invention is a modified starch such as sodium starch glycolate.

Preferred carriers include capsules or compressed tablets which contain the solid pharmaceutical dosage forms described herein. Preferred capsule or compressed tablet forms generally comprise a therapeutically effective amount of the crystalline forms of the compound and one or more disintegrants in an amount greater than about 10% by weight relative to the total weight of the contents of the capsule or the total weight of the tablet.

Preferred capsule formulations may contain the crystalline forms of the compound in an amount from about 5 to about 1000 mg per capsule. Preferred compressed tablet formulations contain the crystalline forms of the compound in an amount from about 5 mg to about 800 mg per tablet. More preferred formulations contain about 50 to about 200 mg per capsule or compressed tablet. Preferably, the capsule or compressed tablet pharmaceutical dosage form comprises a therapeutically effective amount of the crystalline forms; a surfactant; a disintegrant; a binder; a lubricant; and optionally additional pharmaceutically acceptable excipients such as diluents, glidants and the like; wherein the disintegrant is selected from modified starches; croscarmallose sodium, carboxymethylcellulose calcium and crospovidone.

For oral administration in liquid form, the crystalline forms of the compound can be combined with any oral, non-toxic pharmaceutically acceptable inert carrier such as ethanol, glycerol, water and the like. The liquid composition may contain a sweetening agent which to make the compositions more palatable. The sweetening agent can be selected from a sugar such as sucrose, mannitol, sorbitol, xylitol, lactose, etc. or a sugar substitute such as cyclamate, saccaharin, aspartame, etc. If sugar substitutes are selected as the sweetening agent the amount employed in the compositions of the invention will be substantially less than if sugars are employed. Taking this into account, the amount of sweetening agent may range from about 0.1 to about 50% by weight, and all combinations and subcombinations of ranges and specific amounts therein. Preferred amounts range from about 0.5 to about 30% by weight.

The more preferred sweetening agents are the sugars and particularly sucrose. The particle size of the powdered sucrose used has been found to have a significant influence in the physical appearance of the finished composition and its ultimate acceptance for taste. The preferred particle size of the sucrose component when used is in the range of from 200 to less than 325 mesh US Standard Screen, and all combinations and subcombinations of ranges and specific particle sizes therein.

Sterile injectable solutions may be prepared by incorporating the crystalline forms of the compound in the required amounts, in the appropriate solvent, with various of the other ingredients enumerated herein, as required, followed by filtered sterilization. Generally, dispersions may be prepared by incorporating the sterilized active ingredient into a sterile vehicle which contains the dispersion medium and any other required ingredients. In the case of sterile powders for the preparation of sterile injectable solutions, the preferred methods of preparation may include vacuum drying and the freeze drying technique which may yield a powder of the active ingredient, plus any additional desired ingredient from the previously sterile-filtered solution thereof As would be apparent to a person of ordinary skill in the art, once armed with the teachings of the present disclosure, when dissolved, a crystalline compound loses its crystalline structure, and is therefore considered to be a solution of the compound. All forms of the present invention, however, may be used for the preparation of liquid formulations in which the compound may be, for example, dissolved or suspended. In addition, the crystalline forms of the compound may be incorporated into solid formulations.

The liquid compositions may also contain other components routinely utilized in formulating pharmaceutical compositions. One example of such components is lecithin. Its use in compositions of the invention as an emulsifying agent in the range of from 0.05 to 1% by weight, and all combinations and subcombinations of ranges and specific amounts therein. More preferably, emulsifying agents may be employed in an amount of from about 0.1 to about 0.5% by weight. Other examples of components that may be used are antimicrobial preservatives, such as benzoic acid or parabens; suspending agents, such as colloidal silicon dioxide; antioxidants; topical oral anesthetics; flavoring agents; and colorants.

The selection of such optional components and their level of use in the compositions of the invention is within the level of skill in the art and will be even better appreciated from the working examples provided hereinafter.

The crystalline forms of the compound may also be coupled with soluble polymers as targetable drug carriers. Such polymers can include polyvinylpyrrolidine pyran copolymer, polyhydroxypropylmethacrylamide-phenol, polyhydroxyethyl-aspartamidephenol or polyethylene oxide-polylysine substituted with palmitolyl residues. Furthermore, the crystalline compound may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Gelatin capsules of the crystalline forms of the compound may contain the crystalline compound and the liquid or solid compositions described herein. Gelatin capsules may also contain powdered carriers such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Tablets can be sugar coated or film coated to mask any unpleasant taste and to protect the tablet from the atmosphere or enteric coated for selective disintegration in the gastrointestinal track.

In general, water, a suitable oil, saline, aqueous dextrose (glucose), and related sugar solutions and glycols, such as propylene glycol or polyethylene glycols are suitable carriers for parenteral solutions. Solutions for parenteral solutions are prepared by dissolving the crystalline compound in the carrier and, if necessary, adding buffering substances. Anti-oxidizing agents such as sodium bisulfite, sodium sulfite, or ascorbic acid either alone or combined, are suitable stabilizing agents. Citric acid and its salts and sodium EDTA may also be employed. Parenteral solutions may also contain preservatives, such as benzalkonium chloride, methyl- or propyl-paraben and chlorobutanol.

Suitable pharmaceutical carriers are described in Remington's Pharmaceutical Sciences, Mack Publishing Co., the disclosures of which are hereby incorporated herein by reference, in their entireties. Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient (i.e., Factor XIa inhibitor), 150 mg of lactose, 50 mg of cellulose, and 6 mg magnesium stearate.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Nasal Spray

An aqueous solution is prepared such that each 1 mL contains 10 mg of active ingredient, 1.8 mg methylparaben, 0.2 mg propylparaben and 10 mg methylcellulose. The solution is dispensed into 1 mL vials.

Lung Inhaler

A homogeneous mixture of the active ingredient in polysorbate 80 is prepared such that the final concentration of the active ingredient will be 10 mg per container and the final concentration of polysorbate 80 in the container will be 1% by weight. The mixture is dispensed into each can, the valves are crimped onto the can and the required amount of dichlorotetrafluoroethane is added under pressure.

The preferred crystalline form of the compound may serve as component (a) of this invention and can independently be in any dosage form, such as those described above, and can also be administered in various combinations, as described above. In the following description component (b) is to be understood to represent one or more agents as described herein suitable for combination therapy.

Thus, the crystalline forms of the compound may be used alone or in combination with other diagnostic, anticoagulant, antiplatelet, fibrinolytic, antithrombotic, and/or profibrinolytic agents. For example, adjunctive administration of Factor XIa inhibitors with standard heparin, low molecular weight heparin, direct thrombin inhibitors (i.e. hirudin), aspirin, fibrinogen receptor antagonists, streptokinase, urokinase and/or tissue plasminogen activator may result in improved antithrombotic or thrombolytic efficacy or efficiency. The crystals described herein may be administered to treat thrombotic complications in a variety of animals, such as primates, including humans, sheep, horses, cattle, pigs, dogs, rats and mice Inhibition of Factor XIa may be useful not only in the anticoagulant therapy of individuals having thrombotic conditions, but also when inhibition of blood coagulation may be required, such as to prevent coagulation of stored whole blood and to prevent coagulation in other biological samples for testing or storage. Thus, any Factor XIa inhibitor, including the crystalline forms of the compound as described herein, can be added to or contacted with any medium containing or suspected of containing Factor XIa and in which it may be desired to inhibit blood coagulation.

The crystalline forms of the compound may be used in combination with any antihypertensive agent or cholesterol or lipid regulating agent, or concurrently in the treatment of restenosis, atherosclerosis or high blood pressure. Some examples of agents that may be useful in combination with a novel form of the compound according to the present invention in the treatment of high blood pressure include, for example, compounds of the following classes: beta-blockers, ACE inhibitors, calcium channel antagonists and alpha-receptor antagonists. Some examples of agents that may be useful in combination with a compound according to the invention in the treatment of elevated cholesterol levels or disregulated lipid levels include compounds known to be HMGCoA reductase inhibitors, or compounds of the fibrate class.

Accordingly, components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the reverse order. If component (b) contains more than one agent, these agents may be administered together or in any order. When not administered at the same time, preferably the administration of component (a) and (b) occurs less than about one hour apart. Preferably, the route of administration of component (a) and (b) is oral. Although it may be preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

Pharmaceutical kits which may be useful for the treatment of various disorders, and which comprise a therapeutically effective amount of a pharmaceutical composition comprising a novel form of the compound in one or more sterile containers, are also within the ambit of the present invention. The kits may further comprise conventional pharmaceutical kit components which will be readily apparent to those skilled in the art, once armed with the present disclosure. Sterilization of the container may be carried out using conventional sterilization methodology well known to those skilled in the art.

Example 271

Preparation of Single Crystal Forms H.5-1 and HCl:SA-1

271A: Single Crystal X-Ray Measurement of Forms H.5-1 and HCl:SA-1

Single crystal X-ray data were collected on a Bruker AXS APEX II diffractometer with MicroStarH generator using Cu Kα radiation (λ=1.5418 Å). Indexing and processing of the measured X-ray intensity data were carried out with the APEX2 software suite (Bruker AXS, Inc., Madison, Wis., USA). The structure was solved by direct methods and refined on the basis of observed reflections using SHELXTL crystallographic package (Bruker AXS, Inc., Madison, Wis., USA). The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$, while $R_w=[\Sigma_w(|F_o|-|F_c|)^2/\Sigma_w|F_o|_2]^{1/2}$, where w is an appropriate weighting function based on errors in the observed intensities. Difference Fourier maps were examined at all stages of refinement. All non-hydrogen atoms were refined with anisotropic thermal displacement parameters. Hydrogen atoms were calculated from an idealized geometry with standard bond lengths and angles and refined using a riding model.

271B: Preparation of Single Crystal Form H.5-1

Crystal form H.5-1 (hemi-hydrate) was prepared by adding 3 mg of (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid to 0.7 mL of ethyl acetate and methanol solution (1:1). Yellow prism shaped crystals were obtained after one day of slow evaporation of solution at room temperature.

Crystal Structure Data:

Unit Cell Dimensions:

a=13.6547(3) Å b=18.7590(3) Å c=24.7370(5) Å

α=90°

β=90°

γ=90°

Volume=6336.3(2) $Å^3$

Crystal system: Orthorhombic

Space group: $12(1)_2(1)_2(1)$

Molecules/asymmetric unit: 1

Density (calculated)=1.401 $Mg/m^3$

Measurement of the crystalline form is at a temperature of about 23° C.

TABLE 20

Atomic coordinates ($\times 10^4$) and equivalent isotropic displacement parameters ($Å^2 \times 10^3$) for Compound (I) H.5-1.

| | x | y | z | U(eq)* |
|---|---|---|---|---|
| Cl(1) | 1142(1) | 8638(1) | 1383(1) | 89(1) |
| F(1) | 1133(2) | 7271(1) | 862(1) | 67(1) |
| O(1) | 1102(2) | 5533(1) | −724(1) | 52(1) |
| O(2) | −779(1) | 4373(1) | 15(1) | 48(1) |
| O(3) | −4534(2) | 4606(1) | −1807(1) | 62(1) |
| O(4) | −3952(2) | 3964(2) | −2477(1) | 109(1) |
| O(5) | 3532(2) | 3748(1) | 1408(1) | 63(1) |
| N(1) | 1127(2) | 8164(1) | −968(1) | 56(1) |
| N(2) | 1654(2) | 7703(2) | −1270(1) | 73(1) |
| N(3) | 1416(3) | 7825(2) | −1768(2) | 91(1) |
| N(4) | 759(3) | 8363(2) | −1810(1) | 97(1) |
| N(5) | 1100(2) | 5019(1) | 102(1) | 35(1) |
| N(6) | −311(2) | 4095(1) | −837(1) | 46(1) |
| N(7) | 2057(2) | 3304(1) | 1616(1) | 43(1) |
| N(8) | 2218(2) | 3810(1) | 2664(1) | 57(1) |
| C(1) | 1203(2) | 8493(2) | 699(1) | 57(1) |
| C(2) | 1257(2) | 9049(2) | 342(2) | 59(1) |
| C(3) | 1267(2) | 8920(2) | −203(2) | 54(1) |
| C(4) | 1218(2) | 8232(2) | −398(1) | 46(1) |
| C(5) | 1210(2) | 7639(1) | −54(1) | 41(1) |
| C(6) | 1193(2) | 7804(2) | 496(1) | 49(1) |
| C(7) | 593(3) | 8565(2) | −1310(2) | 81(1) |
| C(8) | 1150(2) | 6900(1) | −250(1) | 42(1) |
| C(9) | 1279(2) | 6305(1) | 22(1) | 45(1) |
| C(10) | 1151(2) | 5598(1) | −230(1) | 38(1) |
| C(11) | 947(2) | 4321(1) | −154(1) | 33(1) |
| C(12) | 1229(2) | 3707(1) | 214(1) | 36(1) |
| C(13) | 1543(2) | 3812(1) | 746(1) | 35(1) |
| C(14) | 1604(2) | 4554(1) | 977(1) | 38(1) |
| C(15) | 912(2) | 5043(1) | 686(1) | 39(1) |
| C(16) | 1171(2) | 3021(1) | 5(1) | 50(1) |
| C(17) | 1412(2) | 2438(2) | 321(1) | 59(1) |
| C(18) | 1711(2) | 2537(2) | 845(1) | 55(1) |
| C(19) | 1785(2) | 3214(1) | 1053(1) | 41(1) |
| C(20) | −134(2) | 4263(1) | −318(1) | 35(1) |
| C(21) | −1221(2) | 4098(2) | −1108(1) | 42(1) |
| C(22) | −1223(3) | 3919(2) | −1650(1) | 76(1) |
| C(23) | −2072(3) | 3948(2) | −1947(1) | 78(1) |
| C(24) | −2943(2) | 4163(2) | −1711(1) | 47(1) |
| C(25) | −2940(2) | 4313(1) | −1170(1) | 40(1) |
| C(26) | −2096(2) | 4271(1) | −864(1) | 42(1) |
| C(27) | −3846(3) | 4228(2) | −2041(1) | 57(1) |
| C(28) | 2912(2) | 3605(2) | 1747(1) | 45(1) |
| C(29) | 3099(2) | 3770(2) | 2335(1) | 56(1) |
| C(30) | 1304(2) | 3112(2) | 2016(1) | 59(1) |
| C(31) | 1666(3) | 3151(2) | 2584(1) | 67(1) |
| C(32) | 2477(4) | 3923(2) | 3236(1) | 90(1) |
| O(1S) | 1006(2) | 5000 | 2500 | 50(1) |

*U(eq) is defined as one third of the trace of the orthogonalized $U^{ij}$ tensor.

271C: Preparation of Single Crystal Form HCl:SA-1

Crystal form HCl:SA-1(solvated mono-HCl salt) was prepared by adding 2 mg of Compound (I) to 0.7 mL of methanol, 2-butanone and butyl acetate solution (2:1:1). Yellow prism shaped crystals were obtained after one day of slow evaporation of solution at room temperature.

Crystal Structure Data:

Unit Cell Dimensions:

a=8.3746(2) Å b=20.2236(5) Å c=21.3099(6) Å

α=90°

β=90°

γ=90°

Volume=3609.14(16) $Å^3$

Crystal system: Orthorhombic

Space group: $P2(1)_2(1)_2(1)$
Molecules/asymmetric unit: 1
Density (calculated)=1.368 $Mg/m^3$
wherein measurement of the crystalline form is at a temperature of about 23° C.

TABLE 21

Atomic coordinates ($\times 10^4$) and equivalent isotropic displacement parameters ($Å^2 \times 10^3$) for Compound (I) HCl:SA-1

| | x | y | z | U(eq)* |
|---|---|---|---|---|
| Cl(2) | 4183(3) | 7590(1) | 7388(1) | 73(1) |
| C(1) | 5350(8) | 5357(3) | −5(3) | 58(2) |
| C(2) | 5189(9) | 5113(3) | 606(3) | 62(2) |
| C(3) | 6122(9) | 4563(3) | 743(3) | 62(2) |
| C(4) | 7131(8) | 4259(3) | 322(4) | 63(2) |
| C(5) | 7186(9) | 4508(4) | −278(4) | 71(2) |
| C(6) | 6312(9) | 5055(4) | −435(3) | 72(2) |
| C(7) | 3624(12) | 6026(4) | −680(4) | 87(2) |
| C(8) | 4120(11) | 5408(4) | 1083(3) | 76(2) |
| C(9) | 3311(10) | 5137(4) | 1500(4) | 78(2) |
| C(10) | 2308(8) | 5511(3) | 1938(3) | 57(2) |
| C(11) | 481(11) | 4538(3) | 1991(4) | 79(2) |
| C(12) | −331(9) | 4186(3) | 2541(4) | 71(2) |
| C(13) | −1725(8) | 4599(3) | 2754(3) | 56(2) |
| C(14) | −1568(8) | 5294(3) | 2755(3) | 51(2) |
| C(15) | 41(8) | 5604(3) | 2612(3) | 50(2) |
| C(16) | −3161(9) | 4326(3) | 2946(3) | 59(2) |
| C(17) | −4444(9) | 4719(4) | 3106(3) | 69(2) |
| C(18) | −4286(9) | 5400(4) | 3088(4) | 70(2) |
| C(19) | −2842(8) | 5689(3) | 2911(3) | 60(2) |
| C(20) | 938(8) | 5679(3) | 3244(3) | 54(2) |
| C(21) | 971(8) | 6440(3) | 4151(3) | 53(2) |
| C(22) | 2064(8) | 6122(3) | 4526(3) | 61(2) |
| C(23) | 2282(8) | 6336(4) | 5147(3) | 62(2) |
| C(24) | 1416(8) | 6856(3) | 5378(3) | 54(2) |
| C(25) | 315(9) | 7169(3) | 4999(3) | 64(2) |
| C(26) | 103(9) | 6969(3) | 4387(3) | 62(2) |
| C(27) | 1629(9) | 7122(4) | 6032(3) | 67(2) |
| C(28) | −4232(14) | 3275(4) | 2493(4) | 101(3) |
| C(29) | −3869(13) | 2532(4) | 2464(4) | 96(3) |
| C(30) | −2699(9) | 2550(3) | 3483(3) | 66(2) |
| C(31) | −2625(9) | 3285(3) | 3458(3) | 60(2) |
| C(32) | −5588(10) | 2286(4) | 3384(5) | 102(3) |
| Cl(1) | 8255(3) | 3595(1) | 563(1) | 95(1) |
| F(1) | 6062(6) | 4310(2) | 1340(2) | 93(1) |
| N(1) | 4510(8) | 5920(3) | −180(3) | 71(2) |
| N(2) | 4579(11) | 6492(3) | 148(3) | 96(2) |
| N(3) | 3701(14) | 6911(4) | −149(5) | 123(3) |
| N(4) | 3089(12) | 6638(4) | −679(4) | 116(3) |
| N(5) | 1037(7) | 5207(2) | 2179(2) | 58(1) |
| N(6) | 645(7) | 6263(2) | 3524(2) | 58(1) |
| N(7) | −3312(7) | 3606(2) | 2977(3) | 60(1) |
| N(8) | −3972(7) | 2250(3) | 3097(3) | 68(2) |
| O(1) | 2620(6) | 6081(2) | 2096(2) | 70(1) |
| O(2) | 1744(6) | 5235(2) | 3465(2) | 63(1) |
| O(3) | 971(7) | 7602(3) | 6233(2) | 91(2) |
| O(4) | 2705(7) | 6777(2) | 6357(2) | 81(2) |
| O(5) | −1867(7) | 3575(2) | 3864(3) | 80(2) |
| O(1S) | 8222(7) | 5981(2) | 1227(2) | 70(1) |
| O(2S) | 489(6) | 5435(3) | 69(3) | 103(2) |
| O(3SB) | 9450(30) | 6486(13) | 631(17) | 126(8) |
| O(3SA) | 9170(30) | 6463(11) | 1022(13) | 136(7) |
| O(3SC) | 9560(30) | 6237(13) | 140(14) | 137(8) |

*U(eq) is defined as one third of the trace of the orthogonalized $U^{ij}$ tensor.

Example 272

272A: Preparation of Form HCl:SA-1

Figure 4:
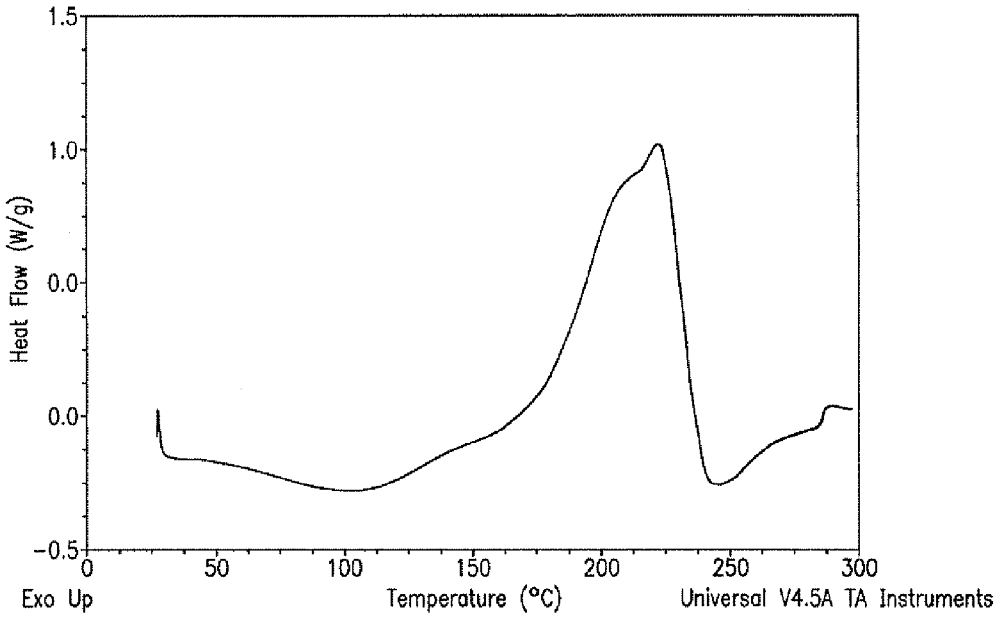
FIG. 4 is a differential scanning calorimetry thermogram of Form HCl:SA-1 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.
Figure 5:
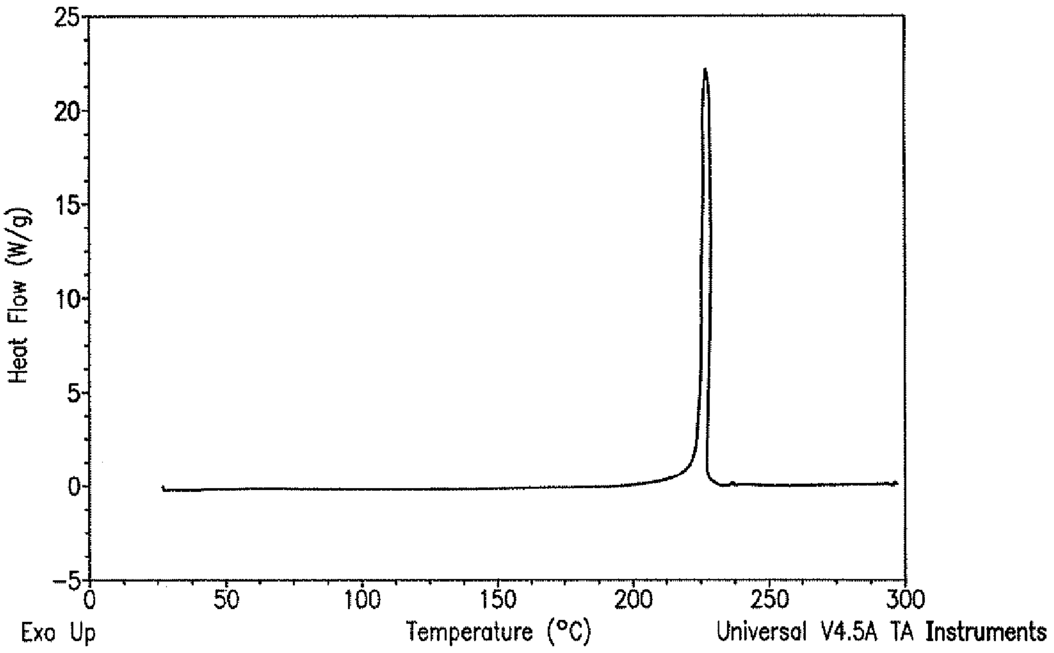
FIG. 5 is a differential scanning calorimetry thermogram of Form P13 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.
Figure 7:
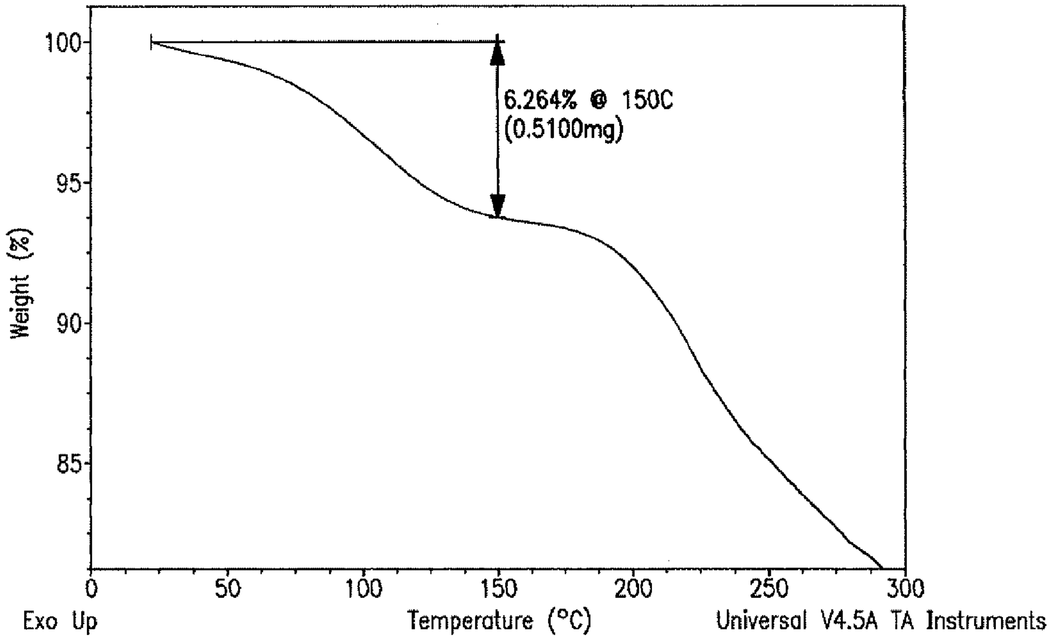
FIG. 7 is a thermogravimetric analysis thermogram of Form HCl:SA-1 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.
Figure 8:
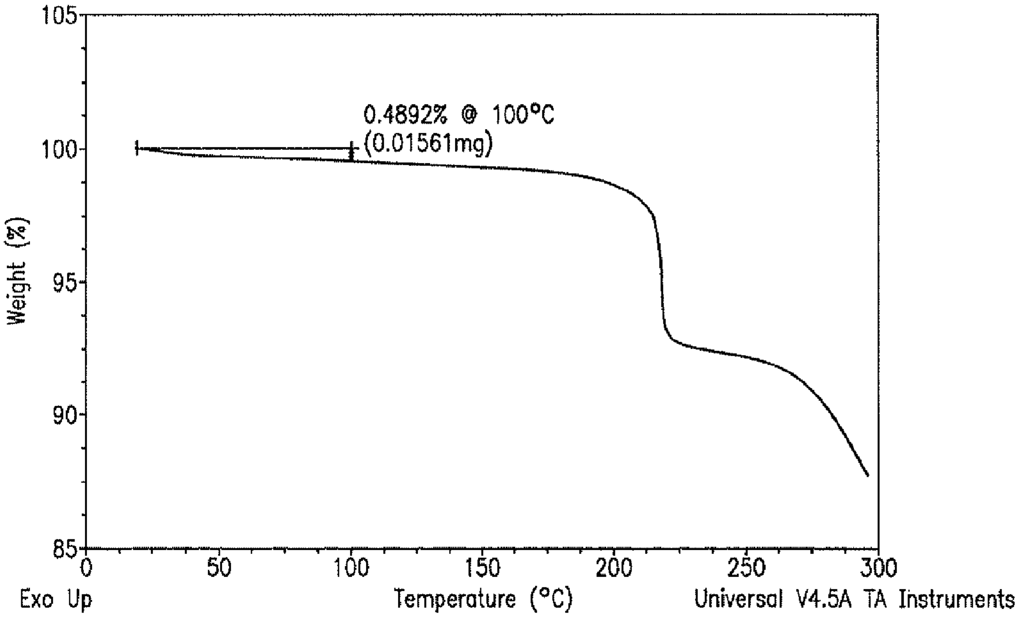
FIG. 8 is a thermogravimetric analysis thermogram of Form P13 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido) benzoic acid.

In a reactor, 415 g of dried crude Compound (I) was dissolved in 9.0 kg of a solution of 200 Proof Ethanol and purified water (70:30). The batch was heated to 66° C. and polish filtered into another reactor. 708 g of the Ethanol/water solution was used to rinse the first reactor and transferred through the filter into the reactor containing the solution mixture. The temperature of the batch was lowered to 50° C. and 2.24 g of Compound (I) was added in one portion. After 30 minutes the batch was cooled to 0° C. over 4 h and allowed to age at that temperature for 60 minutes. The temperature of the batch was then increased to 50° C. over a 2 h period and held for an additional 30 minutes. Again, the batch temperature was then reduced to 0° C. over 4 h and 2.9 L of 200 Proof ethanol was added to the batch. The slurry was filtered at 0° C. and the wet cake was washed twice with 0.9 L of 200 Proof ethanol. The wet cake was dried in a vacuum oven at 40° C. for a minimum of 12 h and until the ethanol content is <6.6 weight percent. The obtained crystal was subjected to PXRD (GADDS-NB), hybrid PXRD (from isostructural analog), DSC and TGA analyses and the results are shown in FIGS. 1, 4, and 7.

PXRD data were obtained using a Bruker C2 GADDS. The radiation was Cu Kα (40 KV, 40 mA). The sample-detector distance was 15 cm. Powder samples were placed in sealed glass capillaries of 1 mm or less in diameter; the capillary was rotated during data collection. Data were collected approximately for $2 \leq 2\theta \leq 35°$ with a sample exposure time of at least 1000 seconds. The resulting two-dimensional diffraction arcs were integrated to create a traditional 1-dimensional PXRD pattern with a step size of 0.05 degrees 2θ in the approximate range of 2 to 35 degrees N.

"Hybrid" simulated powder X-ray patterns were generated as described in the literature (Yin. S.; Scaringe, R. P.; DiMarco, J.; Galella, M. and Gougoutas, J. Z., *American Pharmaceutical Review,* 2003, 6,2, 80). The room temperature cell parameters were obtained by performing a cell refinement using the CellRefine.xls program. Input to the program includes the 2-theta position of ca. 10 reflections, obtained from the experimental room temperature powder pattern; the corresponding Miller indices, hkl, were assigned based on the single-crystal data collected for an isostructural analog. A crystal structure for the molecule of interest was generated in a two step process: (1) by replacing the analog molecule in the experimental analog crystal structure with the molecule of interest. This step fixes the orientation and position of the molecule of interest in the unit cell of the analog compound; (2) Inserting the molecule of interest into the room temperature cell obtained from the experimental PXRD of the molecule of interest, as described above. In this step, the molecules are inserted in a manner that retains the size and shape of the molecule and the position of the molecules with respect to the cell origin, but, allows intermolecular distances to expand/contract with the cell. A new (hybrid) PXRD was calculated (by either of the software programs, Alex or LatticeView) based on the crystal structure generated as described above.

DSC (Open Pan)

DSC experiments were performed in a TA INSTRUMENTS® model Q2000, Q1000 or 2920. The sample (about 2-10 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

TGA (Open Pan)

TGA experiments were performed in a TA INSTRUMENTS® model Q5000, Q500 or 2950. The sample (about 4-30 mg) was placed in a platinum pan previously tared. The weight of the sample was measured accurately and recorded to a thousandth of a milligram by the instrument. The furnace was purged with nitrogen gas at 100 mL/min. Data were collected between room temperature and 300° C. at 10° C./min heating rate.

Example 273

273A: Preparation of Form H.5-1

Figure 2:
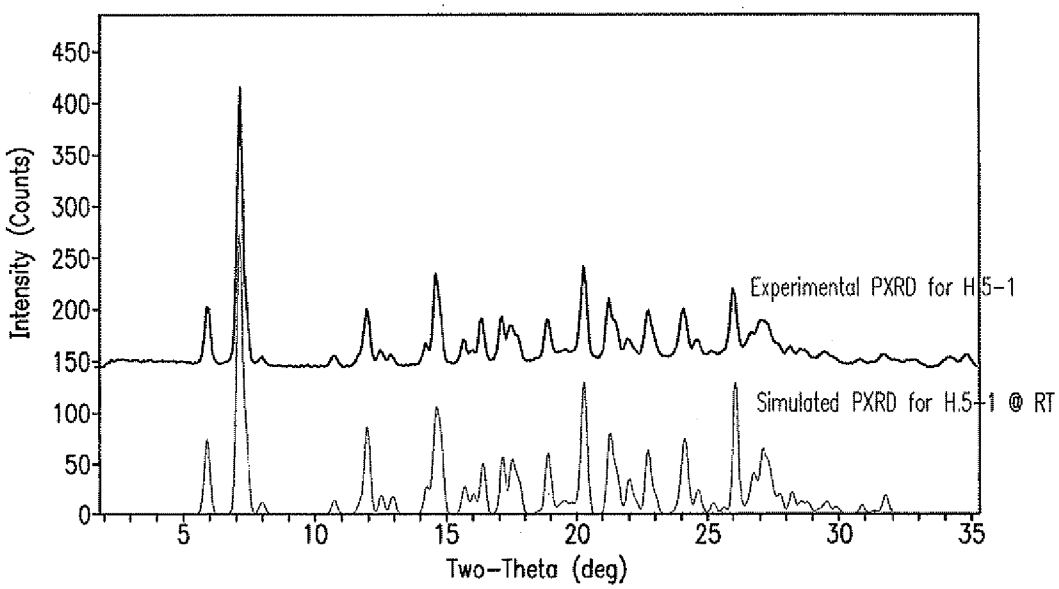
FIG. 2 shows the observed and calculated (room temperature) powder X-ray diffraction patterns (CuKα λ=1.5418 Å) of Form H.5-1 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.
Figure 3:
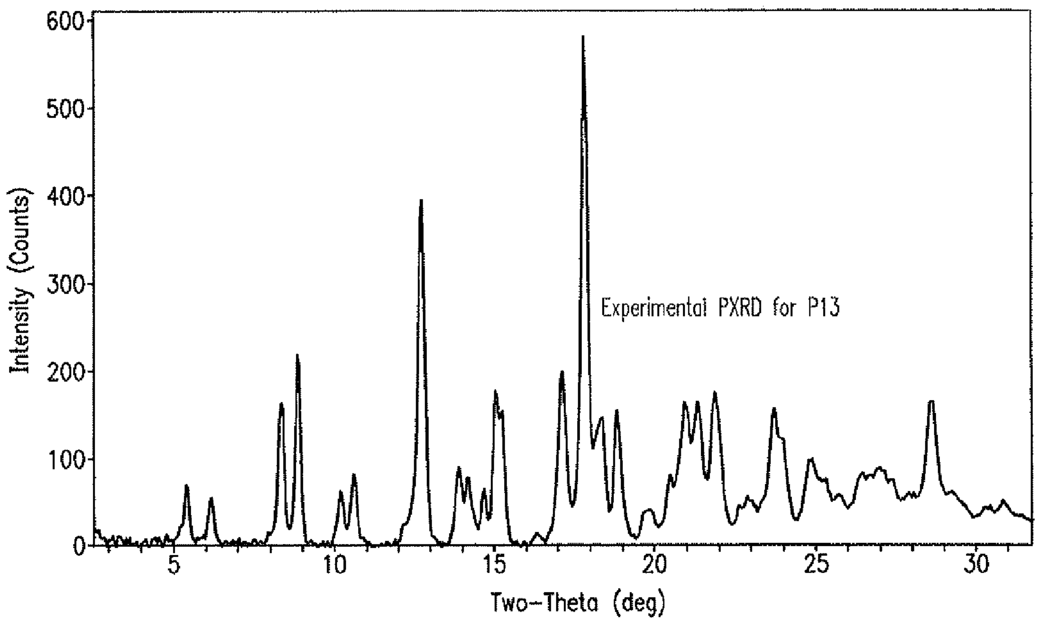
FIG. 3 shows the observed powder X-ray diffraction patterns (CuKa λ=1.5418 Å) of Form P13 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.
Figure 6:
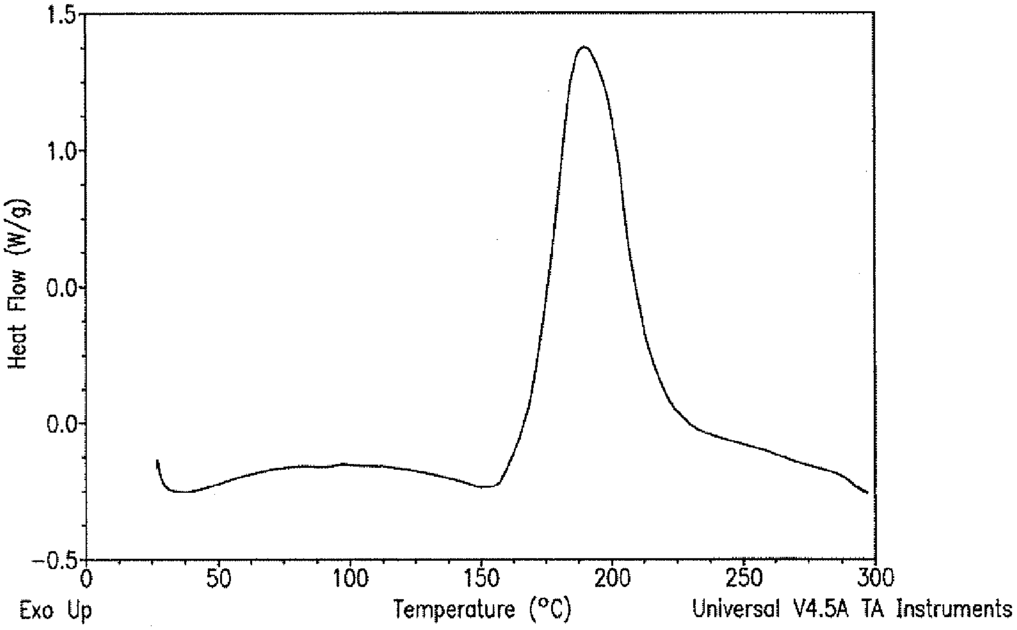
FIG. 6 is a differential scanning calorimetry thermogram of Form H.5-1 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.
Figure 9:
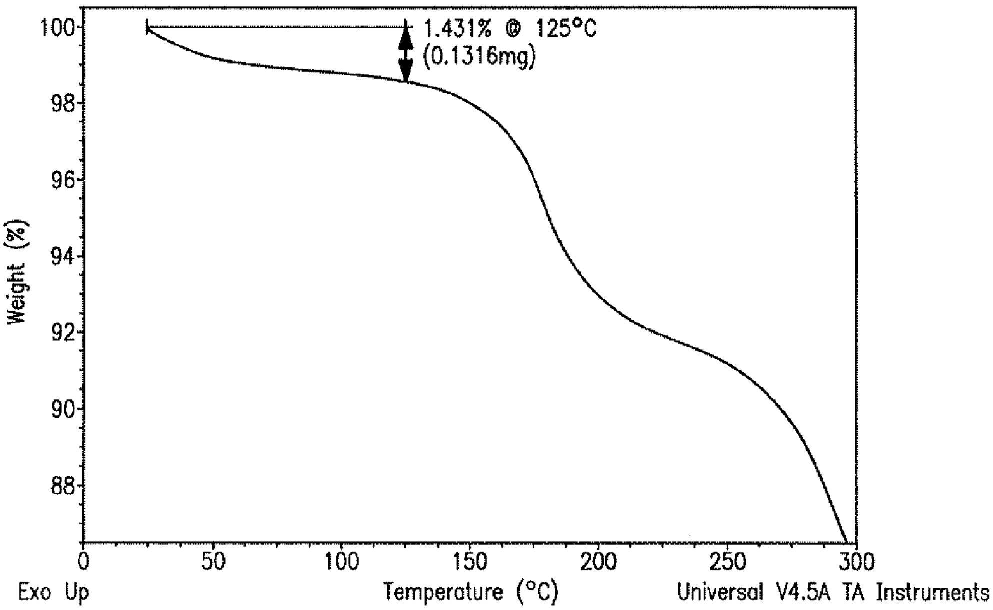
FIG. 9 is a thermogravimetric analysis thermogram of Form H.5-1 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid.
Figure 10:
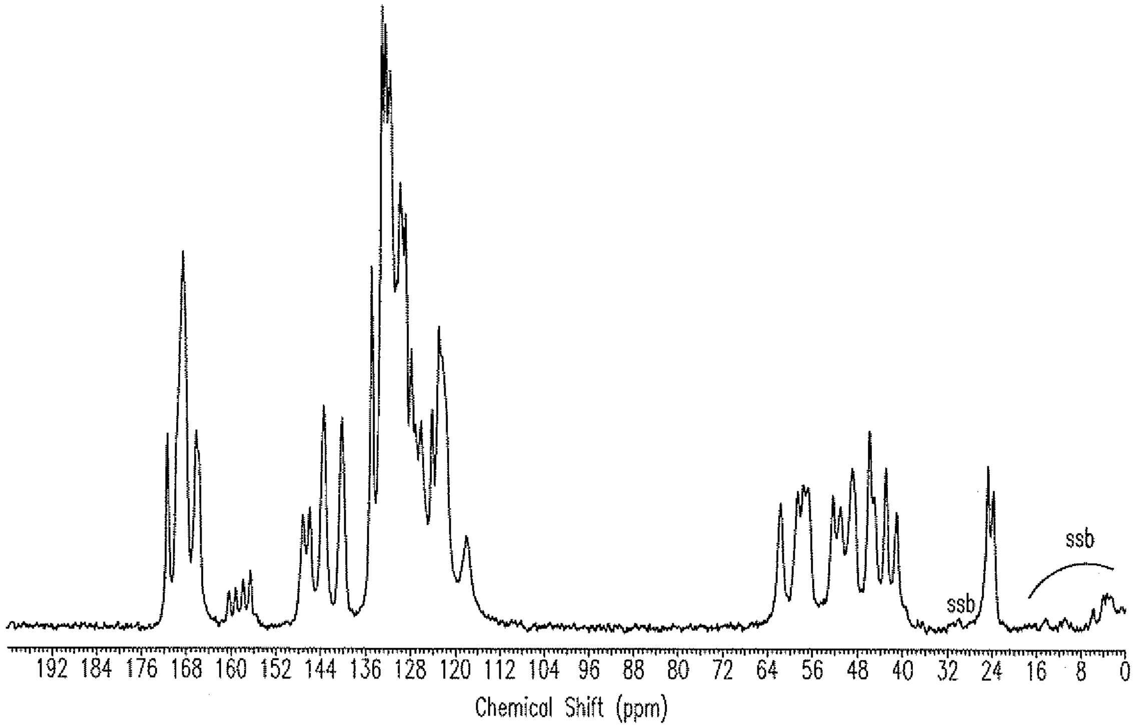
FIG. 10 is a C-13 CPMASA spectrum diagram of Form P13 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid. The spinning sidebands are labeled with "ssb."
Figure 11:
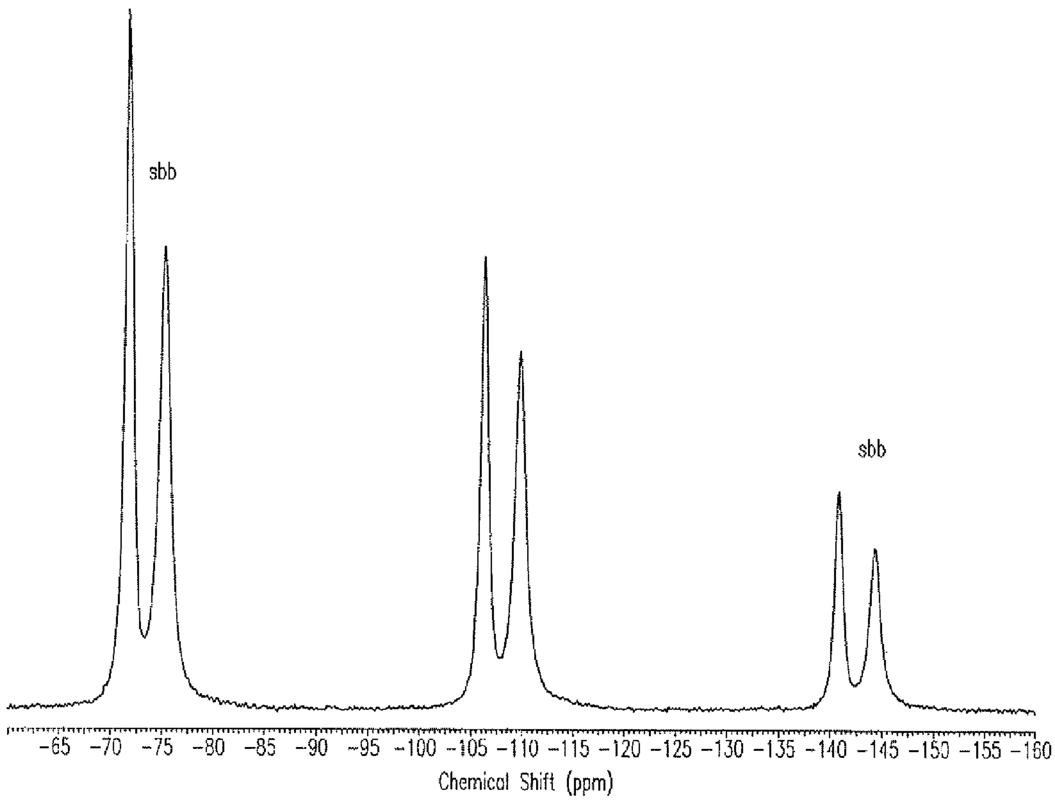
FIG. 11 is a F-19 CPMAS spectrum (with proton decoupling) diagram of Form P13 of crystalline (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid. The spinning side bands are labeled and were confirmed by varying the spinning speed.

60 g of dried crude Compound (I) was dissolved in 240 mL of 200 Proof ethanol (4 mL/g) at room temperature. In one portion, 13.25 mL of triethylamine (1.1 equiv) was added and the reaction mixture was aged for a minimum of 3 h. The solution was cooled to 0° C. and remained at that temperature for a minimum of 30 min. The slurry was filtered and the solids were washed with 30 mL of 200 Proof ethanol (0.5 mL/g). The wet cake was dissolved in 600 mL of purified water (10 mL/g) and stirred for a minimum of 30 min at room temperature. The slurry was filtered and the solids were washed with 120 mL of purified water (2 mL/g) and then 180 mL of purified water (3 mL/g). The wet cake was dried at 45° C. under vacuum for a minimum of 12 h. The obtained crystal was subjected to further analyses and the results are shown in FIGS. 2, 6, and 9.

Example 274

274A: Preparation of Form P13

A slurry of 6.8 g of Example 271 in 33 mL of methanol (4.9 mL/g) and 102 mL of dichlormethane (15 mL/g) was heated to 40° C. and became a homogeneous solution. Atmospheric distillation with constant volume addition of dichloromethane (136 mL) was performed over the next hour with batch temperature maintained at 40° C. The batch was cooled to 15° C., and a solvent swap from dichloromethane/methanol solution to ethyl acetate at constant volume was initiated under reduced pressure (150 mmHg). The batch temperature was raised to 37° C., 400 mL of ethyl acetate was used to complete the solvent swap with a remainder of 136 mL of ethyl acetate in the reactor. The batch was cooled to 20° C. and allowed to age for 12 h. The slurry was filtered and the resulting wet cake was dried at 50° C. under reduced pressure for 6 h. The dried material was subjected to PXRD, Solid-State Nuclear Magnetic Resonance (SSNMR) and the results are shown in FIGS. 3, 5, 8, 10, and 11.

Carbon cross polarization magic angle spinning (CPMAS) solid state NMR experiments were conducted on a Bruker AV III instrument operating at a proton frequency of 400.1 MHz. Solid samples were spun at 13 KHz in a 4 mm ZrO2 rotor. The contact time was 3 miliseconds and was ramped on the proton channel from 50 to 100%. (A. E. Bennett et al, *J. Chem. Phys.*, 1995, 103, 6951), (G. Metz, X. Wu and S. O. Smith, *J. Magn. Reson. A.*, 1994, 110, 219-227). The relaxation delay was maintained at 20 seconds. Proton decoupling was applied using a TPPM sequence with a 4 microsecond pulse (62.5 KHz nominal band width). The spectral sweep width was 300 ppm centered at 100 ppm. 4096 data points were acquired and zero filled to 8192 prior to apodization with 20 Hz line broadening. Typically 2096 free induction decays were coadded. The spectra were referenced indirectly to TMS using 3-methylglutaric acid (D. Barich, E. Gorman, M. Zell, and E. Munson, *Solid State Nuc. Mag. Res.*, 2006, 30, 125-129). Approximately 70 mg of sample was used for each experiment.

Fluorine magic angle spinning (MAS) solid state and cross polarization magic angle spinning (CPMAS) solid state NMR experiments were conducted on a Bruker AV III instrument operating at a proton frequency of 400.1 MHz. Solid samples were spun at 11, 12 and 13 KHz in a 4 mm ZrO2 rotor. Data collected at 13 KHz is reported. The relaxation delay was maintained at 30 seconds for the MAS and 5 seconds for the CPMAS experiments. Proton decoupling was applied to the CPMAS experiments using a TPPM sequence with a 4 microsecond pulse (62.5 KHz nominal band width). The spectral sweep width was 500 ppm centered at −100 ppm. 4096 data points were acquired and zero filled to 8192 prior to apodization with 20 Hz line broadening. Typically 256 free induction decays were coadded. The spectra were referenced indirectly to CC13F using PTFE (at −122 ppm).

Various crystalline forms of (S,E)-4-(2-(3-(3-chloro-2-fluoro-6-(1H-tetrazol-1-yl)phenyl)acryloyl)-5-(4-methyl-2-oxopiperazin-1-yl)-1,2,3,4-tetrahydroisoquinoline-1-carboxamido)benzoic acid and its solvates were prepared and their characteristic peak positions are tabulated in Table 22. The unit cell data and other properties for these examples are tabulated in Tables 23-25. The unit cell parameters were obtained from single crystal X-ray crystallographic analysis. A detailed account of unit cells can be found in Chapter 3 of Stout & Jensen, "*X-Ray Structure Determination: A Practical Guide*", (MacMillian, 1968).

TABLE 22

Characteristic diffraction peak positions (degrees 2θ ± 0.1) @ RT, based on a high quality pattern collected with a diffractometer (CuKα) with a spinning capillary with 2θ calibrated with a NIST other suitable standard.

| HCl:SA-1 | Free Base H.5-1 | Free Base P13 |
|---|---|---|
| 6.0 | 5.9 | 8.4 |
| 8.3 | 7.2 | 8.9 |
| 8.7 | 12.0 | 12.7 |
| 12.3 | 15.7 | 17.9 |
| 16.2 | 17.2 | |
| 16.7 | 18.9 | |
| 17.5 | 20.3 | |
| 19.9 | 24.2 | |
| 20.4 | 26.1 | |

TABLE 23

Cell Parameters for Single crystal (input) and hybrid (refined) for Form HCl: SA-1

| Cell Parameter | Input | Refined |
|---|---|---|
| a (Å) | 8.3746 | 8.2562 |
| b(Å) | 20.2236 | 20.2918 |
| c(Å) | 21.3099 | 21.2423 |
| α° | 90 | 90 |
| β° | 90 | 90 |
| γ° | 90 | 90 |
| Volume ($Å^3$) | 3609.14 | 3558.77 |

TABLE 24

| Carbon Chemical Shifts (referenced to external TMS) for P13 | |
|---|---|
| No. | (ppm) |
| 1 | 23.8 |
| 2 | 24.8 |
| 3 | 41.1 |
| 4 | 43.0 |
| 5 | 45.1 |
| 6 | 45.9 |
| 7 | 48.5 |
| 8 | 49.0 |
| 9 | 51.0 |
| 10 | 52.4 |
| 11 | 56.8 |
| 12 | 57.6 |
| 13 | 58.6 |
| 14 | 61.7 |
| 15 | 118.1 |
| 16 | 121.7 |
| 17 | 122.0 |
| 18 | 122.5 |
| 19 | 123.0 |
| 20 | 124.2 |
| 21 | 126.1 |
| 22 | 127.1 |
| 23 | 127.9 |
| 24 | 129.0 |
| 25 | 129.9 |
| 26 | 130.5 |
| 27 | 130.6 |
| 28 | 131.8 |
| 29 | 132.6 |
| 30 | 133.3 |
| 31 | 135.0 |
| 32 | 139.9 |
| 33 | 140.4 |
| 34 | 143.6 |
| 35 | 146.1 |
| 36 | 147.3 |
| 37 | 156.6 |
| 38 | 157.9 |
| 39 | 159.2 |
| 40 | 160.4 |
| 41 | 165.7 |
| 42 | 166.3 |
| 43 | 168.7 |
| 44 | 169.7 |
| 45 | 171.4 |

TABLE 25

| F-19 Chemical Shifts (referenced to external $CCl_3F$) for P13 | |
|---|---|
| No. | (ppm) |
| 1 | −109.8 |
| 2 | −106.3 |

Numerous modifications and variations of the present invention are possible in light of the above teachings. It is therefore to be understood that within the scope of the appended claims, the invention may be practiced otherwise than as specifically described herein.

What is claimed is:

1. A compound selected from the formulae:

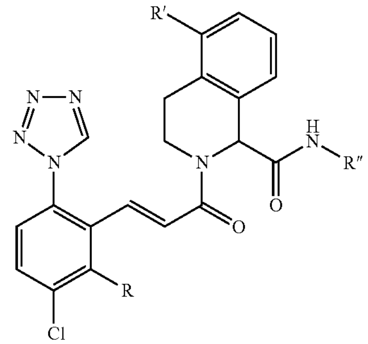

| R | R' | R" |
|---|---|---|
| H | Piperazine | 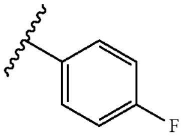 [SMILES: *c1ccc(F)cc1] |
| F | Piperazine | 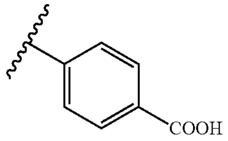 [SMILES: *c1ccc(C(=O)O)cc1] |
| F | Piperazine | 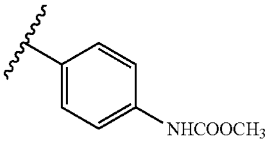 |
| F | Piperazine | 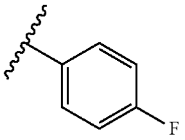 [SMILES: *c1ccc(F)cc1] |
| F | Piperazine | 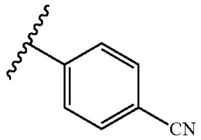 [SMILES: *c1ccc(C#N)cc1] |
| F | Piperazine | 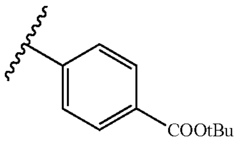 |
| F | Piperazine | 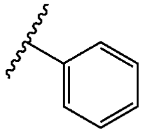 [SMILES: *c1ccccc1] |
| F | Piperazine | 6-indazole-1-CBz |
| F | Boc-piperazine | 6-indazole-1-tBoc |
| F | Piperazine | 6-indazole, |

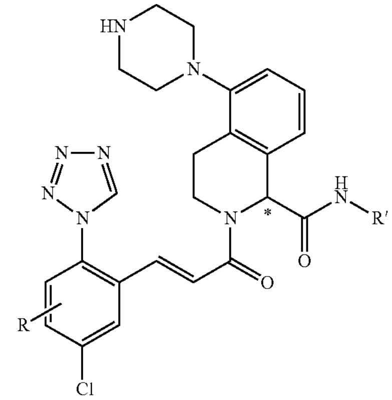
| R | R' |
|---|---|
| 2-F | 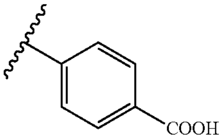 [SMILES: *c1ccc(C(=O)O)cc1] |
| 2-F | 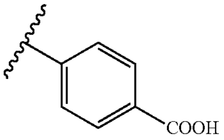 [SMILES: *c1ccc(C(=O)O)cc1] |
| 4-F | 6-indazole |
| 4-F | 6-indazole |
| 4-F | 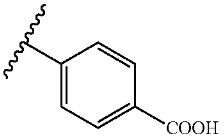 [SMILES: *c1ccc(C(=O)O)cc1] |
| 4-F | 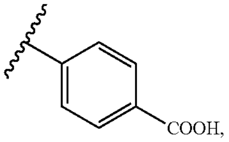 [SMILES: *c1ccc(C(=O)O)cc1] |
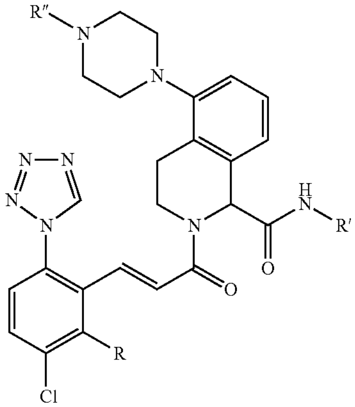
| R | R' | R" |
|---|---|---|
| F | -4-PhCOOH | $CH_3$ |
| H | -4-PhNHCOOCH$_3$ | $CH_3$ |
-continued
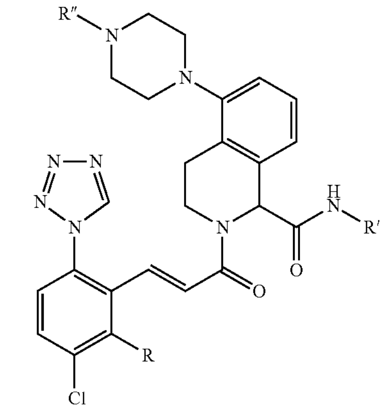
| R | R' | R" |
|---|---|---|
| F | -4-PhCN | $CH_3$ |
| H | -4-PhCOOH | 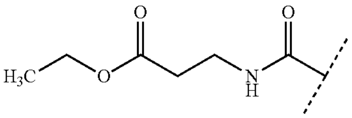 |
| H | -4-PhCOOH | $CH_3OOC$— |
| H | -4-PhNHCOOCH$_3$ | 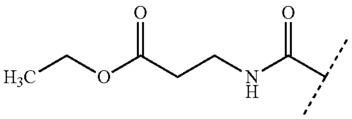 |
| F | -4-PhNHCOOCH$_3$ | $CH_3OOC$— |
| F | -4-PhF | $CH_3OOC$— |
| F | -4-PhCN | $CH_3OOC$— |
| F | 6-indazole | $CH_3$, |
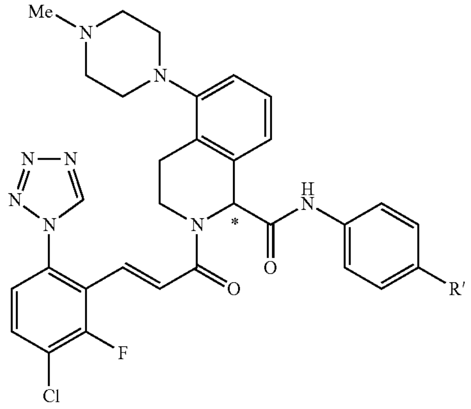
| R' |
|---|
| COOEt |
| COOEt |
| COOH |
| COOH, |

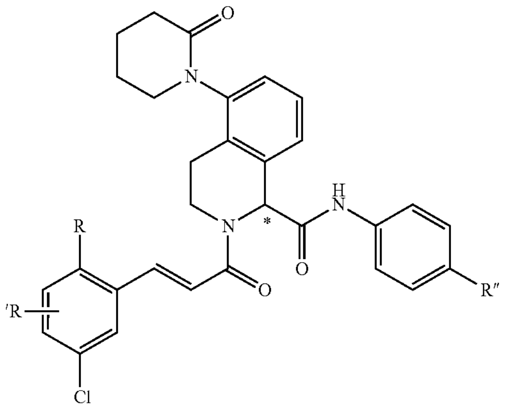
| R | R' | R'' |
|---|---|---|
| tetrazole | 2-F | COOH |
| tetrazole | 2-F | COOH |
| tetrazole | 2-F | COOH |
| tetrazole | 2-F | COOtBu |
| —COMe | 2-F | COOH |
| —COMe | 2-F | COOH |
| —COMe | 2-F | COOH |
| tetrazole | 4-F | COOH |
| tetrazole | 4-F | COOH |
| tetrazole | 2-F | COOEt |
| tetrazole | 2-F | COOEt |
| tetrazole | 2-F | COOEt, |
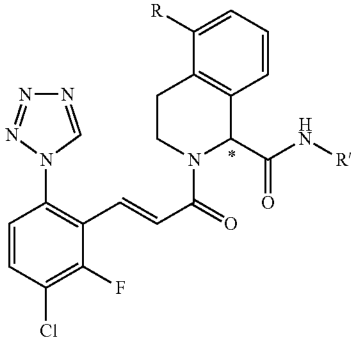
| R | R' |
|---|---|
| 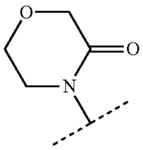 | -4-PhCOOH |
| 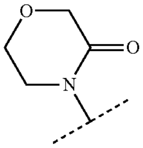 | 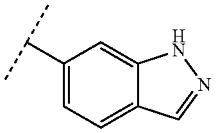 |
| 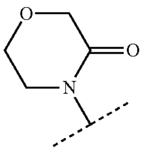 | -4-PhCOOH |
-continued
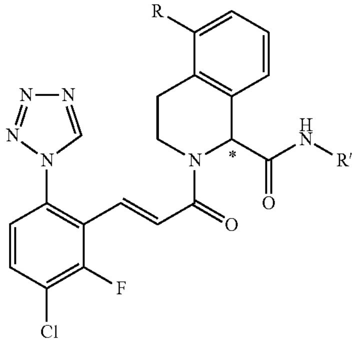
| R | R' |
|---|---|
| 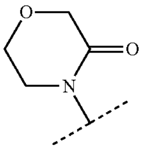 | -4-PhCOOH |
| 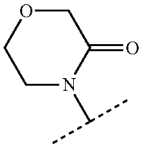 | -4-PhCOOtBu |
| 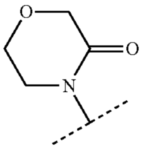 | -4-PhCOOEt |
| 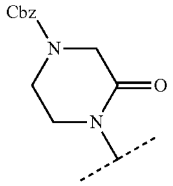 | -4-PhCOOH |
| 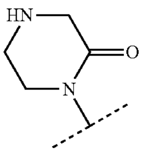 | 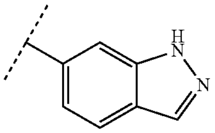 |
| 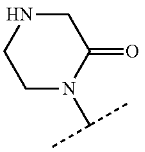 | -4-PhCOOH |
| 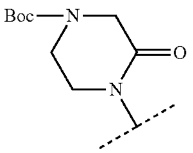 | -4-PhCOOtBu |

-continued
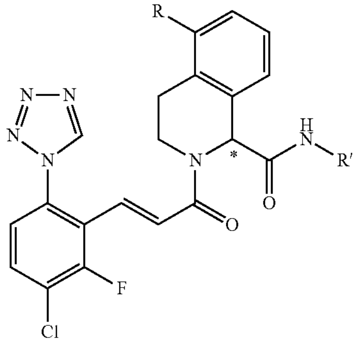
| R | R' |
|---|---|
| 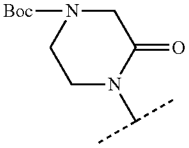 | -4-PhCOOEt |
| 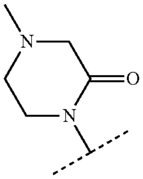 | -4-PhCOOtBu |
| 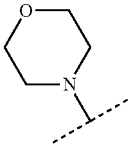 | $-4-PhNHCOOCH_3$ |
| 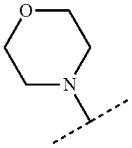 | -4-PhCOOtBu |
| 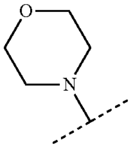 | 4-PhCOOH |
| 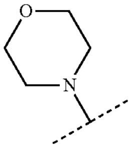 | 4-PhCOOH |
| 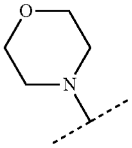 | 4-PhCOOH |
-continued
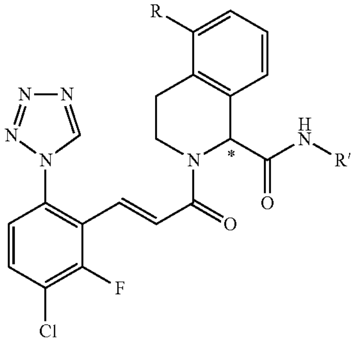
| R | R' |
|---|---|
| 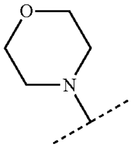 | -4-PhCOOEt |
| 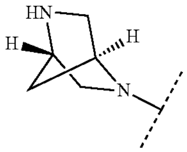 | 4-PhCOOH, |
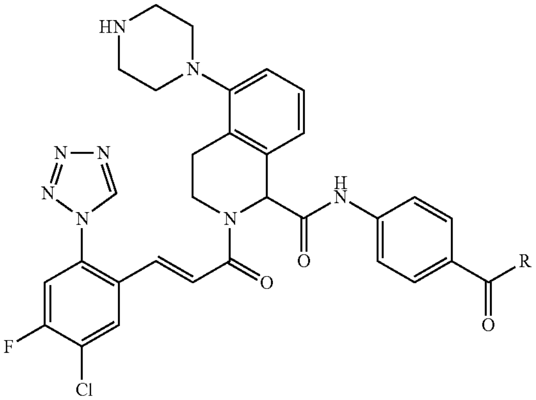
| R |
|---|
| Cyclopropanamine |
| 2-(1H-imidazol-4-yl)ethanamine |
| Aniline |
| N-(4-aminophenyl)acetamide |
| Ethyl |
| N-(2-aminoethyl)acetamide |
| 3-aminopropanamide |
| methyl 2-aminoacetate |
| 3-methoxyaniline |
| Dimethylamine |
| Methylamine, |

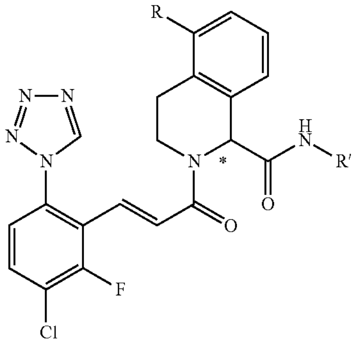
| R | R' |
|---|---|
| 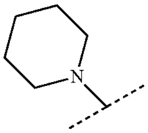 | -4-PhCOOH |
| 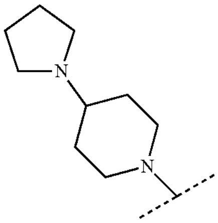 | -4-Ph—F |
| 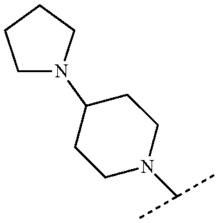 | -4-PhCOOEt |
| 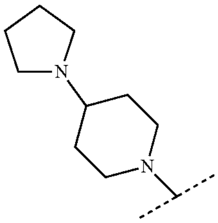 | -4-PhCOOtBu |
| 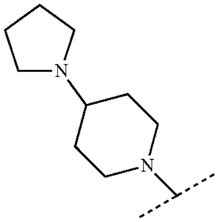 | 4-PhCN |
-continued
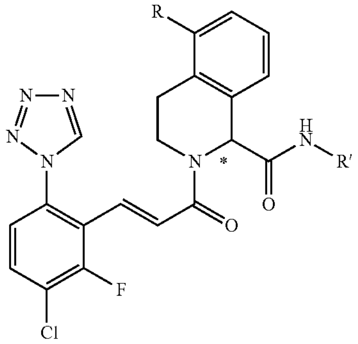
| R | R' |
|---|---|
| 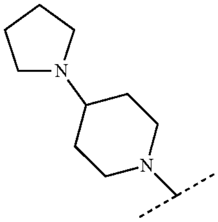 | -4-Ph—F |
| 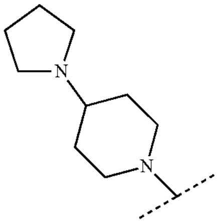 | -4-PhCOOH |
| 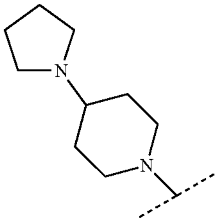 | -4-PhCOOH |
| 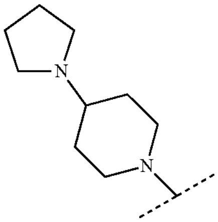 | -4-PhNHCOOCH$_3$ |
| 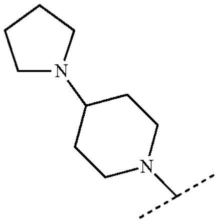 | -4-Ph—F |

-continued
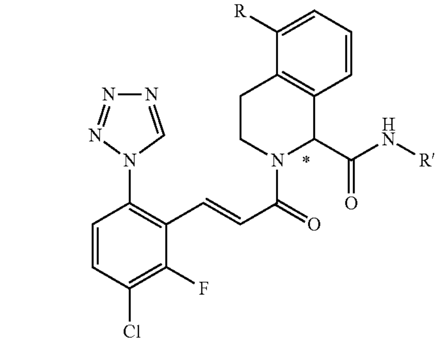
| R | R' |
|---|---|
| 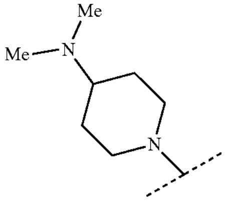 | -4-PhCOOtBu |
| 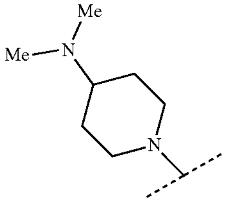 | -4-PhCOOH |
| 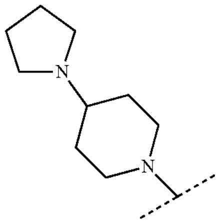 | -4-Ph—COOEt |
| 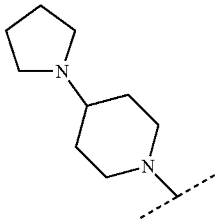 | -4-Ph—COOEt |
| 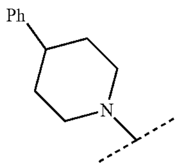 | -4-PhCOOH |
-continued
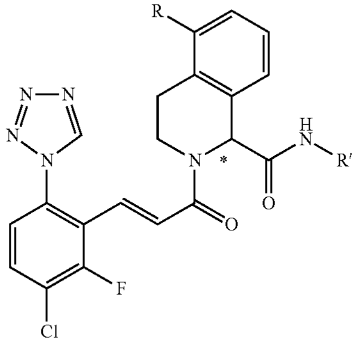
| R | R' |
|---|---|
| 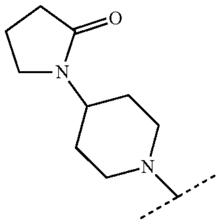 | -4-PhCOOH |
| 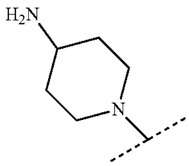 | -4-PhCOOH |
| 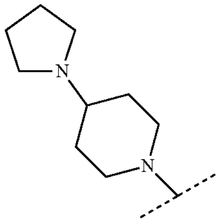 | -4-PhNHCOOCH$_3$ |
| 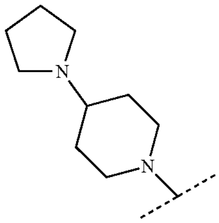 | -4-PhNHCOOCH$_3$ |
| 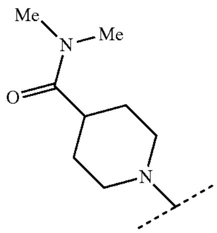 | -4-PhCOOH |

-continued
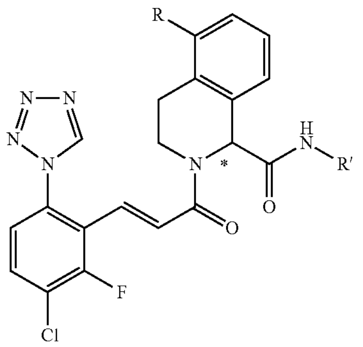
| R | R' |
|---|---|
| 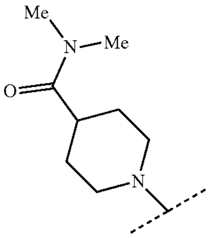 | -4-PhCOOH |
| 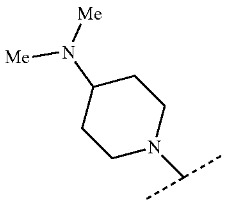 | -4-PhCOOH |
| 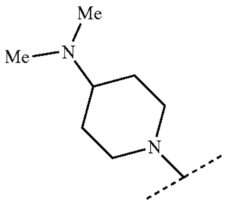 | -4-PhCOOH |
| 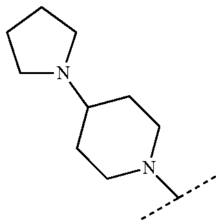 | -4-Ph—Cl |
| 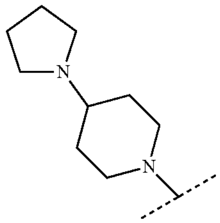 | -4-PhCOOnBu |
-continued
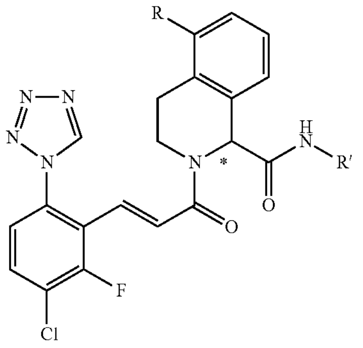
| R | R' |
|---|---|
| 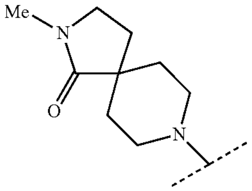 | -4-PhCOOH |
| 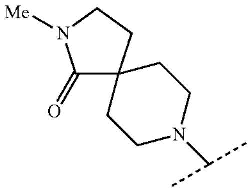 | -4-PhCOOH |
| 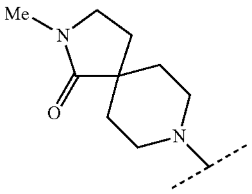 | -4-PhCOOH |
| 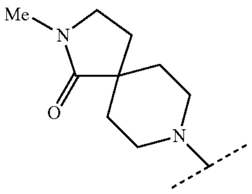 | -4-PhCOOEt |
| 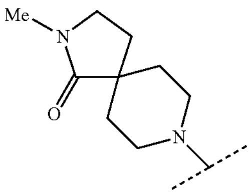 | -4-PhCOOEt |
| 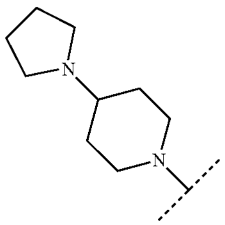 | -4-Ph—Cl |

-continued
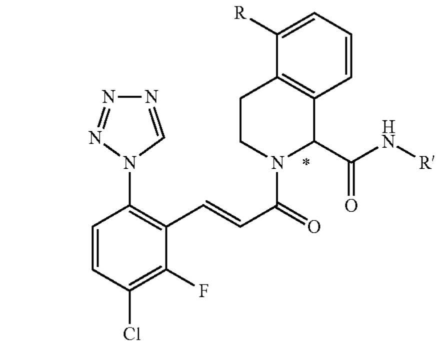
| R | R' |
| --- | --- |
| 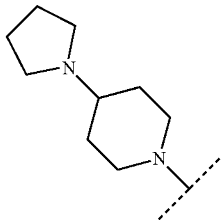 | -4-Ph—Cl |
| 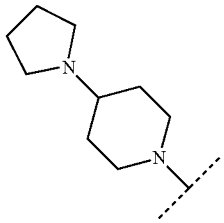 | -4-PhCOOnBu |
| 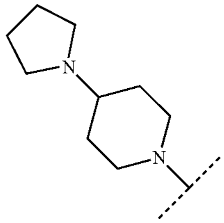 | -4-PhCOOnBu |
| 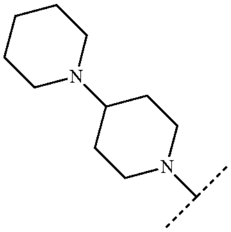 | -4-PhCOOH |
| 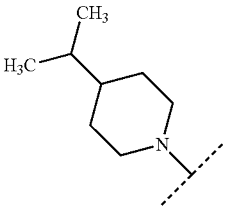 | -4-PhCOOH |
-continued
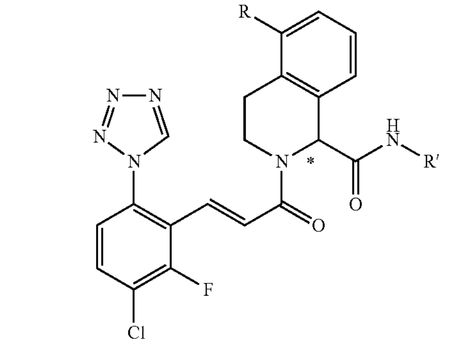
| R | R' |
| --- | --- |
| 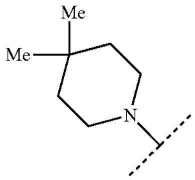 | 4-PhCOOH |
| 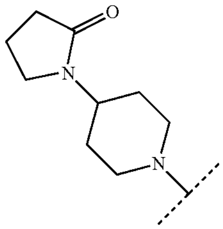 | -4-PhCOOH |
| 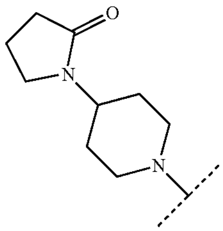 | -4-PhCOOH |
| 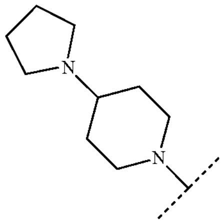 | 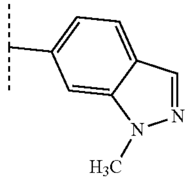 |
| 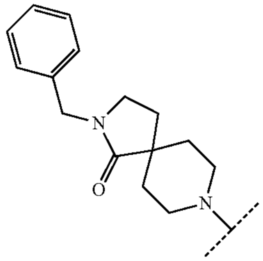 | -4-PhCOOH |

-continued
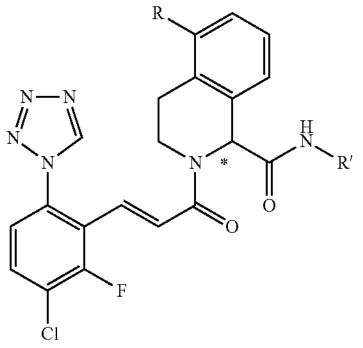
| R | R' |
|---|---|
| 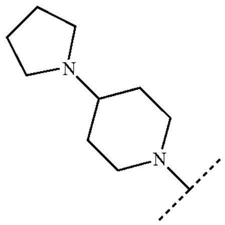 | -4-PhCOOiPr |
| 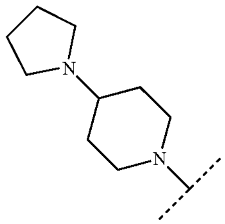 | -4-PhCOOiBu |
| 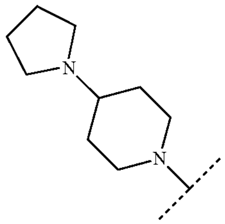 | 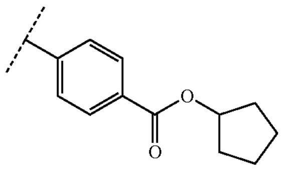 |
| 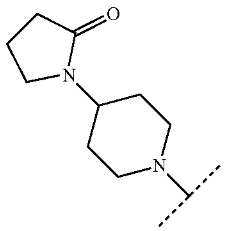 | -4-Ph—COOEt |
| 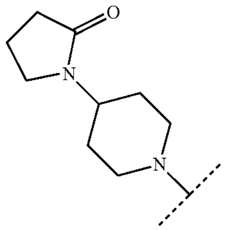 | -4-Ph—COOEt |
-continued
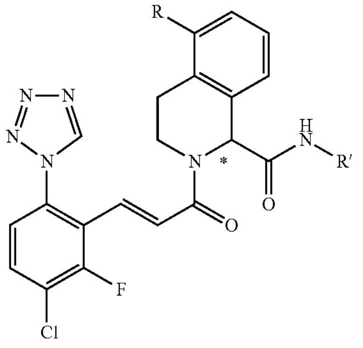
| R | R' |
|---|---|
| 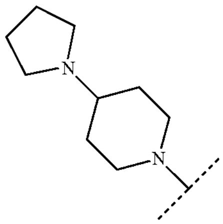 | 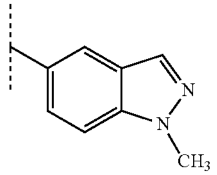 |
| 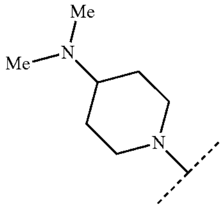 | -4-PhCOOEt |
| 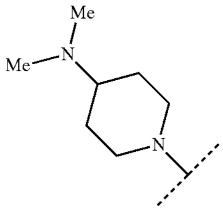 | -4-PhCOOEt |
| 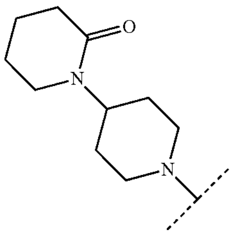 | -4-PhCOOH |
| 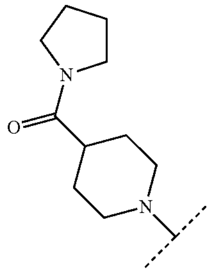 | -4-PhCOOH |

-continued
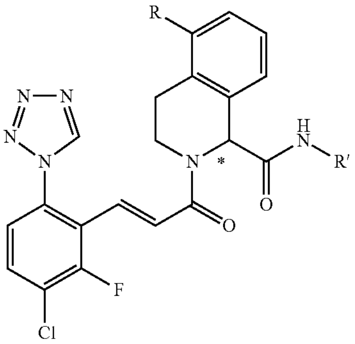
| R | R' |
|---|---|
| 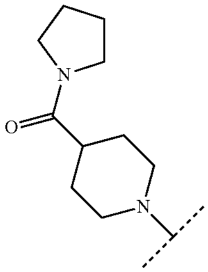 | -4-PhCOOH |
| 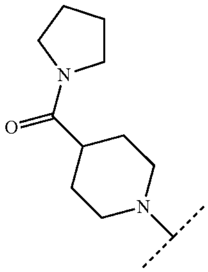 | -4-PhCOOH |
| 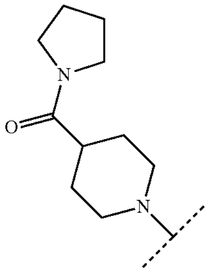 | -4-PhCOOEt |
| 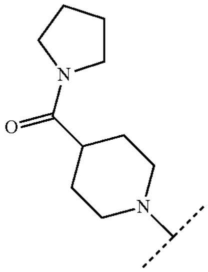 | -4-PhCOOEt |
-continued
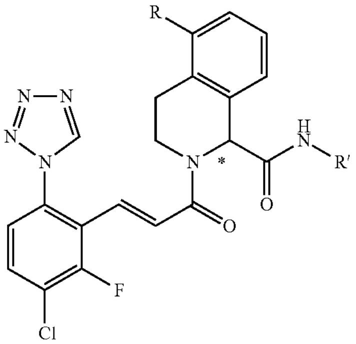
| R | R' |
|---|---|
| 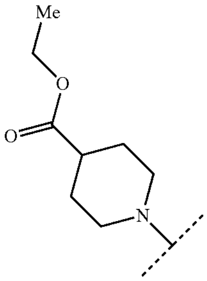 | -4-PhCOOH |
| 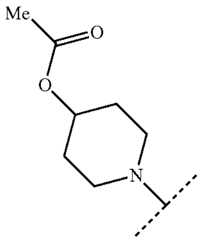 | -4-PhCOOH |
| 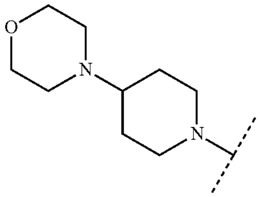 | -4-PhCOOH |
| 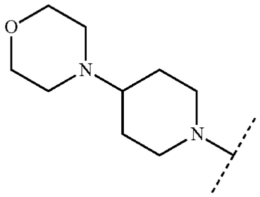 | -4-PhCOOH |
| 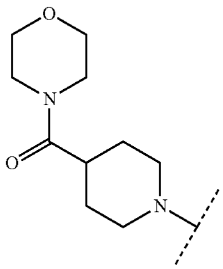 | -4-PhCOOH |

-continued
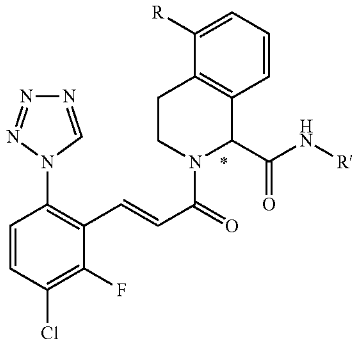
| R | R' |
|---|---|
| 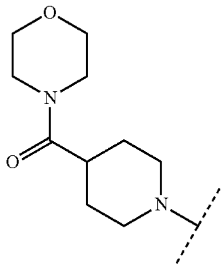 | -4-PhCOOH |
| 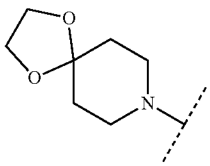 | -4-PhCOOH |
| 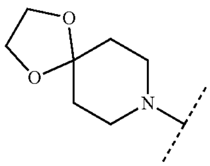 | -4-PhCOOH |
| 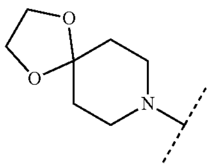 | -4-PhCOOMe |
| 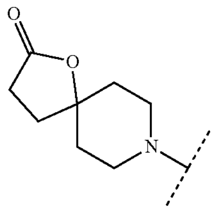 | -4-PhCOOH |
| 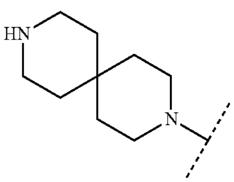 | -4-PhCOOH |
-continued
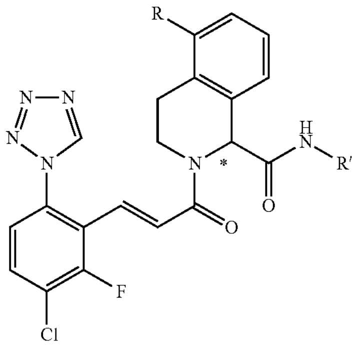
| R | R' |
|---|---|
| 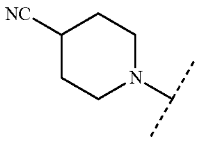 | -4-PhCOOH |
| 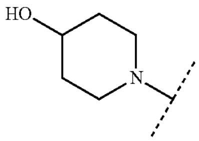 | -4-PhCOOH |
| 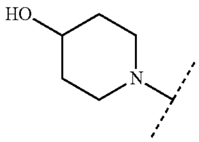 | -4-PhCOOH |
| 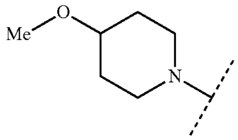 | -4-PhCOOH |
| 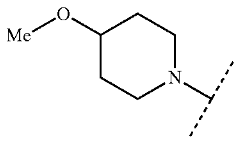 | -4-PhCOOH |
| 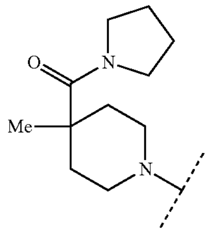 | -4-PhCOOH, |

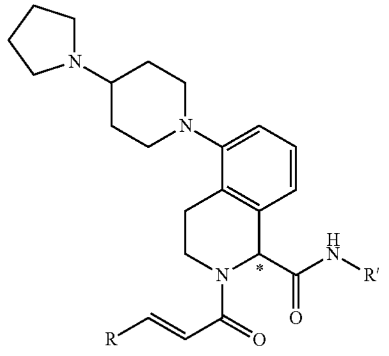
| R | R' |
|---|---|
| 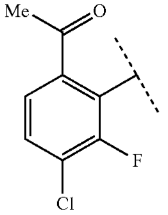 | -4-PhCOOtBu |
| 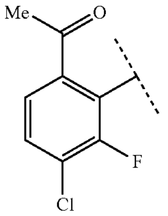 | -4-PhCOOH |
| 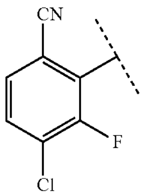 | -4-PhCOOH |
| 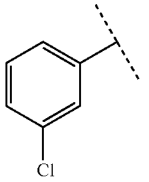 | -4-PhCOOH |
| 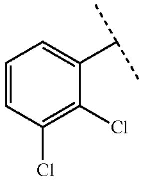 | -4-PhCOOH |
| 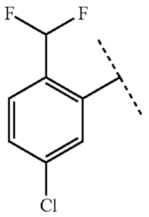 | -4-PhCOOH |
-continued
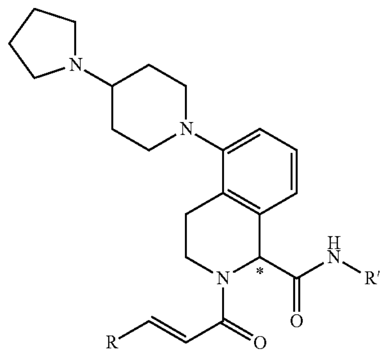
| R | R' |
|---|---|
| 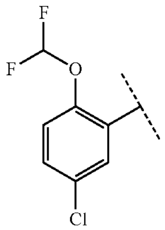 | -4-PhCOOH |
| 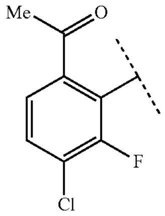 | -4-PhCOOEt |
| 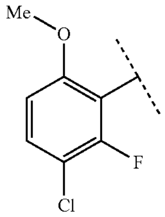 | -4-PhCOOH |
| 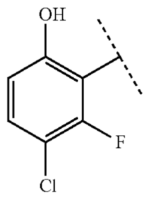 | -4-PhCOOH |
| 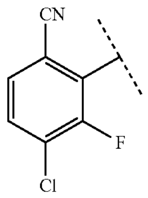 | -4-PhCOOH |

-continued
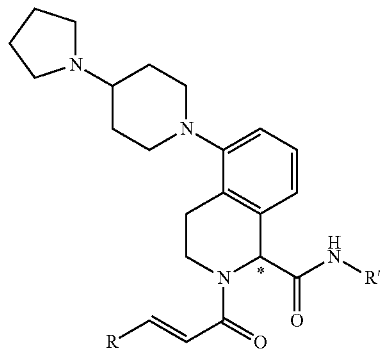
| R | R' |
|---|---|
| 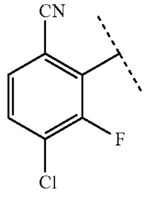 | -4-PhCOOH |
| 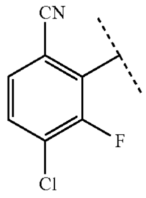 | -4-PhCOOEt |
| 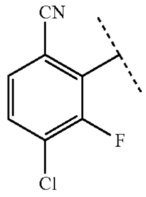 | -4-PhCOOEt |
| 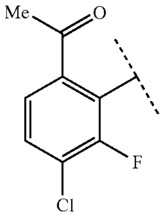 | -4-PhCOOH |
| 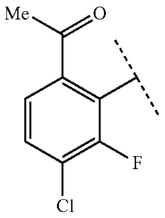 | -4-PhCOOH |
-continued
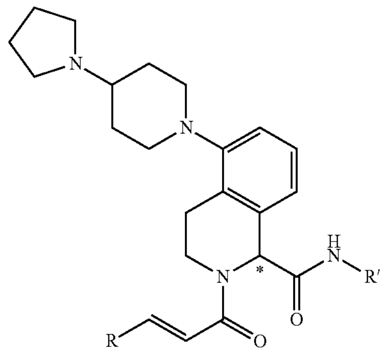
| R | R' |
|---|---|
| 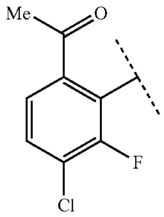 | -4-PhCOOEt |
| 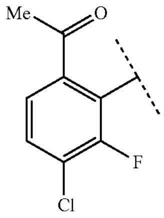 | -4-PhCOOEt |
| 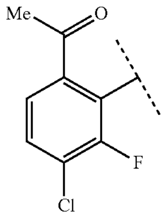 | -4-PhCOOBzl |
| 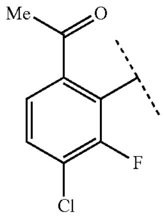 | -4-PhCOOCH2CON($CH_3$)$_2$ |
| 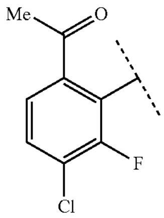 | 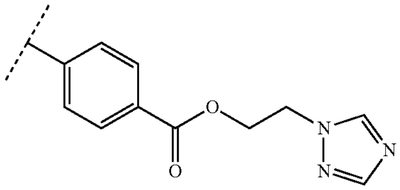 |

-continued
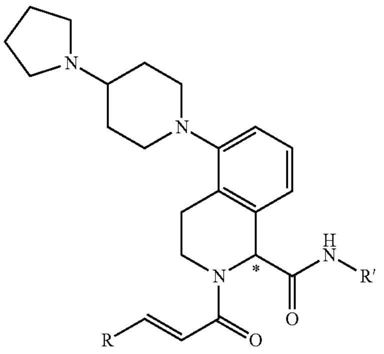
| R | R' |
|---|---|
| 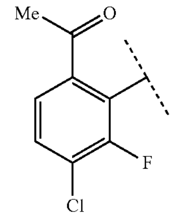 | 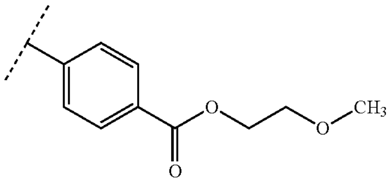 |
| 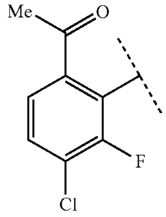 | -4-PhCOOCH$_3$ |
| 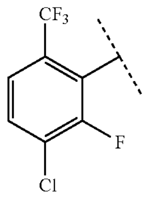 | -4-PhCOOH |
| 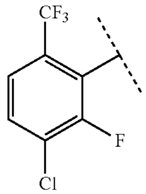 | -4-PhCOOEt |
-continued
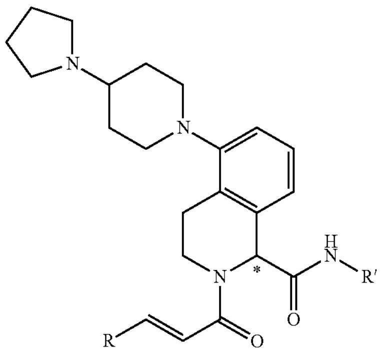
| R | R' |
|---|---|
| 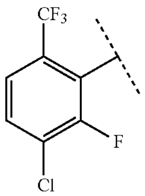 | -4-PhCOOH |
| 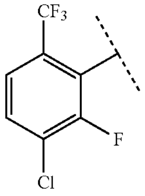 | -4-PhCOOH |
| 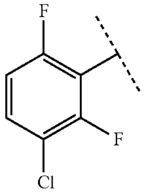 | -4-PhCOOH |
| 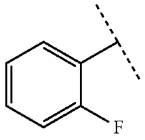 | -4-PhCOOH |
| 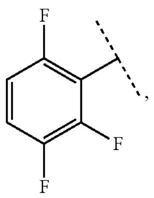 | -4-PhCOOH, |

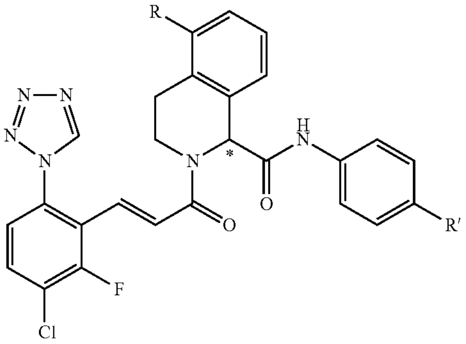
| R | R' |
|---|---|
| 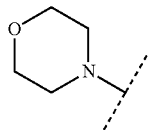 | —COOEt |
| 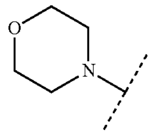 | —COOEt |
| 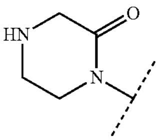 | —COOH |
| 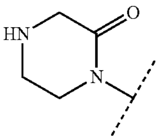 | —COOH |
| 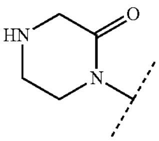 | —COOEt |
| 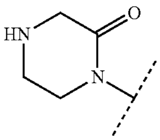 , | —COOEt, |
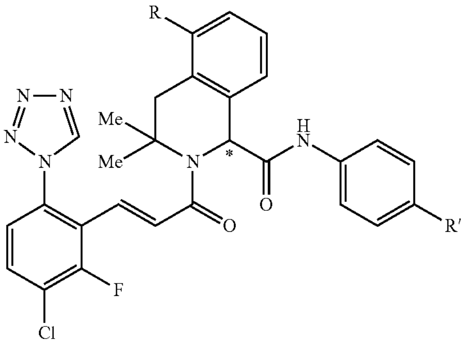
| R | R' |
|---|---|
| 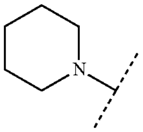 | —COOH |
| 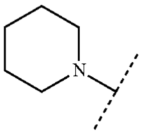 | —COOH |
| 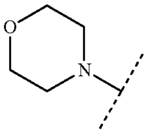 | —COOEt |
| 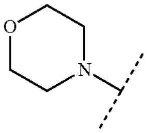 | —COOEt |
| 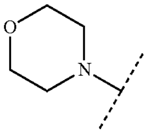 | —COOH |
| 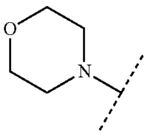 | —COOH |
| 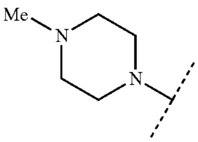 | —COOH |
| 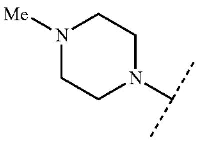 | —COOH |

-continued
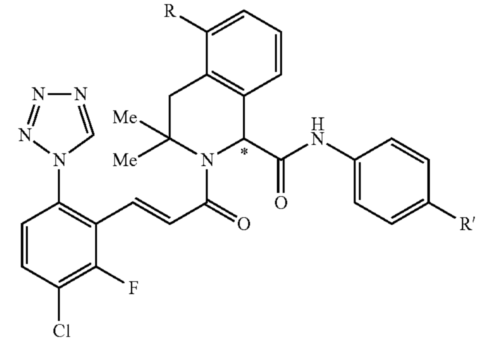
| R | R' |
|---|---|
| 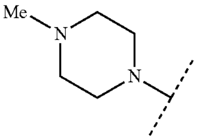 | —COOEt |
| 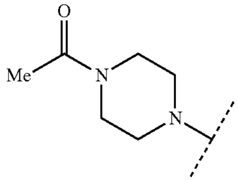 | —COOH |
| 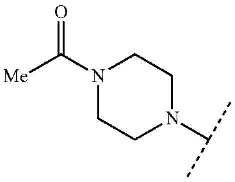, | —COOH, |
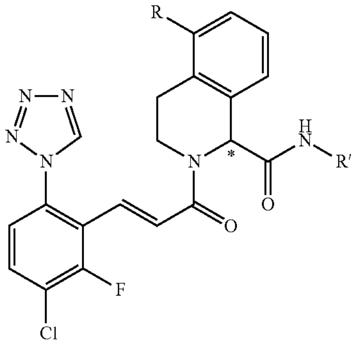
| R | R' |
|---|---|
| 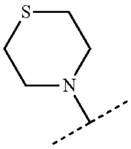 | -4-PhCOOH |
-continued
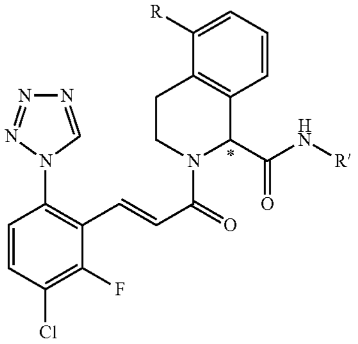
| R | R' |
|---|---|
| 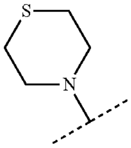 | -4-PhCOOH |
| 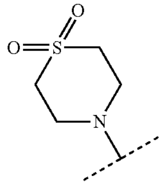 | -4-PhCOOH |
| 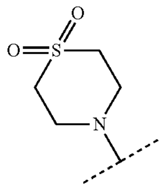, | -4-PhCOOH, |
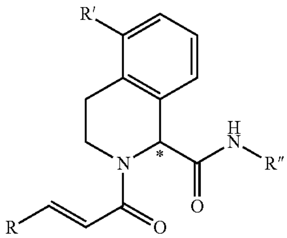
| R | R' | R" |
|---|---|---|
| 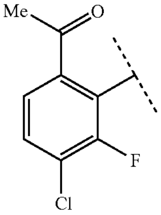 | 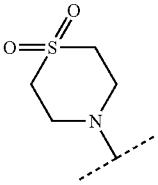 | -4-PhCOOH |

-continued
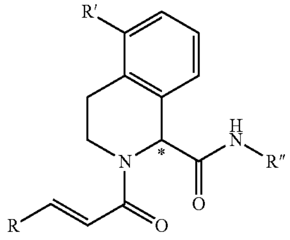
| R | R' | R'' |
|---|---|---|
| 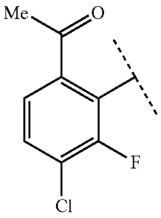 | 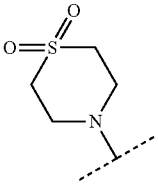 | -4-PhCOOH |
| 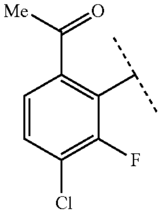 | 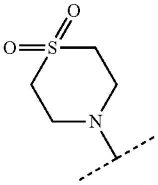 | -4-PhCOOH |
| 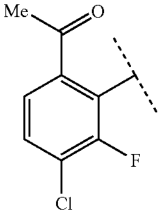 | 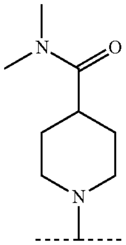 | -4-PhCOOH |
| 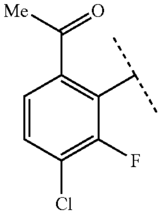 | 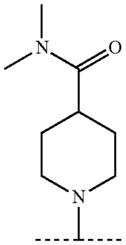 | -4-PhCOOH |
| 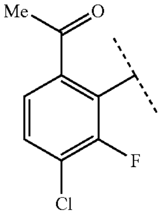 | 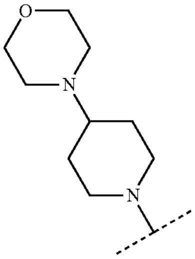 | -4-PhCOOH |
-continued
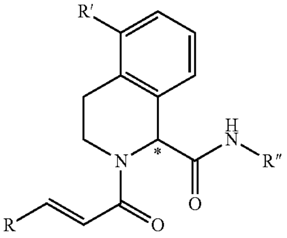
| R | R' | R'' |
|---|---|---|
| 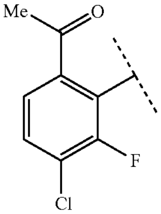 | 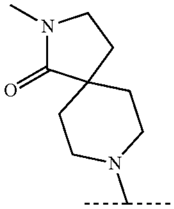 | -4-PhCOOH |
| 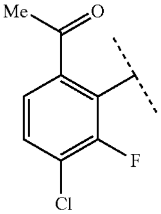 | 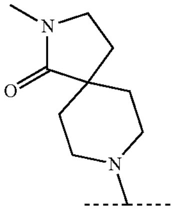 | -4-PhCOOH |
| 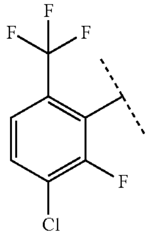 | 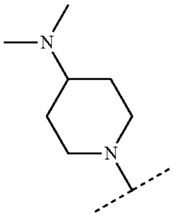 | -4-PhCOOH |
| 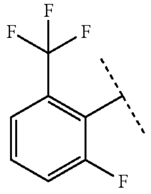 | 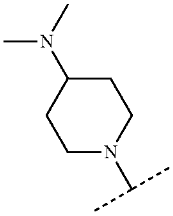 | -4-PhCOOH |
| 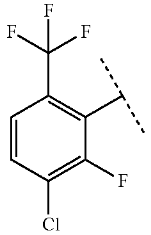 | 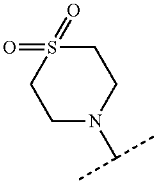 | -4-PhCOOH |

-continued
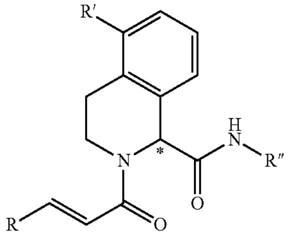
| R | R' | R" |
|---|---|---|
| 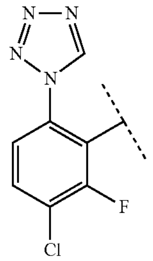 | 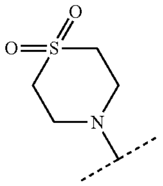 | -4-PhCOOEt |
| 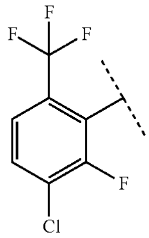 | 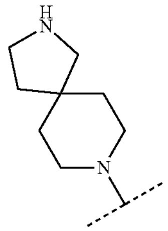 | -4-PhCOOH |
| 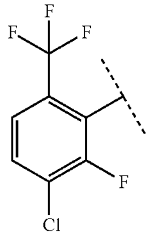 | 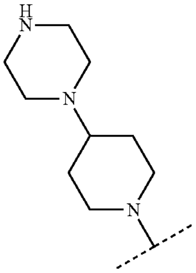 | -4-PhCOOH, |
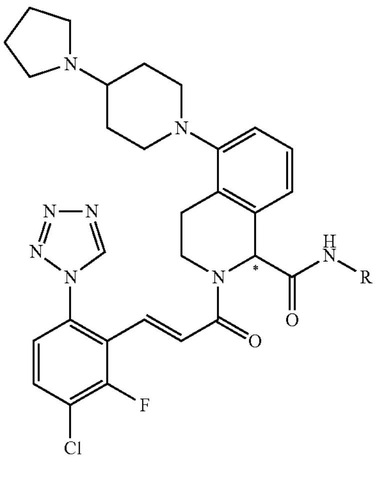
wherein R is selected from:
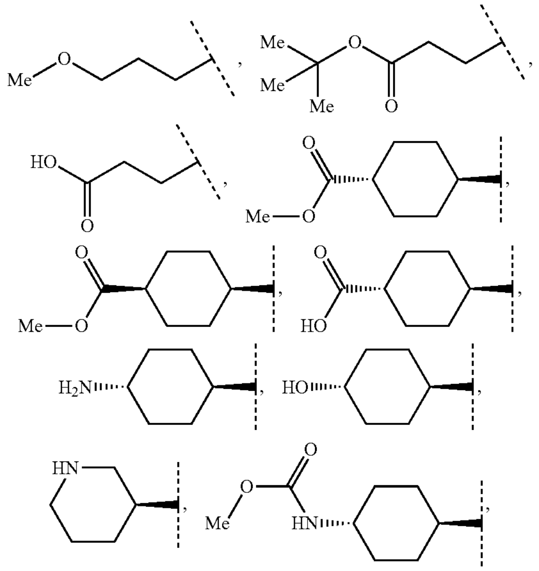
and
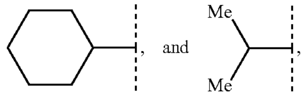
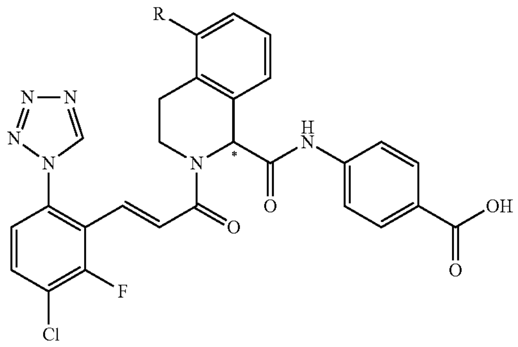
wherein R is selected from:
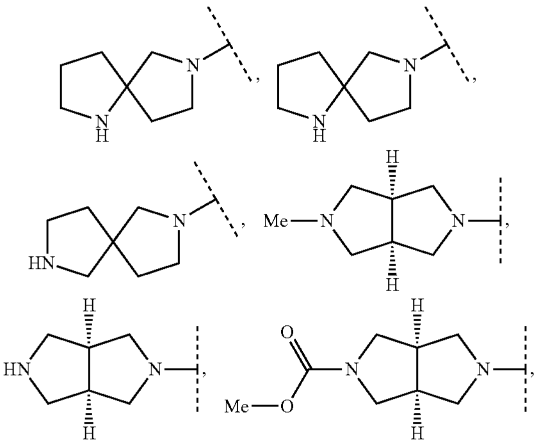

-continued
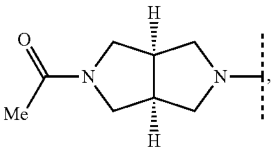,
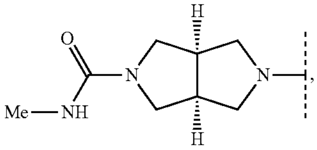,
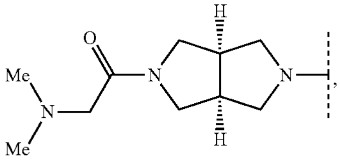, and
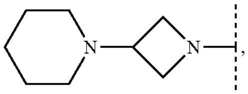,
| | |
|---|---|
| 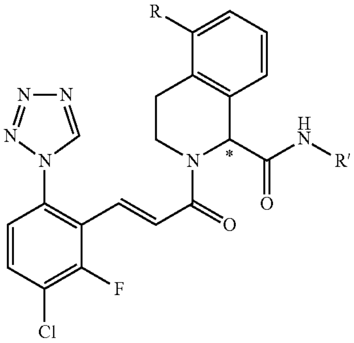 | |
| R | R' |
| 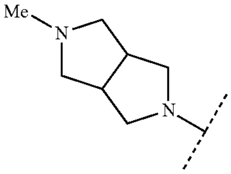 | 4-PhCOOEt |
| 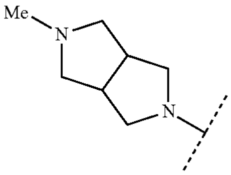 | 4-PhCOOH |
| 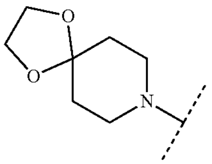 | 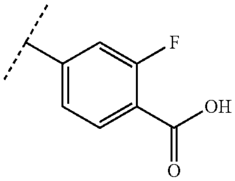 , |
| | |
|---|---|
| 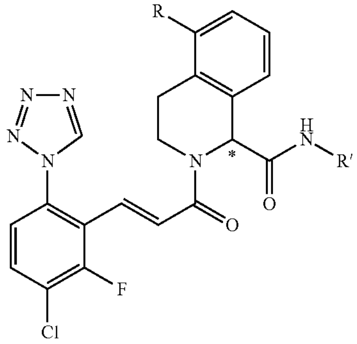 | |
| R | R' |
| 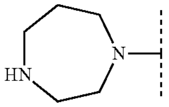 | 4-PhCOOH |
| 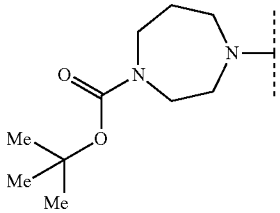 | 4-PhCOOtBu |
| 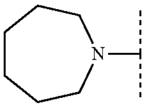 | 4-PhCOOH |
| 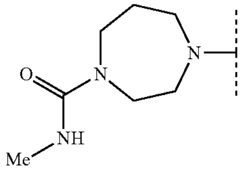 | 4-PhCOOH |
| 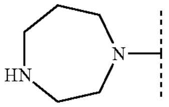 | 4-PhCOOH |
| 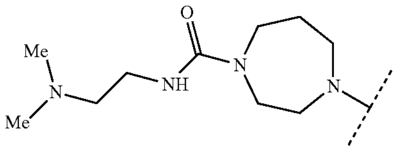 | 4-PhCOOH |
| 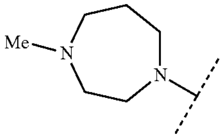 | 4-PhCOOH |
| 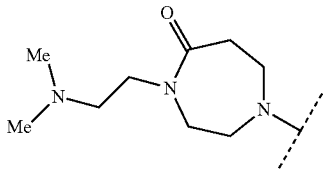 | 4-PhCOOH |

-continued
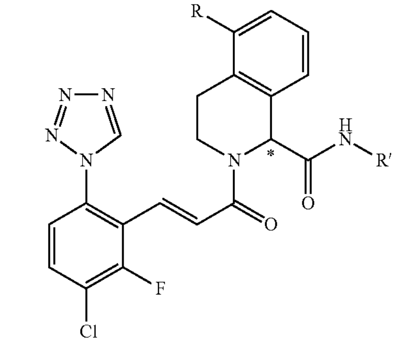
| R | R' |
| --- | --- |
| 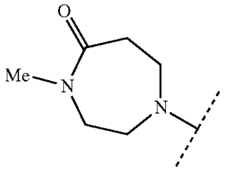 | 4-PhCOOH |
| 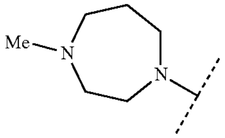 | 4-PhCOOH |
| 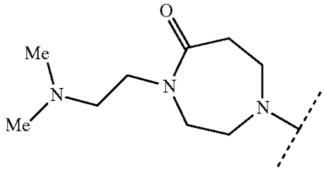 | 4-PhCOOH, and |
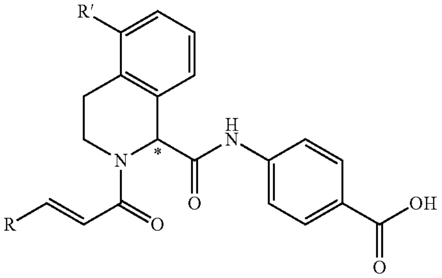
| R | R' |
| --- | --- |
| 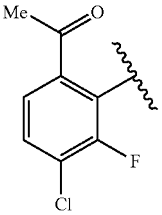 [SMILES: *c1c(C(C)=O)ccc(Cl)c1F] | 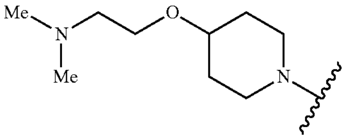 |
-continued
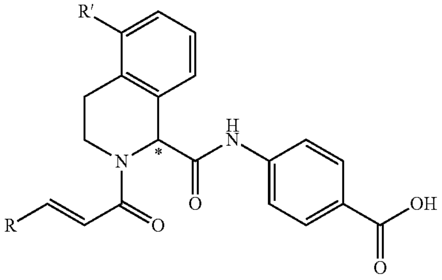
| R | R' |
| --- | --- |
| 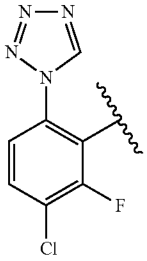 [SMILES: *c1c(-n2cnnn2)ccc(Cl)c1F] | 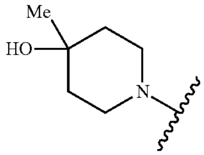 [SMILES: *N1CCC(C)(O)CC1] |
| 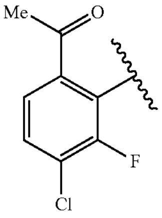 [SMILES: *c1c(C(C)=O)ccc(Cl)c1F] | 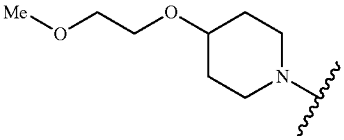 [SMILES: *N1CCC(OCCOC)CC1] |
| 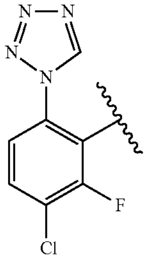 [SMILES: *c1c(-n2cnnn2)ccc(Cl)c1F] | 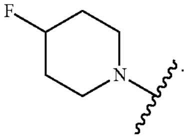 |
* * * * *